(12) United States Patent  (10) Patent No.: US 8,267,947 B2
Pantages et al.  (45) Date of Patent: Sep. 18, 2012

(54) VASCULAR SUTURING DEVICE

(75) Inventors: Anthony J. Pantages, San Jose, CA (US); Brian A. Ellingwood, Sunnyvale, CA (US); Erik K. Walberg, Redwood City, CA (US)

(73) Assignee: Abbott Laboratories, Abbott Park, IL (US)

( * ) Notice: Subject to any disclaimer, the term of this patent is extended or adjusted under 35 U.S.C. 154(b) by 823 days.

(21) Appl. No.: 11/997,379

(22) PCT Filed: Jul. 21, 2006

(86) PCT No.: PCT/US2006/028358
§ 371 (c)(1),
(2), (4) Date: Sep. 10, 2008

(87) PCT Pub. No.: WO2007/019016
PCT Pub. Date: Feb. 15, 2007

(65) Prior Publication Data
US 2009/0005793 A1   Jan. 1, 2009

Related U.S. Application Data

(63) Continuation of application No. 11/199,338, filed on Aug. 8, 2005, now abandoned, which is a continuation of application No. 11/199,496, filed on Aug. 8, 2005, now Pat. No. 8,083,754, which is a continuation of application No. 11/199,515, filed on Aug. 8, 2005, now Pat. No. 7,883,517.

(51) Int. Cl.
*A61B 17/04*  (2006.01)
(52) U.S. Cl. ...................................... 606/144
(58) Field of Classification Search .......... 606/139, 606/144, 145, 146, 147, 148, 151
See application file for complete search history.

(56) References Cited

U.S. PATENT DOCUMENTS
312,408  A    2/1885   Wackerhagen
(Continued)

FOREIGN PATENT DOCUMENTS
DE          912619          5/1954
(Continued)

OTHER PUBLICATIONS

U.S. Appl. No. 12/950,338, filed Nov. 19, 2010, Modesitt et al.
(Continued)

*Primary Examiner* — Corrine M McDermott
*Assistant Examiner* — Christina Lauer
(74) *Attorney, Agent, or Firm* — Workman Nydegger; Randy Shen

(57) ABSTRACT

A surgical device of suturing vascular vessels is described, as well as methods for suturing tissue employing the surgical device. In one form the device includes a distal member for insertion into a vascular vessel puncture wound. The distal member contains a suture and needle engaging fitting. At least one needle is advanced through tissue adjacent the puncture wound and into the needle engaging fitting to draw lengths of suture material which can then be used to close the puncture wound. In another form the device includes at least one needle advanceable through tissue and into a needle capture element within a distal end of the surgical device to draw lengths of suture material which can then be used to close various puncture wounds, particularly in vascular tissue. In still another form the device includes at least one needle advanceable through tissue to drawn lengths of suture material which can then be used to close various puncture wounds, particularly in vascular tissue. A foot is pivotal between a non-deployed position and a deployed position where it engages vascular tissue on a distal side of the vessel.

6 Claims, 37 Drawing Sheets

U.S. PATENT DOCUMENTS

| | | |
|---|---|---|
| 597,165 A | 1/1898 | Hall |
| 659,422 A | 10/1900 | Shidler |
| 989,231 A | 4/1911 | Davis |
| 1,574,362 A | 9/1922 | Callahan |
| 1,625,602 A | 4/1927 | Gould et al. |
| 1,940,351 A | 3/1933 | Howard |
| 2,012,776 A | 8/1935 | Roeder |
| 2,131,321 A | 10/1937 | Hart |
| 2,127,903 A | 8/1938 | Bowen |
| 2,371,978 A | 3/1945 | Perham |
| 2,397,823 A | 4/1946 | Walter |
| RE22,857 E | 3/1947 | Ogburn |
| 2,595,086 A | 11/1948 | Larzelere |
| 2,588,589 A | 3/1952 | Tauber |
| 2,646,045 A | 7/1953 | Priestley |
| 2,692,599 A | 10/1954 | Creelman |
| 2,941,489 A | 6/1960 | Fischbein |
| 2,959,172 A | 11/1960 | Held |
| 3,033,156 A | 5/1962 | Verlish |
| 3,104,666 A | 9/1963 | Hale et al. |
| 3,197,102 A | 7/1965 | Bates et al. |
| 3,359,983 A | 12/1967 | Northey |
| 3,413,397 A | 11/1968 | Bierbaum et al. |
| 3,422,181 A | 1/1969 | Chirgwin, Jr. |
| 3,470,875 A | 10/1969 | Johnson |
| 3,485,234 A | 12/1969 | Stevens |
| 3,630,205 A | 12/1971 | Listner |
| 3,653,388 A | 4/1972 | Tenckhoff |
| 3,665,926 A | 5/1972 | Flores |
| 3,776,237 A | 12/1973 | Hill et al. |
| 3,802,438 A | 4/1974 | Wolvek |
| 3,587,115 A | 6/1974 | Shiley |
| 3,820,544 A | 6/1974 | Semm |
| 3,840,017 A | 10/1974 | Violante |
| 3,874,388 A | 4/1975 | King et al. |
| 3,878,848 A | 4/1975 | Hiebert |
| 3,918,455 A | 11/1975 | Coplan |
| 3,926,194 A | 12/1975 | Greenberg et al. |
| 3,939,820 A | 2/1976 | Grayzel |
| 3,985,138 A | 10/1976 | Jarvik |
| 4,018,228 A | 4/1977 | Goosen |
| 4,069,825 A | 1/1978 | Akiyama |
| 4,109,658 A | 8/1978 | Hughes |
| 4,128,100 A | 12/1978 | Wendorff |
| 4,135,623 A | 1/1979 | Thyen |
| 4,161,951 A | 7/1979 | Scanlan, Jr. |
| 4,168,073 A | 9/1979 | LaRue |
| 4,182,339 A | 1/1980 | Hardy, Jr. |
| 4,185,636 A | 1/1980 | Gabbay et al. |
| 4,216,776 A | 8/1980 | Downie et al. |
| 4,217,665 A | 8/1980 | Bex et al. |
| 4,235,177 A | 11/1980 | Arbuckle |
| 4,235,238 A | 11/1980 | Ogiu et al. |
| 4,316,469 A | 2/1982 | Kapitanov |
| 4,317,445 A | 3/1982 | Robinson |
| 4,411,654 A | 10/1983 | Boarini et al. |
| 4,412,832 A | 11/1983 | Kling et al. |
| 4,437,465 A | 3/1984 | Nomoto et al. |
| 4,469,101 A | 9/1984 | Coleman et al. |
| 4,492,229 A | 1/1985 | Grunwald |
| 4,493,323 A | 1/1985 | Albright et al. |
| 4,553,543 A | 11/1985 | Amarasinghe |
| 4,586,614 A | 5/1986 | Ger |
| 4,587,969 A | 5/1986 | Gillis |
| 4,596,559 A | 6/1986 | Fleischhacker |
| 4,610,248 A | 9/1986 | Rosenberg |
| 4,629,450 A | 12/1986 | Suzuki et al. |
| 4,651,733 A | 3/1987 | Mobin-Uddin |
| 4,655,211 A | 4/1987 | Sakamoto et al. |
| 4,702,250 A | 10/1987 | Ovil et al. |
| 4,723,549 A | 2/1988 | Wholey et al. |
| 4,738,666 A | 4/1988 | Fuqua |
| 4,744,364 A | 5/1988 | Kensey |
| 4,748,982 A | 6/1988 | Horzewski et al. |
| 4,782,954 A | 11/1988 | Reynolds |
| 4,803,984 A | 2/1989 | Narayanan et al. |
| 4,836,205 A | 6/1989 | Barrett |
| 4,845,851 A | 7/1989 | Warthen |
| 4,848,341 A | 7/1989 | Ahmad |
| 4,852,568 A | 8/1989 | Kensey |
| 4,890,612 A | 1/1990 | Kensey |
| 4,898,155 A | 2/1990 | Ovil et al. |
| 4,911,164 A | 3/1990 | Roth |
| 4,917,089 A | 4/1990 | Sideris |
| 4,926,860 A | 5/1990 | Stice et al. |
| 4,929,246 A | 5/1990 | Sinofsky |
| 4,935,027 A | 6/1990 | Yoon |
| 4,950,285 A | 8/1990 | Wilk |
| 4,957,498 A | 9/1990 | Caspari et al. |
| 4,966,600 A | 10/1990 | Songer et al. |
| 4,981,149 A | 1/1991 | Yoon et al. |
| 4,983,168 A | 1/1991 | Moorehead |
| 4,984,581 A | 1/1991 | Stice |
| 5,002,563 A | 3/1991 | Pyka et al. |
| 5,009,643 A | 4/1991 | Reich et al. |
| 5,021,059 A | 6/1991 | Kensey et al. |
| 5,037,433 A | 8/1991 | Wilk et al. |
| 5,041,129 A | 8/1991 | Hayhurst et al. |
| 5,047,039 A | 9/1991 | Avant et al. |
| 5,059,201 A | 10/1991 | Asnis |
| 5,061,274 A | 10/1991 | Kensey |
| 5,074,874 A | 12/1991 | Yoon et al. |
| 5,078,721 A | 1/1992 | McKeating |
| 5,080,664 A | 1/1992 | Jain |
| 5,100,419 A | 3/1992 | Ehlers |
| 5,100,422 A | 3/1992 | Berguer et al. |
| 5,100,432 A | 3/1992 | Matsutani |
| 5,108,421 A | 4/1992 | Fowler |
| 5,109,780 A | 5/1992 | Slouf et al. |
| 5,129,882 A | 7/1992 | Weldon et al. |
| 5,129,912 A | 7/1992 | Noda et al. |
| 5,129,913 A | 7/1992 | Ruppert |
| 5,144,961 A | 9/1992 | Chen et al. |
| 5,147,373 A | 9/1992 | Ferzli |
| 5,156,788 A | 10/1992 | Chesterfield et al. |
| 5,160,339 A | 11/1992 | Chen et al. |
| 5,163,946 A | 11/1992 | Li |
| 5,169,041 A | 12/1992 | Tan |
| 5,171,251 A | 12/1992 | Bregen et al. |
| 5,176,691 A | 1/1993 | Pierce |
| 5,178,629 A | 1/1993 | Kammerer |
| 5,192,294 A | 3/1993 | Blake, III |
| 5,192,301 A | 3/1993 | Kamiya et al. |
| 5,192,302 A | 3/1993 | Kensey et al. |
| 5,201,744 A | 4/1993 | Jones |
| 5,207,703 A | 5/1993 | Jain |
| 5,211,650 A | 5/1993 | Noda |
| 5,217,470 A | 6/1993 | Weston |
| 5,217,485 A | 6/1993 | Liv et al. |
| 5,219,358 A | 6/1993 | Bendel et al. |
| 5,222,974 A | 6/1993 | Kensey et al. |
| 5,234,443 A | 8/1993 | Phan et al. |
| 5,234,445 A | 8/1993 | Walker et al. |
| 5,237,985 A | 8/1993 | Hodgson et al. |
| 5,242,427 A | 9/1993 | Bilweis |
| 5,250,033 A | 10/1993 | Evans et al. |
| 5,250,053 A | 10/1993 | Snyder |
| 5,250,054 A | 10/1993 | Li |
| 5,254,105 A | 10/1993 | Haaga |
| 5,254,113 A | 10/1993 | Wilk |
| 5,254,126 A | 10/1993 | Filipi et al. |
| 5,258,003 A | 11/1993 | Ciaglia et al. |
| 5,259,846 A | 11/1993 | Granger et al. |
| 5,275,616 A | 1/1994 | Fowler |
| 5,279,311 A | 1/1994 | Snyder |
| 5,281,236 A | 1/1994 | Bognato et al. |
| 5,281,237 A | 1/1994 | Gimpelson |
| 5,284,485 A | 2/1994 | Kammerer et al. |
| 5,285,945 A | 2/1994 | Brinkerhoff et al. |
| 5,289,963 A | 3/1994 | McGarry et al. |
| 5,290,284 A | 3/1994 | Adair |
| 5,290,297 A | 3/1994 | Phillips |
| 5,290,310 A | 3/1994 | Makower et al. |
| 5,292,309 A | 3/1994 | VanTassel et al. |
| 5,292,327 A | 3/1994 | Dodd et al. |
| 5,292,332 A | 3/1994 | Lee |
| 5,293,881 A | 3/1994 | Green et al. |

| | | | | | |
|---|---|---|---|---|---|
| 5,295,993 A | 3/1994 | Green | 5,527,322 A | 6/1996 | Klein et al. |
| 5,300,085 A | 4/1994 | Yock | D372,310 S | 7/1996 | Hartnett |
| 5,304,184 A | 4/1994 | Hathaway et al. | 5,531,700 A | 7/1996 | Moore et al. |
| 5,304,185 A | 4/1994 | Taylor | 5,536,273 A | 7/1996 | Lehrer |
| 5,306,254 A | 4/1994 | Nash et al. | 5,540,701 A | 7/1996 | Sharkey et al. |
| 5,312,024 A | 5/1994 | Grant et al. | 5,540,703 A | 7/1996 | Barker, Jr. et al. |
| 5,312,423 A | 5/1994 | Rosenbluth et al. | 5,540,704 A | 7/1996 | Gordon et al. |
| 5,318,578 A | 6/1994 | Hasson | 5,545,171 A | 8/1996 | Sharkey et al. |
| 5,320,629 A | 6/1994 | Noda et al. | 5,545,178 A | 8/1996 | Kensey et al. |
| 5,320,632 A | 6/1994 | Heidmueller | 5,545,180 A | 8/1996 | Le et al. |
| 5,330,445 A | 7/1994 | Haaga | 5,549,618 A | 8/1996 | Fleenor et al. |
| 5,330,491 A | 7/1994 | Walker et al. | 5,549,631 A | 8/1996 | Bonutti |
| 5,334,217 A | 8/1994 | Das | 5,554,162 A | 9/1996 | DeLange |
| 5,336,229 A | 8/1994 | Noda | 5,562,684 A | 10/1996 | Kammerer |
| 5,336,230 A | 8/1994 | Leichtling et al. | 5,562,686 A | 10/1996 | Sauer et al. |
| 5,336,231 A | 8/1994 | Adair | 5,562,688 A | 10/1996 | Riza |
| 5,342,369 A | 8/1994 | Harryman, II | 5,562,728 A | 10/1996 | Lazarus et al. |
| 5,354,312 A | 10/1994 | Brinkerhoff et al. | 5,567,435 A | 10/1996 | Hubbell et al. |
| 5,364,407 A | 11/1994 | Poll | 5,569,269 A | 10/1996 | Hart et al. |
| 5,364,408 A | 11/1994 | Gordon | 5,569,271 A | 10/1996 | Hoel |
| 5,368,595 A | 11/1994 | Lewis | 5,571,120 A | 11/1996 | Yoon |
| 5,368,601 A | 11/1994 | Sauer et al. | 5,573,540 A | 11/1996 | Yoon |
| 5,374,275 A | 12/1994 | Bradley et al. | 5,584,842 A | 12/1996 | Fogarty et al. |
| 5,374,278 A | 12/1994 | Chesterfield et al. | 5,591,177 A | 1/1997 | Lehrer |
| 5,376,096 A | 12/1994 | Foster | 5,591,179 A | 1/1997 | Edelstein |
| 5,383,896 A | 1/1995 | Gershony et al. | 5,591,206 A | 1/1997 | Moufarrege |
| 5,383,905 A | 1/1995 | Golds et al. | 5,593,421 A | 1/1997 | Bauer |
| 5,385,569 A | 1/1995 | Swor | 5,603,718 A | 2/1997 | Xu |
| 5,387,221 A | 2/1995 | Bisgaard | 5,607,435 A | 3/1997 | Sachdeva et al. |
| 5,387,227 A | 2/1995 | Grice | 5,609,597 A | 3/1997 | Lehrer |
| 5,391,176 A | 2/1995 | de la Torre | 5,611,794 A | 3/1997 | Sauer et al. |
| 5,391,182 A | 2/1995 | Chin | 5,613,974 A | 3/1997 | Andreas et al. |
| 5,395,332 A | 3/1995 | Ressemann et al. | 5,613,975 A | 3/1997 | Christy |
| 5,395,349 A | 3/1995 | Quiachon et al. | 5,624,446 A | 4/1997 | Harryman, II |
| 5,397,310 A | 3/1995 | Chu et al. | 5,626,588 A | 5/1997 | Sauer et al. |
| 5,397,325 A | 3/1995 | Delia Badia et al. | 5,643,289 A | 7/1997 | Sauer et al. |
| 5,397,326 A | 3/1995 | Mangum | 5,643,295 A | 7/1997 | Yoon |
| 5,403,329 A | 4/1995 | Hinchcliffe | 5,643,318 A | 7/1997 | Tsukernik et al. |
| 5,403,331 A | 4/1995 | Chesterfield et al. | 5,649,959 A | 7/1997 | Hannam et al. |
| 5,403,338 A | 4/1995 | Milo | 5,662,664 A | 9/1997 | Gordon et al. |
| 5,405,352 A | 4/1995 | Weston | 5,669,917 A | 9/1997 | Sauer et al. |
| 5,411,481 A | 5/1995 | Allen et al. | 5,676,689 A | 10/1997 | Kensey et al. |
| 5,413,571 A | 5/1995 | Katsaros et al. | 5,700,273 A | 12/1997 | Buelna et al. |
| 5,417,684 A | 5/1995 | Jackson et al. | 5,707,379 A | 1/1998 | Fleenor et al. |
| 5,417,699 A | 5/1995 | Klein et al. | 5,713,910 A | 2/1998 | Gordon et al. |
| 5,419,765 A | 5/1995 | Weldon et al. | 5,716,369 A | 2/1998 | Riza |
| 5,425,705 A | 6/1995 | Evard et al. | 5,720,574 A | 2/1998 | Barella |
| 5,425,737 A | 6/1995 | Burbank et al. | 5,720,757 A | 2/1998 | Hathaway et al. |
| 5,425,740 A | 6/1995 | Hutchinson, Jr. | 5,722,981 A | 3/1998 | Stevens |
| 5,431,666 A * | 7/1995 | Sauer et al. .................. 606/139 | 5,725,552 A | 3/1998 | Kotula et al. |
| 5,433,700 A | 7/1995 | Peters | 5,728,109 A | 3/1998 | Schulze et al. |
| 5,452,733 A | 9/1995 | Sterman et al. | 5,728,114 A | 3/1998 | Evans et al. |
| 5,454,822 A | 10/1995 | Schob et al. | 5,728,133 A | 3/1998 | Kontos |
| 5,454,834 A | 10/1995 | Boebel et al. | 5,728,151 A | 3/1998 | Garrison et al. |
| 5,458,574 A | 10/1995 | Machold et al. | 5,741,276 A | 4/1998 | Poloyko et al. |
| 5,462,560 A | 10/1995 | Stevens | 5,741,280 A | 4/1998 | Fleenor |
| 5,462,561 A | 10/1995 | Voda | 5,746,755 A | 5/1998 | Wood et al. |
| 5,464,426 A | 11/1995 | Bonutti | 5,749,890 A | 5/1998 | Shaknovich |
| 5,466,241 A | 11/1995 | Leroy et al. | 5,755,727 A | 5/1998 | Kontos |
| 5,470,338 A | 11/1995 | Whitfield et al. | 5,759,188 A | 6/1998 | Yoon |
| 5,474,568 A | 12/1995 | Scott | 5,766,183 A | 6/1998 | Sauer |
| 5,476,469 A | 12/1995 | Hathaway et al. | 5,766,186 A | 6/1998 | Faraz et al. |
| 5,476,470 A | 12/1995 | Fitzgibbons, Jr. | 5,766,217 A | 6/1998 | Christy |
| 5,478,309 A | 12/1995 | Sweezer et al. | 5,769,862 A | 6/1998 | Kammerer et al. |
| 5,478,353 A | 12/1995 | Yoon | 5,779,719 A | 7/1998 | Klein et al. |
| 5,480,407 A | 1/1996 | Wan et al. | 5,782,860 A | 7/1998 | Epstein et al. |
| 5,486,190 A | 1/1996 | Green | 5,782,861 A | 7/1998 | Cragg et al. |
| 5,489,295 A | 2/1996 | Piplani et al. | 5,792,151 A | 8/1998 | Heck et al. |
| 5,496,332 A | 3/1996 | Sierra et al. | 5,792,152 A | 8/1998 | Klein et al. |
| 5,507,744 A | 4/1996 | Tay et al. | 5,797,928 A | 8/1998 | Kogasaka |
| 5,507,755 A | 4/1996 | Gresl et al. | 5,797,929 A | 8/1998 | Andreas et al. |
| 5,507,757 A | 4/1996 | Sauer et al. | 5,799,661 A | 9/1998 | Boyd et al. |
| 5,507,758 A | 4/1996 | Thomason et al. | 5,810,849 A | 9/1998 | Kontos |
| 5,509,902 A | 4/1996 | Raulerson | 5,810,850 A | 9/1998 | Hathaway et al. |
| 5,520,655 A | 5/1996 | Davila et al. | 5,814,069 A | 9/1998 | Schulze et al. |
| 5,520,665 A | 5/1996 | Fleetwood | 5,817,113 A | 10/1998 | Gifford, III et al. |
| 5,520,691 A | 5/1996 | Branch | 5,820,631 A | 10/1998 | Nobles |
| 5,520,702 A | 5/1996 | Sauer et al. | 5,824,010 A | 10/1998 | McDonald |
| 5,527,321 A | 6/1996 | Hinchcliffe | 5,824,111 A | 10/1998 | Schall et al. |

| | | | | | | |
|---|---|---|---|---|---|---|
| 5,830,125 | A | 11/1998 | Scribner et al. | 6,572,629 B2 | 6/2003 | Kalloo et al. |
| 5,836,955 | A | 11/1998 | Buelna et al. | 6,610,072 B1 | 8/2003 | Christy et al. |
| 5,836,956 | A | 11/1998 | Buelna et al. | 6,623,509 B2 | 9/2003 | Ginn |
| 5,846,253 | A | 12/1998 | Buelna et al. | 6,623,510 B2 | 9/2003 | Carley et al. |
| 5,848,714 | A | 12/1998 | Robson et al. | 6,632,237 B2 | 10/2003 | Ben-David et al. |
| 5,855,585 | A | 1/1999 | Kontos | 6,641,592 B1 | 11/2003 | Sauer et al. |
| 5,860,963 | A | 1/1999 | Azam et al. | 6,663,655 B2 | 12/2003 | Ginn et al. |
| 5,860,990 | A | 1/1999 | Nobles et al. | 6,676,685 B2 | 1/2004 | Pedros et al. |
| 5,860,991 | A | 1/1999 | Klein et al. | 6,695,867 B2 | 2/2004 | Ginn et al. |
| 5,861,005 | A | 1/1999 | Kontos | 6,716,228 B2 | 4/2004 | Tal |
| 5,871,490 | A | 2/1999 | Schulze et al. | 6,743,195 B2 | 6/2004 | Zucker |
| 5,871,502 | A | 2/1999 | Suryadevara | 6,743,259 B2 | 6/2004 | Ginn |
| 5,873,876 | A | 2/1999 | Christy | 6,749,621 B2 | 6/2004 | Pantages et al. |
| 5,876,411 | A | 3/1999 | Kontos | 6,749,622 B2 | 6/2004 | McGuckin, Jr. et al. |
| 5,897,487 | A | 4/1999 | Ouchi | 6,837,906 B2 | 1/2005 | Ginn |
| 5,897,564 | A | 4/1999 | Schulze et al. | 6,846,319 B2 | 1/2005 | Ginn et al. |
| 5,902,311 | A | 5/1999 | Andreas et al. | 6,890,343 B2 | 5/2005 | Ginn et al. |
| 5,904,597 | A | 5/1999 | Doi et al. | 6,896,692 B2 | 5/2005 | Ginn et al. |
| 5,904,690 | A | 5/1999 | Middleman et al. | 6,911,034 B2 | 6/2005 | Nobles et al. |
| 5,904,697 | A | 5/1999 | Gifford, III et al. | 6,939,357 B2 | 9/2005 | Navarro et al. |
| 5,906,631 | A | 5/1999 | Imran | 6,964,668 B2 | 11/2005 | Modesitt et al. |
| 5,919,207 | A | 7/1999 | Taheri | 6,969,397 B2 | 11/2005 | Ginn |
| 5,921,994 | A | 7/1999 | Andreas et al. | 7,001,400 B1 | 2/2006 | Modesitt et al. |
| 5,928,266 | A | 7/1999 | Kontos | 7,029,480 B2 | 4/2006 | Klein et al. |
| 5,951,590 | A | 9/1999 | Goldfarb | 7,029,481 B2 | 4/2006 | Burdulis, Jr. et al. |
| 5,954,732 | A | 9/1999 | Hart et al. | 7,048,747 B2 | 5/2006 | Arcia et al. |
| 5,957,936 | A | 9/1999 | Yoon et al. | 7,063,710 B2 | 6/2006 | Takamoto et al. |
| 5,957,937 | A | 9/1999 | Yoon | 7,083,635 B2 | 8/2006 | Ginn |
| 5,957,938 | A | 9/1999 | Zhu et al. | 7,112,225 B2 | 9/2006 | Ginn |
| 5,964,773 | A | 10/1999 | Greenstein | 7,160,309 B2 | 1/2007 | Voss |
| 5,964,782 | A | 10/1999 | Lafontaine et al. | 7,179,266 B2 | 2/2007 | Kontos |
| 5,972,030 | A | 10/1999 | Garrison et al. | 7,229,458 B2 | 6/2007 | Boecker et al. |
| 5,976,161 | A | 11/1999 | Kirsch et al. | 7,235,087 B2 | 6/2007 | Modesitt et al. |
| 5,980,539 | A | 11/1999 | Kontos | 7,316,704 B2 | 1/2008 | Bagaoisan et al. |
| 5,997,555 | A | 12/1999 | Kontos | 7,326,230 B2 | 2/2008 | Ravikumar |
| 6,001,109 | A | 12/1999 | Kontos | 7,331,979 B2 | 2/2008 | Khosravi et al. |
| 6,022,372 | A | 2/2000 | Kontos | 7,335,220 B2 | 2/2008 | Khosravi et al. |
| 6,024,747 | A | 2/2000 | Kontos | 7,361,183 B2 | 4/2008 | Ginn |
| 6,036,699 | A | 3/2000 | Andreas et al. | 7,361,185 B2 | 4/2008 | O'Malley et al. |
| 6,042,601 | A | 3/2000 | Smith | 7,377,927 B2 | 5/2008 | Burdulis, Jr. et al. |
| 6,048,351 | A | 4/2000 | Gordon et al. | 7,390,328 B2 | 6/2008 | Modesitt |
| 6,048,354 | A | 4/2000 | Lawrence | 7,393,363 B2 | 7/2008 | Ginn |
| 6,048,357 | A | 4/2000 | Kontos | 7,442,198 B2 * | 10/2008 | Gellman et al. ............. 606/144 |
| 6,068,603 | A | 5/2000 | Suzuki | 7,445,626 B2 | 11/2008 | Songer et al. |
| 6,077,276 | A * | 6/2000 | Kontos .................. 606/144 | 7,449,024 B2 | 11/2008 | Stafford |
| 6,077,279 | A | 6/2000 | Kontos | 7,462,188 B2 | 12/2008 | McIntosh |
| 6,117,144 | A | 9/2000 | Nobles et al. | 7,753,923 B2 | 7/2010 | St. Goar et al. |
| 6,117,145 | A | 9/2000 | Wood et al. | 7,837,696 B2 | 11/2010 | Modesitt et al. |
| 6,126,675 | A | 10/2000 | Shchervinsky et al. | 7,842,047 B2 | 11/2010 | Modesitt et al. |
| 6,132,439 | A | 10/2000 | Kontos | 7,842,048 B2 | 11/2010 | Ma |
| 6,132,440 | A | 10/2000 | Hathaway et al. | 7,842,049 B2 | 11/2010 | Voss |
| 6,136,010 | A | 10/2000 | Modesitt et al. | 7,846,170 B2 | 12/2010 | Modesitt et al. |
| 6,139,556 | A | 10/2000 | Kontos | 7,850,701 B2 | 12/2010 | Modesitt |
| 6,152,936 | A | 11/2000 | Christy et al. | 7,883,517 B2 | 2/2011 | Pantages et al. |
| 6,165,183 | A | 12/2000 | Kuehn et al. | 2001/0046518 A1 | 11/2001 | Sawhney |
| 6,165,204 | A | 12/2000 | Levinson et al. | 2002/0045908 A1 | 4/2002 | Nobles et al. |
| 6,190,396 | B1 | 2/2001 | Whitin et al. | 2002/0095164 A1 | 7/2002 | Andreas et al. |
| 6,197,042 | B1 | 3/2001 | Ginn et al. | 2002/0099389 A1 | 7/2002 | Michler et al. |
| 6,206,893 | B1 | 3/2001 | Klein et al. | 2002/0106409 A1 | 8/2002 | Sawhney et al. |
| 6,206,895 | B1 | 3/2001 | Levinson et al. | 2002/0177876 A1 | 11/2002 | Roby et al. |
| 6,245,079 | B1 | 6/2001 | Nobles et al. | 2003/0093093 A1 | 5/2003 | Modesitt et al. |
| 6,248,124 | B1 | 6/2001 | Pedros et al. | 2003/0195529 A1 | 10/2003 | Takamoto et al. |
| 6,296,657 | B1 | 10/2001 | Brucker | 2004/0009205 A1 | 1/2004 | Sawhney |
| 6,348,059 | B1 | 2/2002 | Hathaway et al. | 2004/0092964 A1 | 5/2004 | Modesitt et al. |
| 6,355,050 | B1 | 3/2002 | Andreas et al. | 2004/0093027 A1 | 5/2004 | Fabisiak et al. |
| 6,358,258 | B1 | 3/2002 | Arcia et al. | 2004/0097978 A1 | 5/2004 | Modesitt et al. |
| 6,395,015 | B1 | 5/2002 | Borst et al. | 2004/0127940 A1 | 7/2004 | Ginn et al. |
| 6,428,472 | B1 | 8/2002 | Haas | 2004/0143290 A1 | 7/2004 | Brightbill |
| 6,428,549 | B1 | 8/2002 | Kontos | 2004/0158127 A1 | 8/2004 | Okada |
| 6,436,109 | B1 | 8/2002 | Kontos | 2004/0158287 A1 | 8/2004 | Cragg et al. |
| 6,443,963 | B1 | 9/2002 | Baldwin et al. | 2004/0167511 A1 | 8/2004 | Buehlmann et al. |
| 6,451,031 | B1 | 9/2002 | Kontos | 2004/0181238 A1 | 9/2004 | Zarbatany et al. |
| 6,511,489 | B2 | 1/2003 | Field et al. | 2004/0186487 A1 | 9/2004 | Klein et al. |
| 6,517,553 | B2 | 2/2003 | Klein et al. | 2004/0191277 A1 | 9/2004 | Sawhney et al. |
| 6,533,812 | B2 | 3/2003 | Swanson et al. | 2004/0210251 A1* | 10/2004 | Kontos .................. 606/224 |
| 6,551,330 | B1 * | 4/2003 | Bain et al. ............ 606/144 | 2004/0215232 A1 | 10/2004 | Belhe et al. |
| 6,558,399 | B1 | 5/2003 | Isbell et al. | 2004/0225301 A1 | 11/2004 | Roop et al. |
| 6,562,052 | B2 | 5/2003 | Nobles et al. | 2004/0267193 A1 | 12/2004 | Bagaoisan et al. |
| 6,569,185 | B2 | 5/2003 | Ungs | 2004/0267308 A1 | 12/2004 | Bagaoisan et al. |

| | | | | | | |
|---|---|---|---|---|---|---|
| 2005/0059982 A1 | 3/2005 | Zung et al. | | WO | WO 97/00046 | 1/1997 |
| 2005/0070923 A1 | 3/2005 | McIntosh | | WO | WO 97/03613 | 2/1997 |
| 2005/0075665 A1 | 4/2005 | Brenzel et al. | | WO | WO 97/07745 | 3/1997 |
| 2005/0085851 A1 | 4/2005 | Fiehler et al. | | WO | WO 97/10764 | 3/1997 |
| 2005/0085854 A1 | 4/2005 | Ginn | | WO | WO 97/13461 | 4/1997 |
| 2005/0085855 A1 | 4/2005 | Forsberg | | WO | WO 97/17901 | 5/1997 |
| 2005/0121042 A1 | 6/2005 | Belhe et al. | | WO | WO 97/20505 | 6/1997 |
| 2005/0149117 A1 | 7/2005 | Khosravi et al. | | WO | WO 97/27897 | 8/1997 |
| 2005/0177189 A1 | 8/2005 | Ginn et al. | | WO | WO 98/04195 | 2/1998 |
| 2005/0222614 A1 | 10/2005 | Ginn et al. | | WO | WO 98/42262 | 10/1998 |
| 2005/0245876 A1 | 11/2005 | Khosravi et al. | | WO | WO 99/47049 | 9/1999 |
| 2005/0267528 A1 | 12/2005 | Ginn et al. | | WO | WO 00/12013 | 3/2000 |
| 2005/0273137 A1 | 12/2005 | Ginn | | WO | WO 00/51498 | 9/2000 |
| 2006/0034930 A1 | 2/2006 | Khosravi et al. | | WO | WO 00/69342 | 11/2000 |
| 2006/0047313 A1 | 3/2006 | Khanna et al. | | WO | WO 01/19259 | 3/2001 |
| 2006/0079914 A1 | 4/2006 | Modesitt et al. | | WO | WO 01/35833 | 5/2001 |
| 2006/0100664 A1 | 5/2006 | Pai et al. | | WO | WO 02/36021 | 5/2002 |
| 2006/0167477 A1 | 7/2006 | Arcia et al. | | WO | WO 02/062234 | 8/2002 |
| 2006/0173469 A1 | 8/2006 | Klein | | WO | WO 03/003925 | 1/2003 |
| 2006/0253037 A1 | 11/2006 | Ginn et al. | | WO | WO 03/094748 | 11/2003 |
| 2006/0253072 A1 | 11/2006 | Pai et al. | | WO | WO 03/099134 | 12/2003 |
| 2007/0032798 A1 | 2/2007 | Pantages et al. | | WO | WO 2005/000126 | 1/2005 |
| 2007/0032801 A1 | 2/2007 | Pantages et al. | | WO | WO 2005/023119 | 3/2005 |
| 2007/0060950 A1 | 3/2007 | Khosravi et al. | | WO | WO 2005/025430 | 3/2005 |
| 2007/0123817 A1 | 5/2007 | Khosravi et al. | | WO | WO 2005/030060 | 4/2005 |
| 2007/0276410 A1 | 11/2007 | McIntosh | | WO | WO 2005/041782 | 5/2005 |
| 2007/0282354 A1 | 12/2007 | McIntosh | | WO | WO 2005/063129 | 7/2005 |
| 2008/0009794 A1 | 1/2008 | Bagaoisan et al. | | WO | WO 2005/065549 | 7/2005 |
| 2008/0065151 A1 | 3/2008 | Ginn | | WO | WO 2005/092204 | 10/2005 |
| 2008/0065152 A1 | 3/2008 | Carley | | WO | WO 2005/112782 | 12/2005 |
| 2008/0287967 A1 | 11/2008 | Andreas et al. | | WO | WO 2006/026116 | 3/2006 |
| 2008/0319458 A1 | 12/2008 | Reynolds | | WO | WO 2006/052611 | 5/2006 |
| 2009/0036906 A1 | 2/2009 | Stafford | | WO | WO 2006/052612 | 5/2006 |
| 2009/0048615 A1 | 2/2009 | McIntosh | | WO | WO 2006/078578 | 7/2006 |
| 2009/0088779 A1 | 4/2009 | Zung et al. | | WO | WO 2006/115901 | 11/2006 |
| 2009/0157105 A1 | 6/2009 | Zung et al. | | WO | WO 2006/115904 | 11/2006 |
| | | | | WO | WO 2006/118877 | 11/2006 |
| FOREIGN PATENT DOCUMENTS | | | | WO | WO 2007/019016 | 2/2007 |
| DE | 4210724 | 7/1993 | | WO | WO 2007/081836 | 7/2007 |
| DE | 9217932 | 7/1993 | | | | |
| DE | 4220283 | 12/1993 | | | | |
| DE | 10211360 | 10/2003 | | | | |
| EP | 0 140 557 | 5/1985 | | | | |
| EP | 0 207 545 | 1/1987 | | | | |
| EP | 0 474 887 | 3/1992 | | | | |
| EP | 0 478 358 | 4/1992 | | | | |
| EP | 0 478 887 | 4/1992 | | | | |
| EP | 0 542 126 | 5/1993 | | | | |
| EP | 0 568 098 | 11/1993 | | | | |
| EP | 0 589 409 | 3/1994 | | | | |
| EP | 0 624 343 | 11/1994 | | | | |
| EP | 0 669 101 | 8/1995 | | | | |
| EP | 0 669 102 | 8/1995 | | | | |
| EP | 0 669 103 | 8/1995 | | | | |
| EP | 0 684 012 | 11/1995 | | | | |
| EP | 0 812 571 | 3/1997 | | | | |
| EP | 0 941 698 | 9/1999 | | | | |
| FR | 1059544 | 3/1954 | | | | |
| FR | 2768324 | 3/1999 | | | | |
| JP | 51143386 | 11/1976 | | | | |
| JP | 5220794 | 2/1977 | | | | |
| JP | 2119866 | 5/1990 | | | | |
| JP | 542161 | 2/1993 | | | | |
| SU | 820810 | 4/1981 | | | | |
| SU | 993922 | 2/1983 | | | | |
| SU | 1093329 | 5/1984 | | | | |
| SU | 1174036 | 8/1985 | | | | |
| SU | 1544383 | 2/1990 | | | | |
| SU | 1648400 | 5/1991 | | | | |
| WO | WO 85/03858 | 9/1985 | | | | |
| WO | WO 94/05213 | 3/1994 | | | | |
| WO | WO 94/13211 | 6/1994 | | | | |
| WO | WO 94/27503 | 12/1994 | | | | |
| WO | WO 94/28801 | 12/1994 | | | | |
| WO | WO 95/05121 | 2/1995 | | | | |
| WO | WO 95/13021 | 5/1995 | | | | |
| WO | WO 95/25468 | 9/1995 | | | | |
| WO | WO 95/35065 | 12/1995 | | | | |
| WO | WO 96/09006 | 3/1996 | | | | |

OTHER PUBLICATIONS

U.S. Appl. No. 12/955,848, filed Nov. 29, 2010, Modesitt et al.
U.S. Appl. No. 12/955,863, filed Nov. 29, 2010, Ma.
U.S. Appl. No. 12/955,869, filed Nov. 29, 2010, Voss.
U.S. Appl. No. 12/961,239, filed Dec. 6, 2010, Modesitt et al.
U.S. Appl. No. 12/966,961, filed Dec. 13, 2010, Modesitt et al.
U.S. Appl. No. 13/022,050, filed Feb. 7, 2011, Pantages et al.
U.S. Appl. No. 60/506,536, filed Sep. 26, 2003, McIntosh.
U.S. Appl. No. 60/540,811, filed Jan. 30, 2004, McIntosh.
U.S. Appl. No. 60/946,063, filed Jun. 25, 2007, Reynolds.
U.S. Appl. No. 90/006,469, filed Nov. 29, 2002, Modesitt et al.
Cardiac Catheterization and Angiography, 3rd Ed., Lea N ad Febiger, Philadelphia, pp. 1-49, 52-247, 1986.
Cardio-Thoracic Systems Prospectus dated Mar. 20, 1996.
Datascope Corporation, Montvale, NJ, Nov. 1991; 1 PG, American Heart Assoc. Meeting, Anaheim.
Elgiloy Brochure, Jun. 23, 1959; Elgin National Watch Co., Elgin, IL.
Kensey Nash Corporation, Exton, PA, "The Hemostatic Puncture Closure Device", retrieved Oct. 23, 2007, 2 pages.
Laurus Medical Corporation, "Endoscopic Suturing Made Simple," The Laurus ND-2600 Needle Driver, Irvine, CA., Oct. 1994, 1 page.
Marshall, A.C. & Lock, J.E.; "Structural and compliant anatomy of the patent foramen ovale in patients undergoing transcatheter closure", Am. Heart Journ., 140(2):303-307, Aug. 2000.
Nakamura, S. et al., Techniques for Palmaz-Schatz Stent Deployment in Lesions With a Large Side Branch, Catheterization and Cardiovascular Diagnosis, 34: 353-361, 1995.
Product Brochure, "SuperStitch—Closure Made SimpleTM", Sutura, Inc. (2003).
Product Brochure, Laurus Medical Corporation, Irvine, CA "The Laurus In-Line Endoscopic Suturing Device" (Oct. 1994) 1 page.
Rema-Medizintechnik GmbH, Product Brochure entitled "REMA," Apr. 2001, 7 pages.
Serruys, PW et al., A Comparision of Balloon-Expandable-Stent Implantaion With Balloon Angioplasty in Patients With Coronary Artery Disease, New England Journal of Medicine, 331:489-495, 1994.

Taber's Cyclopedic Medical Dictionary, 18th Ed., p. 747, Feb. 1997.
U.S. Appl. No. 07/989,611, mailed May 12, 1993, Office Action.
U.S. Appl. No. 07/989,611, mailed Aug. 1, 1994, Office Action.
U.S. Appl. No. 07/989,611, mailed Nov. 3, 1994, Notice of Allowance.
U.S. Appl. No. 08/148,809, mailed Sep. 16, 1994, Office Action.
U.S. Appl. No. 08/148,809, mailed May 30, 1995, Office Action.
U.S. Appl. No. 08/148,809, mailed Dec. 15, 1995, Notice of Allowance.
U.S. Appl. No. 08/252,124, mailed Jun. 5, 1995, Office Action.
U.S. Appl. No. 08/252,124, mailed Jan. 5, 1996, Office Action.
U.S. Appl. No. 08/252,124, mailed May 22, 1996, Notice of Allowance.
U.S. Appl. No. 08/259,410, mailed Feb. 2, 1995, Office Action.
U.S. Appl. No. 08/259,410, mailed Jun. 1, 1995, Office Action.
U.S. Appl. No. 08/259,410, mailed Feb. 6, 1998, Notice of Allowance.
U.S. Appl. No. 08/638,076, mailed Jan. 21, 1997, Office Action.
U.S. Appl. No. 08/638,076, mailed Oct. 17, 1997, Notice of Allowance.
U.S. Appl. No. 08/824,031, mailed Mar. 16, 1998, Office Action.
U.S. Appl. No. 08/824,031, mailed Sep. 14, 1998, Office Action.
U.S. Appl. No. 08/824,031, mailed Apr. 13, 1999, Office Action.
U.S. Appl. No. 08/824,031, mailed Jul. 15, 1999, Notice of Allowance.
U.S. Appl. No. 08/883,246, mailed Jul. 23, 1998, Office Action.
U.S. Appl. No. 08/883,246, mailed Apr. 12, 1999, Office Action.
U.S. Appl. No. 08/883,246, mailed Oct. 13, 1999, Office Action.
U.S. Appl. No. 08/883,246, mailed Oct. 23, 2000, Office Action.
U.S. Appl. No. 08/883,246, mailed Jul. 11, 2001, Office Action.
U.S. Appl. No. 08/883,246, mailed Sep. 11, 2001, Notice of Allowance.
U.S. Appl. No. 09/057,108, mailed Jul. 10, 2000, Office Action.
U.S. Appl. No. 09/057,108, mailed Oct. 25, 2000, Notice of Allowance.
U.S. Appl. No. 09/262,402, mailed Mar. 29, 2000, Office Action.
U.S. Appl. No. 09/262,402, mailed May 30, 2000, Notice of Allowance.
U.S. Appl. No. 09/395,901, mailed Jun. 27, 2000, Office Action.
U.S. Appl. No. 09/395,901, mailed Nov. 6, 2000, Office Action.
U.S. Appl. No. 09/395,901, mailed Apr. 20, 2001, Notice of Allowance.
U.S. Appl. No. 09/395,901, mailed Sep. 10, 2001, Notice of Allowance.
U.S. Appl. No. 09/610,099, mailed Jul. 11, 2002, Office Action.
U.S. Appl. No. 09/610,099, mailed Dec. 24, 2002, Notice of Allowance.
U.S. Appl. No. 09/651,344, mailed Feb. 28, 2003, Office Action.
U.S. Appl. No. 09/651,344, mailed Nov. 7, 2003, Office Action.
U.S. Appl. No. 09/651,344, mailed Apr. 20, 2004, Notice of Allowance.
U.S. Appl. No. 09/707,746, mailed Feb. 16, 2005, Office Action.
U.S. Appl. No. 09/707,746, mailed Jul. 7, 2005, Office Action.
U.S. Appl. No. 09/707,746, mailed Nov. 15, 2005, Notice of Allowance.
U.S. Appl. No. 09/769,109, mailed Oct. 23, 2001, Office Action.
U.S. Appl. No. 09/769,109, mailed Jun. 17, 2002, Office Action.
U.S. Appl. No. 09/769,109, mailed Sep. 9, 2002, Notice of Allowance.
U.S. Appl. No. 09/988,541, mailed Mar. 17, 2004, Office Action.
U.S. Appl. No. 09/988,541, mailed Feb. 28, 2005, Office Action.
U.S. Appl. No. 09/988,541, mailed May 25, 2005, Office Action.
U.S. Appl. No. 09/988,541, mailed Aug. 24, 2005, Office Action.
U.S. Appl. No. 09/988,541, mailed Nov. 8, 2005, Office Action.
U.S. Appl. No. 09/988,541, mailed Dec. 13, 2005, Notice of Allowance.
U.S. Appl. No. 10/033,689, mailed Sep. 30, 2003, Office Action.
U.S. Appl. No. 10/152,272, mailed Jan. 24, 2005, Office Action.
U.S. Appl. No. 10/152,272, mailed May 13, 2005, Notice of Allowance.
U.S. Appl. No. 10/335,065, mailed Mar. 17, 2005, Office Action.
U.S. Appl. No. 10/335,065, mailed Jun. 10, 2005, Office Action.
U.S. Appl. No. 10/335,065, mailed Nov. 17, 2005, Notice of Allowance.
U.S. Appl. No. 10/335,147, mailed Dec. 13, 2005, Office Action.
U.S. Appl. No. 10/335,147, mailed Apr. 17, 2006, Office Action.
U.S. Appl. No. 10/335,147, mailed Oct. 4, 2006, Notice of Allowance.
U.S. Appl. No. 10/357,984, mailed Jan. 9, 2006, Office Action.
U.S. Appl. No. 10/357,984, mailed Mar. 16, 2006, Office Action.
U.S. Appl. No. 10/357,984, mailed Sep. 28, 2006, Office Action.
U.S. Appl. No. 10/357,984, Mar. 23, 2007, Office Action.
U.S. Appl. No. 10/357,984, mailed Nov. 14, 2007, Office Action.
U.S. Appl. No. 10/652,182, mailed Aug. 9, 2006, Office Action.
U.S. Appl. No. 10/652,182, mailed Feb. 22, 2007, Notice of Allowance.
U.S. Appl. No. 10/660,288, mailed Nov. 15, 2005, Office Action.
U.S. Appl. No. 10/660,288, mailed Mar. 9, 2006, Office Action.
U.S. Appl. No. 10/660,288, mailed Aug. 24, 2006, Office Action.
U.S. Appl. No. 10/660,288, mailed Feb. 1, 2007, Office Action.
U.S. Appl. No. 10/660,288, mailed Jun. 28, 2007, Office Action.
U.S. Appl. No. 10/660,288, mailed Apr. 29, 2009, Office Action.
U.S. Appl. No. 10/660,288, mailed Aug. 3, 2009, Office Action.
U.S. Appl. No. 10/660,288, mailed Mar. 30, 2010, Office Action.
U.S. Appl. No. 10/729,541, mailed Dec. 12, 2006, Office Action.
U.S. Appl. No. 10/729,541, mailed Jun. 18, 2007, Office Action.
U.S. Appl. No. 10/729,541, mailed Jan. 8, 2008, Office Action.
U.S. Appl. No. 10/729,541, mailed Sep. 23, 2008, Office Action.
U.S. Appl. No. 10/729,541, mailed May 1, 2009, Office Action.
U.S. Appl. No. 10/729,541, mailed Nov. 16, 2009, Notice of Allowance.
U.S. Appl. No. 10/729,541, mailed Mar. 25, 2010, Notice of Allowance.
U.S. Appl. No. 10/729,541, mailed Jul. 12, 2010, Notice of Allowance.
U.S. Appl. No. 10/729,541, mailed Nov. 3, 2010, Issue Notification.
U.S. Appl. No. 10/737,668, mailed Nov. 2, 2005, Office Action.
U.S. Appl. No. 10/737,668, mailed Feb. 16, 2006, Office Action.
U.S. Appl. No. 10/737,668, mailed Oct. 19, 2006, Office Action.
U.S. Appl. No. 10/737,668, mailed Jun. 7, 2007, Office Action.
U.S. Appl. No. 10/737,668, mailed Nov. 28, 2007, Office Action.
U.S. Appl. No. 10/737,668, mailed Jun. 26, 2008, Notice of Allowance.
U.S. Appl. No. 10/742,406, mailed Mar. 23, 2007, Office Action.
U.S. Appl. No. 10/742,406, mailed Sep. 10, 2007, Notice of Allowance.
U.S. Appl. No. 10/742,406, mailed Jan. 11, 2008, Notice of Allowance.
U.S. Appl. No. 10/746,210, mailed Apr. 5, 2007, Office Action.
U.S. Appl. No. 10/746,210, mailed Aug. 21, 2007, Office Action.
U.S. Appl. No. 10/746,210, mailed Jul. 9, 2008, Notice of Allowance.
U.S. Appl. No. 10/813,449, mailed Sep. 5, 2006, Office Action.
U.S. Appl. No. 10/813,449, mailed Jul. 16, 2007, Office Action.
U.S. Appl. No. 10/813,449, mailed Jan. 25, 2008, Office Action.
U.S. Appl. No. 10/813,449, mailed Aug. 14, 2008, Office Action.
U.S. Appl. No. 10/813,449, mailed Sep. 15, 2008, Office Action.
U.S. Appl. No. 10/813,449, mailed Feb. 3, 2009, Office Action.
U.S. Appl. No. 10/813,449, mailed Aug. 28, 2009, Office Action.
U.S. Appl. No. 10/813,449, mailed May 27, 2010, Office Action.
U.S. Appl. No. 10/909,531, mailed Apr. 4, 2007, Office Action.
U.S. Appl. No. 10/909,531, mailed Dec. 26, 2007, Office Action.
U.S. Appl. No. 10/909,531, mailed Jun. 13, 2008, Office Action.
U.S. Appl. No. 10/909,531, mailed Feb. 9, 2009, Office Action.
U.S. Appl. No. 10/909,531, mailed Sep. 16, 2009, Office Action.
U.S. Appl. No. 10/909,531, mailed Apr. 29, 2010, Notice of Allowance.
U.S. Appl. No. 10/909,531, mailed Aug. 20, 2010, Notice of Allowance.
U.S. Appl. No. 10/909,531, mailed Nov. 23, 2010, Issue Notification.
U.S. Appl. No. 10/948,445, mailed Jul. 11, 2007, Office Action.
U.S. Appl. No. 11/199,338, mailed Apr. 23, 2008, Office Action.
U.S. Appl. No. 11/199,338, mailed Jan. 6, 2009, Office Action.
U.S. Appl. No. 11/199,496, mailed Apr. 1, 2009, Office Action.
U.S. Appl. No. 11/199,496, mailed Aug. 21, 2009, Office Action.
U.S. Appl. No. 11/199,496, mailed Apr. 23, 2010, Office Action.

U.S. Appl. No. 11/199,515, mailed Aug. 20, 2008, Office Action.
U.S. Appl. No. 11/199,515, mailed Nov. 13, 2008, Office Action.
U.S. Appl. No. 11/199,515, mailed Jun. 10, 2009, Office Action.
U.S. Appl. No. 11/199,515, mailed Dec. 24, 2009, Notice of Allowance.
U.S. Appl. No. 11/199,515, mailed Apr. 2, 2010, Notice of Allowance.
U.S. Appl. No. 11/199,515, mailed Aug. 2, 2010, Notice of Allowance.
U.S. Appl. No. 11/273,107, mailed Jun. 14, 2007, Office Action.
U.S. Appl. No. 11/273,107, mailed Jan. 18, 2008, Office Action.
U.S. Appl. No. 11/273,107, mailed Sep. 5, 2008, Office Action.
U.S. Appl. No. 11/273,107, mailed Apr. 9, 2009, Office Action.
U.S. Appl. No. 11/273,107, mailed Oct. 28, 2009, Office Action.
U.S. Appl. No. 11/273,107, mailed Jun. 2, 2010, Office Action.
U.S. Appl. No. 11/273,107, mailed Oct. 27, 2010, Office Action.
U.S. Appl. No. 11/363,005, mailed Jun. 22, 2007, Office Action.
U.S. Appl. No. 11/363,005, mailed Dec. 14, 2007, Office Action.
U.S. Appl. No. 11/363,005, mailed Apr. 17, 2008, Office Action.
U.S. Appl. No. 11/363,005, mailed Dec. 23, 2008, Office Action.
U.S. Appl. No. 11/363,005, mailed Jul. 10, 2009, Notice of Allowance.
U.S. Appl. No. 11/363,005, mailed Jan. 14, 2010, Notice of Allowance.
U.S. Appl. No. 11/363,005, mailed Jul. 23, 2010, Notice of Allowance.
U.S. Appl. No. 11/363,005, mailed Nov. 10, 2010, Issue Notification.
U.S. Appl. No. 11/389,762, mailed Sep. 20, 2007, Notice of Allowance.
U.S. Appl. No. 11/389,762, mailed Nov. 23, 2007, Notice of Allowance.
U.S. Appl. No. 11/390,937, mailed Sep. 7, 2007, Office Action.
U.S. Appl. No. 11/391,951, mailed Oct. 28, 2008, Office Action.
U.S. Appl. No. 11/391,951, mailed Jan. 30, 2009, Office Action.
U.S. Appl. No. 11/391,951, mailed Aug. 26, 2009, Office Action.
U.S. Appl. No. 11/391,951, mailed Jun. 23, 2010, Office Action.
U.S. Appl. No. 11/465,527, mailed Feb. 3, 2010, Office Action.
U.S. Appl. No. 11/465,527, mailed Jul. 23, 2010, Notice of Allowance.
U.S. Appl. No. 11/465,527, mailed Nov. 10, 2010, Issue Notification.
U.S. Appl. No. 11/552,593, mailed Aug. 21, 2008, Office Action.
U.S. Appl. No. 11/552,593, mailed Feb. 5, 2009, Office Action.
U.S. Appl. No. 11/552,593, mailed Oct. 13, 2009, Notice of Allowance.
U.S. Appl. No. 11/552,593, mailed Mar. 22, 2010, Notice of Allowance.
U.S. Appl. No. 11/552,593, mailed Jul. 22, 2010, Notice of Allowance.
U.S. Appl. No. 11/552,593, mailed Nov. 10, 2010, Issue Notification.
U.S. Appl. No. 11/688,722, mailed Mar. 10, 2010, Office Action.
U.S. Appl. No. 11/688,722, mailed Jul. 29, 2010, Notice of Allowance.
U.S. Appl. No. 11/688,722, mailed Nov. 17, 2010, Issue Notification.
U.S. Appl. No. 11/891,358, mailed Apr. 26, 2010, Office Action.
U.S. Appl. No. 11/891,358, mailed Oct. 19, 2010, Office Action.
U.S. Appl. No. 11/891,513, mailed Apr. 9, 2010, Office Action.
U.S. Appl. No. 11/891,513, mailed Sep. 28, 2010, Office Action.
U.S. Appl. No. 11/960,593, mailed Sep. 14, 2010, Office Action.
U.S. Appl. No. 11/960,593, mailed Nov. 3, 2010, Office Action.
U.S. Appl. No. 12/182,836, mailed Oct. 5, 2010, Office Action.
U.S. Appl. No. 12/257,127, mailed Aug. 30, 2010, Office Action.
U.S. Appl. No. 12/257,127, mailed Dec. 22, 2010, Office Action.
U.S. Appl. No. 12/334,077, mailed Oct. 27, 2010, Office Action.
U.S. Appl. No. 12/334,085, mailed Dec. 23, 2010, Office Action.
U.S. Appl. No. 90/006,469, mailed Nov. 29, 2002, Request for Re-Examination.
U.S. Appl. No. 90/006,469, mailed Sep. 10, 2004, Office Action.
U.S. Appl. No. 90/006,469, mailed Sep. 27, 2005, Notice of Re-Issue.
U.S. Appl. No. 90/006,469, mailed Jun. 27, 2006, Re-Examination Certification.
U.S. Appl. No. 12/182,836, mailed Jun. 23, 2011, Office Action.
U.S. Appl. No. 10/660,288, mailed Mar. 29, 2011, Office Action.
U.S. Appl. No. 11/199,496, mailed Apr. 28, 2011, Office Action.
U.S. Appl. No. 11/960,593, mailed Apr. 28, 2011, Office Action.
U.S. Appl. No. 11/273,107, mailed Jun. 2, 2011, Notice of Allowance.
U.S. Appl. No. 12/950,338, mailed Jun. 15, 201, Office Action.
U.S. Appl. No. 12/334,085, mailed Jan. 9, 2012, Notice of Allowance.
U.S. Appl. No. 12/955,863, mailed Jan. 6, 2012, Office Action.
U.S. Appl. No. 12/961,239, mailed Oct. 12, 2011, Issue Notification.
U.S. Appl. No. 12/247,012, mailed Oct. 13, 2011, Office Action.
U.S. Appl. No. 12/257,127, Jan. 12, 2012, Office Action.
U.S. Appl. No. 11/199,496, mailed Aug. 18, 2011, Notice of Allowance.
U.S. Appl. No. 11/891,358, mailed Aug. 31, 2011, Office Action.
U.S. Appl. No. 11/891,513, mailed Aug. 31, 2011, Office Action.
U.S. Appl. No. 12/257,127, mailed Jul. 6, 2011, Office Action.
U.S. Appl. No. 12/334,077, mailed Jul. 21, 2011, Office Action.
U.S. Appl. No. 12/334,085, mailed Aug. 4, 2011, Office Action.
U.S. Appl. No. 12/961,239, mailed Jul. 26, 2011, Notice of Allowance.
U.S. Appl. No. 12/966,961, mailed Aug. 18, 2011, Notice of Allowance.
U.S. Appl. No. 13/022,050, mailed Jul. 11, 2011, Office Action.
U.S. Appl. No. 10/660,288, mailed Sep. 30, 2011, Notice of Allowance.
U.S. Appl. No. 11/273,107, mailed Sep. 28, 2011, Issue Notification.
U.S. Appl. No. 11/891,358, mailed Nov. 18, 2011, Notice of Allowance.
U.S. Appl. No. 12/955,848, mailed Nov. 15, 2011, Office Action.
U.S. Appl. No. 12/955,869, mailed Oct. 18, 2011, Office Action.
U.S. Appl. No. 11/891,513, mailed Nov. 1, 2011, Notice of Allowance.
U.S. Appl. No. 12/950,338, mailed Nov. 1, 2011, Notice of Allowance.
U.S. Appl. No. 12/966,961, mailed Oct. 26, 2011, Issue Notification.
U.S. Appl. No. 12/955,848, mailed Jun. 30, 2011, Office Action.
U.S. Appl. No. 11/891,513, mailed May 8, 2012, Notice of Allowance.
U.S. Appl. No. 12/955,863, mailed May 15, 2012, Notice of Allowance.
U.S. Appl. No. 13/022,050, mailed Apr. 26, 2012, Office Aciton.
US 5,820,544, 06/1974, Semm (withdrawn)

* cited by examiner

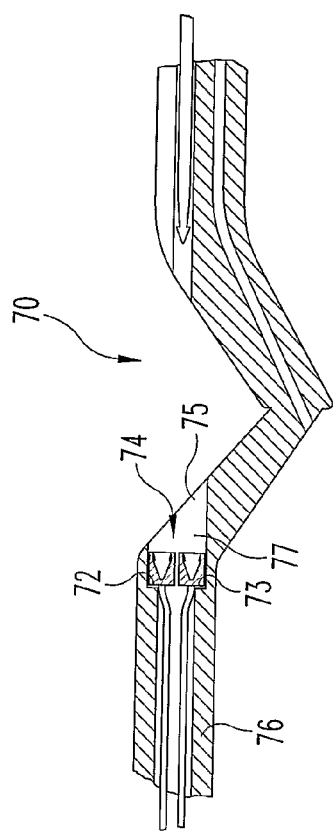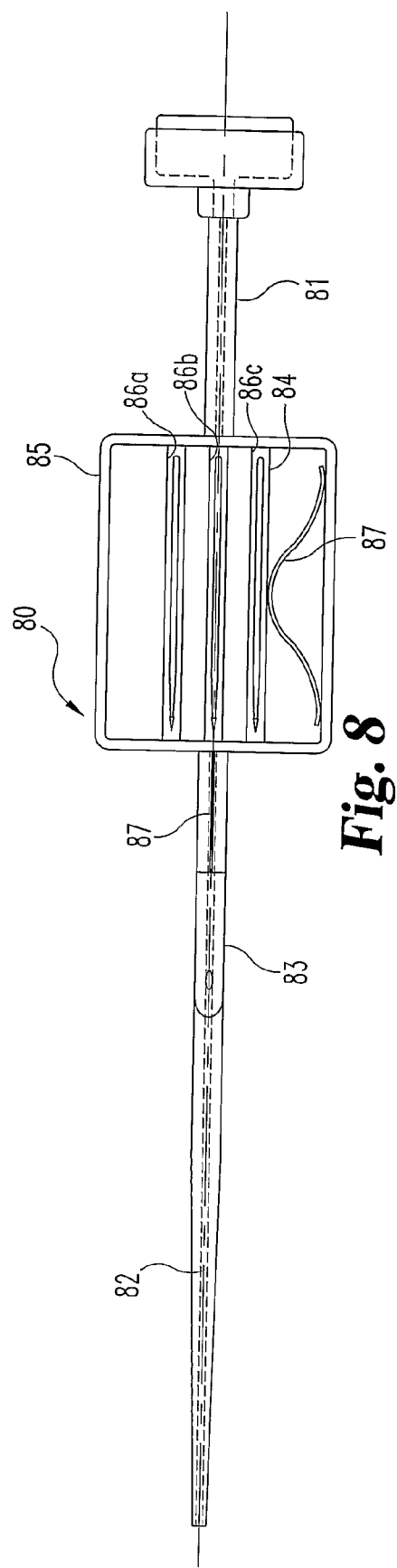

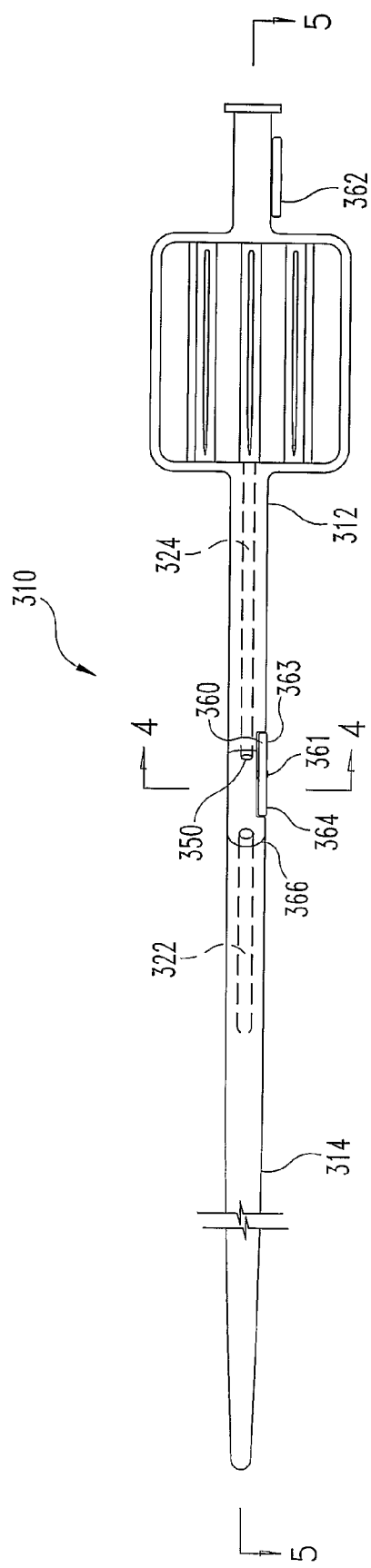
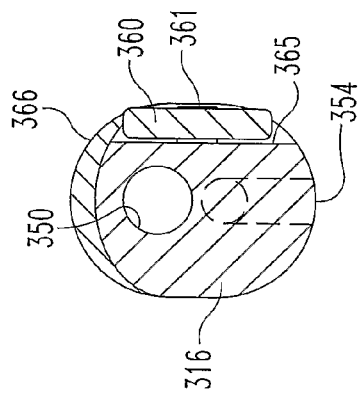
Fig. 39
Fig. 40

VASCULAR SUTURING DEVICE

CROSS-REFERENCE TO RELATED APPLICATIONS

This application is a U.S. Nationalization of PCT Application Number PCT/US2006/028358 entitled "Vascular Suturing Device", filed Jul. 21, 2006, which is a continuation of U.S. patent application Ser. No. 11/199,338, entitled "Vascular Suturing Device", filed Aug. 8, 2005 now abandoned; and of Ser. No. 11/199,496 now U.S. Pat. No. 8,083,754, entitled "Vascular Suturing Device with Needle Capture", filed Aug. 8, 2005; and of U.S. patent application Ser. No. 11/199,515 now U.S. Pat. No. 7,883,517, entitled "Vascular Suturing Device", filed Aug. 8, 2005, each of which is incorporated herein by reference in its entirety.

BACKGROUND OF THE INVENTION

The present invention generally relates to surgical instruments and methods of suturing tissue.

A number of diagnostic and treatment procedures are conducted intravascularly. Typically, a catheter is introduced into the vascular system at a convenient access location and is then guided to the target treatment site. The Seldinger Technique is one of the well-known early examples of this type of procedure which can include catheterization and angioplasty techniques. Procedures such as this require a vascular access. Typically an introducer sheath with or without a guide wire is inserted through a puncture wound in a vessel such as the femoral artery at a location near the groin. A catheter and other instrumentation can then be inserted through the sheath and guided to the targeted treatment site. After the diagnostic and/or treatment procedure has been completed, the puncture wound must be closed. Closing the wound can be difficult because of the substantial bleeding that can occur through an open wound in the vascular vessel. One technique for hemostasis includes applying pressure near or upstream of the puncture site. This approach suffers from many deleterious effects, not the least of which are that it can be time consuming and extremely uncomfortable—even painful—for the patient because the pressure is applied directly on or adjacent to the traumatized site. Frequently anticoagulants are employed for the original diagnostic/treatment procedures. This delays clot formation during the procedure, and this effect lasts through the initial recovery period, lengthening the time during which pressure must be applied to the wound for up to twelve hours or more. During this initial recovery period, it is imperative that the patient remain still, further adding to the patient's discomfort.

Alternatively, the puncture wound can be closed with sutures. This can be extremely difficult because the vascular vessel with the puncture lies underneath the patient's outer skin. Some vascular vessels, notably the femoral artery, appear to be relatively large; however, in practice, even the largest arteries cannot be readily sutured. Therefore, devices have been developed to facilitate subcutaneous suturing of arteries and veins. These devices can extend through the outer tissue to the puncture wound in the vascular vessel. Needles are then deployed from the device to suture the tissue adjacent the puncture wound.

Certain devices are inserted through the wound and initially deploy needles to pierce the tissue in from outside the vascular vessel and continue on into a depository in the portion of the device located within the lumen of the vessel. The suturing device can be removed from the vessel (and the patient) by withdrawing the needles and suture material at the same time. These devices leave an inverted suture path after completion of the closure. The suture material runs from the exterior tissue surrounding the puncture wound back up through the wound itself which is then tied off. Some complications may arise resulting from this type of closure, including oozing, excessive bleeding, and, on rare occasions, knot loosening. It would be preferred to provide a suturing device that allows the suture path to extend across the puncture opening internal of the vessel membrane with the suture knot overlying the exterior of the closed wound.

Furthermore, while the above-described techniques are regularly performed, as with any surgical procedure, they involve considerable risk to patients. These particular procedures entail delicate and intricate procedures. The physical condition of the patient and, importantly, the condition of the patient's vascular system can greatly impact the risks and prognosis. For example, a patient's vascular vessels may be more or less compliant. This can cause further complications making suturing of the puncture wound more difficult. Many current suturing devices cannot accommodate and support non-compliant vascular tissue because the sutures can be misplaced, not attach sufficient tissue, or pull out making wound closure more risky for these patients. Devices which can Support tissue and facilitate correct suture placement would reduce some of the risks attendant with this procedure.

In view of the above background, there remain needs for improved and/or alternative methods and devices for closing vascular opening or punctures. The present invention is addressed to these needs.

SUMMARY OF THE INVENTION

The present invention relates to suturing device and the use thereof. Various aspects of the invention are novel, nonobvious, and provide various advantages. While the actual nature of the invention covered herein can only be determined with reference to the claims appended hereto, certain forms and features, which are characteristic of the preferred embodiments disclosed herein, are described briefly as follows.

In one form, the present invention provides a suturing device for suturing an opening in a vascular vessel. The device comprises a proximal member that can be configured as an elongate body with a needle channel extending at least partway therethrough and sized to receive at least one needle; a distal member configured to be inserted within a lumen of a vascular vessel, where the distal member has a receptacle located therein and a length of suture material with a needle engaging fitting positioned in the receptacle; and an intermediate member disposed between the proximal member and the distal member. In one embodiment, the intermediate member defines a tissue receiving area and has a first opening providing a passageway to the channel and a second opening providing a passageway into the receptacle. In other embodiments, the distal member defines a substantially linear longitudinal axis and the intermediate member can deviate from that longitudinal axis. In other embodiments, the intermediate defines a tissue receiving area that provides a linear needle pathway through the tissue receiving area.

In another form, the present invention provides a suturing device for suturing an opening in a vascular vessel. The suturing device comprises: a proximal member including an elongate body having a needle channel therethrough sized to receive at least one needle and including a needle cartridge slidably mounted thereon configured to contain two or more needles; a distal member configured to be inserted within a lumen of a vascular vessel and having a receptacle located therein and a length of suture material with a needle engaging fitting positioned in the receptacle; an intermediate member disposed between the proximal member and the distal member, where the intermediate member defines a tissue receiving area and has a first opening providing a passageway to the channel and a second opening providing a passageway into the receptacle, and a length of suture material comprising a needle engaging fitting positioned in the receptacle to engage a needle entering from the second opening.

In yet another form, the present invention provides A method of suturing an opening in a vascular vessel, said method comprising: inserting a vascular suturing device through the opening in the vascular vessel, said suturing device comprising a proximal member having a needle channel and a needle therein; a distal member configured to be inserted into the lumen of the vascular vessel, the distal member having a cavity therein and a length of suture material disposed in the cavity; and a connecting member between the proximal and distal members, the connecting member angled or curved to offset the channel and the cavity from the opening in the vascular vessel and having a first opening into the needle channel and a second opening into the cavity; sufficiently advancing the needle through the needle channel to pierce a portion of tissue adjacent the opening in the vessel and extend into the cavity of the distal member; and capturing the suture within the cavity with the needle; and retracting the needle carrying a first portion of the suture back through the tissue and the channel.

In another form, the present invention provides a suturing device for suturing. The suturing device provides particular advantages, for suturing a wall portion of a vascular vessel. The device comprises: a proximal member including an elongate body with a channel sized to receive a needle therein; a distal member comprising a receptacle therein, where the distal member is configured to be inserted into a vascular vessel, and wherein the receptacle is sized to receive at least one needle therein; an intermediate member disposed between the proximal member and distal member, where the intermediate member defines a tissue receiving area and provides a first passageway from the channel to the tissue receiving area and second passageway from the receptacle in the distal member to the tissue receiving area. In preferred embodiments a needle capture element positioned in the receptacle of the distal member. The needle capture element is configured to secure a needle inserted into the receptacle.

In another form, the present invention provides a method of suturing vascular tissue adjacent an opening in a vascular vessel. The method uses a suturing device which can be inserted through the opening in the vascular vessel. The device comprises: a proximal member with a needle channel formed therein; a distal member configured to be inserted into the lumen of the vascular vessel, where the distal member has a receptacle that includes a needle capture element and which is sized to receive at least one needle; and an intermediate member disposed between the proximal member and the distal member. The intermediate member defines a tissue receiving area and is configured to provide a linear needle pathway between the channel and the receptacle. A needle is advanced through or along the needle channel to pierce the vascular tissue drawing a portion of the length of suture material through the vascular tissue. The needle is further advanced so that a portion of the needle engages with the needle capture element in the receptacle. Preferable the needle capture element prevents and in adverting dislodging of the needle from the receptacle during the surgical procedure. However, the same needle capture element also allows the surgeon to remove the needle when and if desired.

In another form the present invention provides a suturing device for suturing an opening in a vascular vessel. The device comprises: a proximal member including an elongate body with a needle channel therethrough sized to receive at least one needle; a distal member configured to be inserted within a lumen of a vascular vessel, where the distal member has a receptacle to receive one or more of the needles after located they have passed through the tissue; an intermediate member disposed between the proximal member and the distal member and defining a tissue receiving area with a first opening providing a passageway to the channel and a second opening providing a passageway into the receptacle; and a foot pivotally mounted on the intermediate member to engage with a portion of the tissue.

In another form the present invention provides a method of suturing an opening in a vascular vessel. The method comprises: inserting a suturing device through the opening in the vascular vessel wherein the suturing device comprises a proximal member having a needle channel therein; a distal member configured to be inserted into the lumen of the vascular vessel with a receptacle therein sized to receive at least one needle; an intermediate member disposed between the proximal and distal member and having a first opening providing a passageway way to the needle channel and a second opening providing a second passageway into the receptacle and wherein the intermediate member is angled or curved to offset the needle channel and the receptacle from the opening in the vascular vessel; and a foot pivotally mounted on the intermediate member. The method also comprises: deploying the foot to contact vascular tissue adjacent the opening; and advancing a first needle through the needle channel to pierce a portion of vascular tissue at a first suture site adjacent the opening in the vascular vessel and into the receptacle in the distal member. Additionally the device can be relocated within the vessel to advance a second needle and length of suture material through the tissue. The ends of the two lengths of suture material can be pulled taut to close the wound or opening the vessel. A surgical knot or other knot replacement technology can be utilized to complete the wound closure.

BRIEF DESCRIPTION OF THE DRAWINGS

FIG. 1A is an illustration of suture material suitable for use in the suturing device of FIG. 1 accordance with the present invention.

FIG. 7 is an enlarged cross-sectional view of an alternative embodiment of a connector member with suture material and two laterally disposed ferrules in accordance with the present invention.

FIG. 8 is a plan view of an alternative embodiment of a suturing device with a needle cartridge for use in accordance with the present invention.

FIG. 39 is a plan view of the suturing device illustrated in FIG. 37.

FIG. 40 is a cross-section view taken on line 40-40 of the suturing device illustrated in FIG. 39.

DETAILED DESCRIPTION OF THE INVENTION

Figure 1:
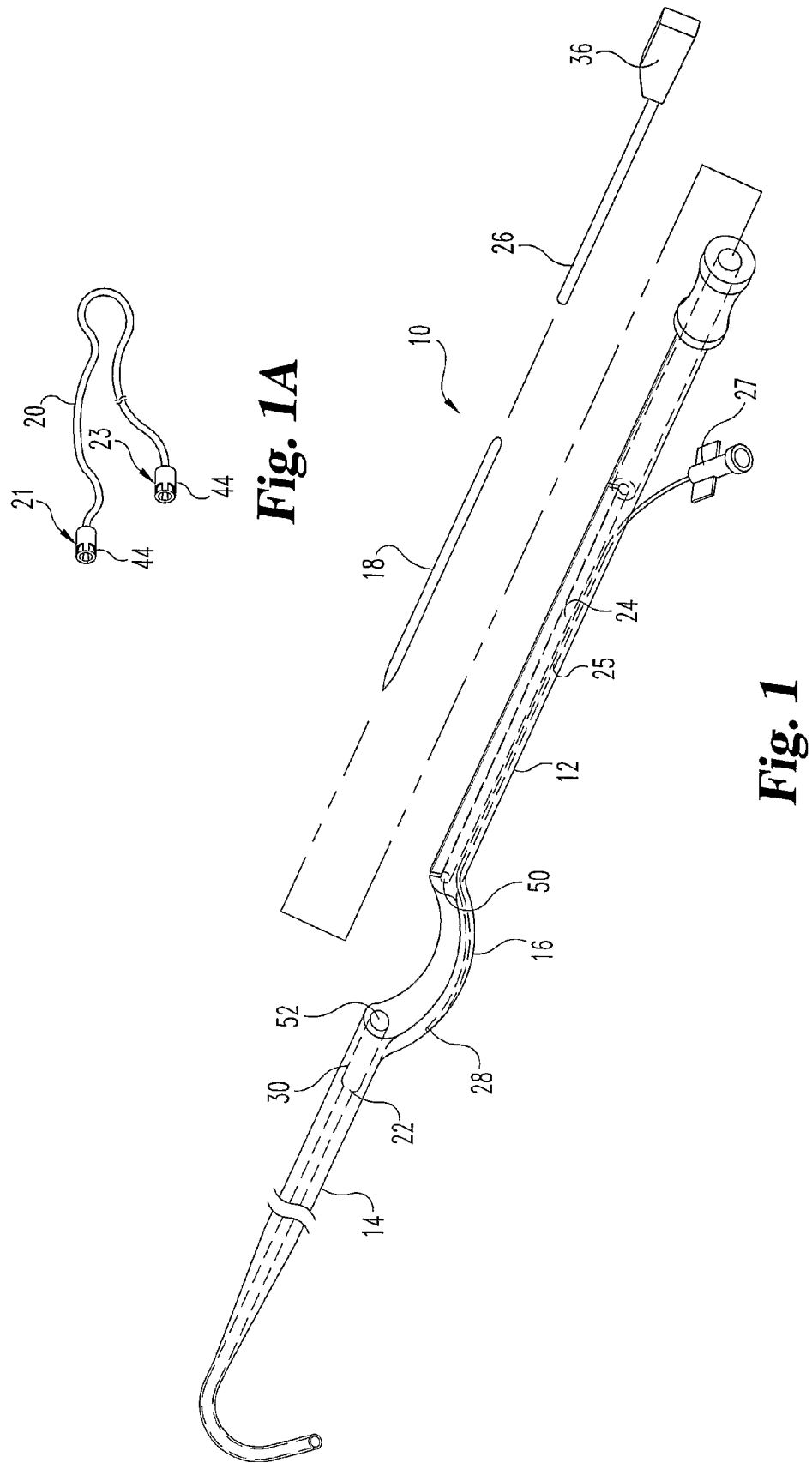
FIG. 1 is an exploded view of one embodiment of a suturing device in accordance with the present invention.

FIG. 1 is an exploded view of one embodiment of a suturing device 10 for suturing vascular vessels in accordance with the present invention. Device 10 includes a proximal member 12, a distal member 14, and an intermediate member 16 located therebetween. Device 10 includes one or more needles 18 advanceable through a portion of the proximal and distal members. A needle pusher 26 can either push or engage needle 18 to advance it through a channel 24 in the proximal member and through vascular tissue adjacent the puncture wound. In one form, suture material can be attached to needle 18 which is then advanced in a distal direction through tissue. In other forms, suture material can be located within distal member to be snared by a needle to be withdrawn in a proximal direction through tissue. A second needle and subsequent needles can be similarly configured and manipulated to place sutures through tissue adjacent a puncture wound in a vascular vessel. The suture material(s) threaded through the vascular tissue can be drawn taut closing the puncture wound. A surgical knot or other suture securing device can complete the wound closure.

As used herein, the term "proximal" refers to a direction toward the surgeon and away from the patient or a location closer to the surgeon, while the term "distal" refers to a direction towards the patient and away from the surgeon or a location closer to the patient.

Proximal member 12 is provided as an elongated portion with a substantially cylindrical or oval radial cross section. Member 12 includes a first end of sufficient dimensions to be readily grasped by the surgeon to manipulate the device during the procedures. Proximal member 12 can also include a gripping portion to facilitate handling during the surgical procedure. Needle channel 24 runs longitudinally along at least a portion of proximal member. In one embodiment, channel 24 extends along the entire length of proximal member from a first end positioned proximal to the surgeon to a second end adjacent to intermediate member 16. In this embodiment, one or more needle(s) 18 and needle pusher(s) 26 can be inserted into and retrieved from channel 24 at the first end. In other embodiments, channel 24 extends only partly through the proximal member 12. Needle channel 24 can be centrally located along proximal member 12. In preferred embodiments, proximal member 12 includes a single needle channel 24 through which one, two, three, or more needles can be advanced. Alleviating multiple needle channels within the suturing device provides a more compact member, which can be particularly advantageous for subcutaneous procedures.

Channel 24 is sized and dimensioned to allow one or more needles 18 to be advanceable therethrough and into vascular tissue around the puncture wound. Furthermore, channel 24 can be either partly or completely encased within the body of proximal member 12. However, in a preferred embodiment, channel 24 is not encased within the body of proximal member 12. Rather, channel 24 is provided as a slot formed into the surface of proximal member 12. Preferably the slot is configured to retain one or more needles within the slot. For example, the slot can be formed to have an opening at the exterior surface of proximal member that is narrower than the diameter of the needles (and optionally the pusher) while the internal portion or diameter of the slot can be dimensioned to permit facile movement of the needle therethrough. An exit opening is located at the distal end of channel 24.

Proximal member 12 includes a blood return line or lumen 25 that terminates in a fitting 27, for example, a luer lock that can be mated to a syringe. Alternatively, blood return lumen 25 can terminate in a valve or shunt to control and stop blood flow therethrough. It is preferable that blood return lumen 25 be transparent to allow visible observation of blood originating from inside the vascular vessel. This can facilitate proper placement of the device for suturing.

Distal member 14 is sized and/or configured to be received within an opening or wound leading to a lumen of a patient's vascular vessel. Therefore, it is preferable that at least distal member 14 be formed of a flexible or elastomeric material that is biocompatible—particularly with blood. In a preferred embodiment, proximal member 12 and distal member 14 define a longitudinal axis. In additional embodiments, distal member 14 can be coated or impregnated with a lubricant, bioactive agent, such as an anticoagulant material, and the like. In certain embodiments, distal member 14 is composed of a biocompatible polymeric material commonly used for catheters, such as silicone rubber, polyolefin polyurethane, polytetrafluoroethylene, and the like.

FIG. 1A illustrates one or more lengths of suture material 20 that can be included in receptacle 22 of distal member 14 in accordance with one embodiment of the present invention. The lengths of suture material 20 can include one or more fittings 21, 23, for example, a ferrule or cuff of porous or mesh material, to engage the needle.

Figure 2:
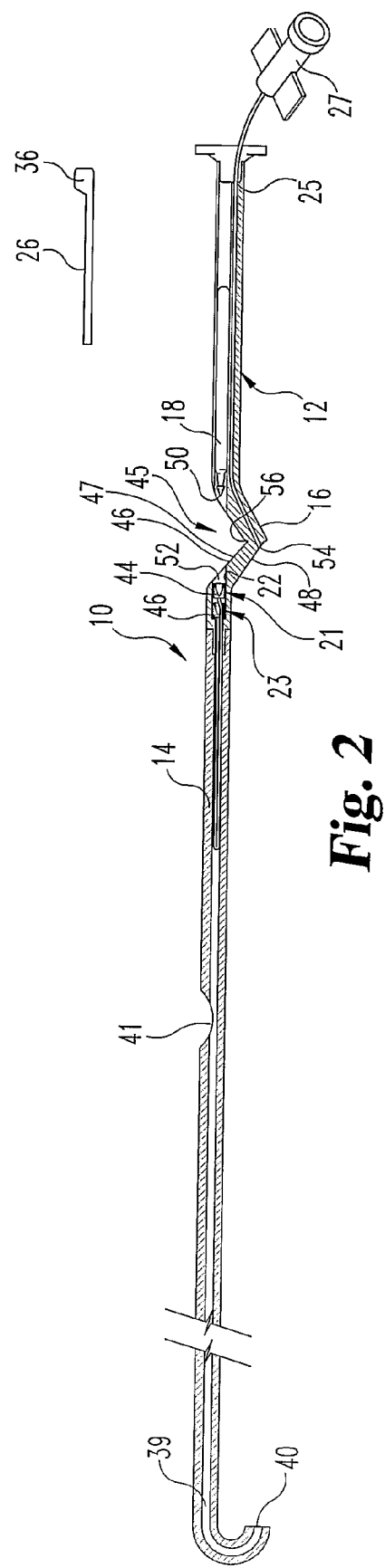
FIG. 2 is a cross-sectional view of the suturing device of FIG. 1 including the suture material of FIG. 1A.

Distal member 14 includes a receptacle 22. Receptacle 22 is sized to receive at least one length of suture material 20 with a corresponding fitting 21, as specifically shown in FIG. 2. Preferably receptacle 22 is sized to hold one, two, or more separate lengths of suture material. Each length of suture material can include either a single fitting 21 or two fittings—one on each end. In a preferred embodiment, receptacle 22 is provided as a multi-stage or tapered recess. Each fitting is positioned within a receptacle to allow for ready deployment and subsequent engagement with needle 18 advancing from channel 24 in proximal member 12. Preferably the fittings are releasably retained so that needles advancing into receptacle 22 can sequentially engage the fittings without forcing that fitting distally further or deeper into the receptacle. In one form, this can include a shoulder or abutment 30 extending from the internal wall of receptacle 22 to abut a distal end of a fitting. In other embodiments, this can include configuring the internal dimensions of receptacle 22 to taper or decrease in diameter in the distal direction. In other embodiments, a multi-stage receptacle 22 or stepped internal walls receptacle 22 can prevent movement of the fittings in the distal direction. In still other embodiments, the fittings are loaded within the receptacle 22 to bear against the suture material which is packed within the end of receptacle 22. In this embodiment, the bulk of suture material in receptacle 22 can inhibit or prevent distal movement of the fittings upon initial engagement with needle 18.

Figure 3:
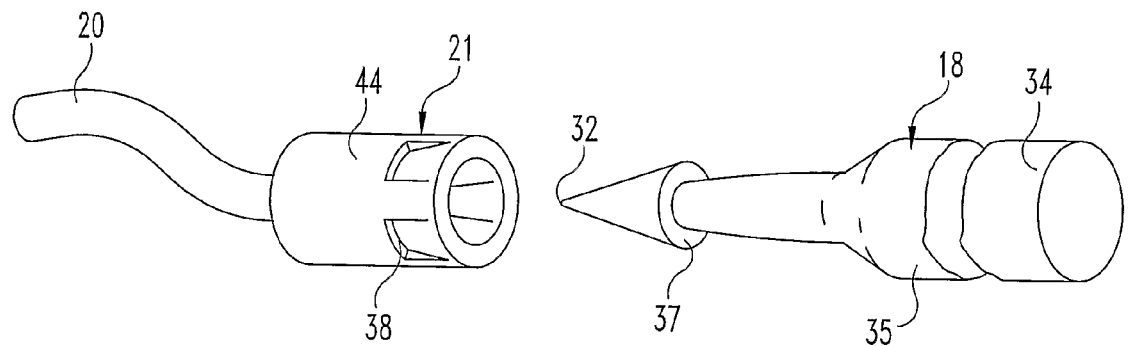
FIG. 3 is a perspective view of a ferrule and a needle for use with the suturing device in accordance with the present invention.
Figure 4:
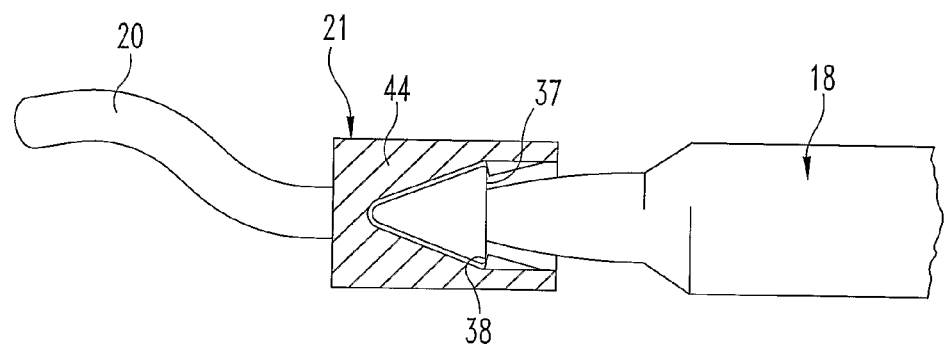
FIG. 4 is a cross-sectional view of the ferrule engaged with the needle of FIG. 3.

FIGS. 3 and 4 illustrate a portion of needle 18 and fitting 21 in the form of a ferrule 44 . . . Needle 18 includes a distal tip 32 and a proximal end 34. Distal tip 32 is configured as a tissue piercing point or a barbed tip. Needle 18 is configured to grab suture material located in the lumen of the vessel and withdraw the suture material through vascular tissue. In the preferred embodiment, distal tip 32 is configured to securely engage with ferrule 44 which, in turn, is attached to a length of suture. Ferrule 44 can be extremely small, having roughly a diameter similar to or slightly larger than that of the suture material 20. Alternatively, ferrule 44 can have approximately the same diameter as the diameter of needle shaft 35. In this embodiment, distal tip 32 has a smaller diameter to allow it to be received inside ferrule 44. Distal needle tip 32 includes at least one recessed engagement surface or shoulder 37 configured to matingly engage with a corresponding engagement surface 38 provided on or in ferrule 44. In one form, the engagement surface is a tab extending into the interior of ferrule 44. In other embodiments, the engagement surface is a shoulder extending radially inward in ferrule 44 or a groove partly or completely encircling an interior wall of ferrule 44. Fitting 23 also may be in the form of a ferrule 46 shown in FIGS. 5 and 6. Ferrule 46 may have similar needle retention features.

Figure 5:
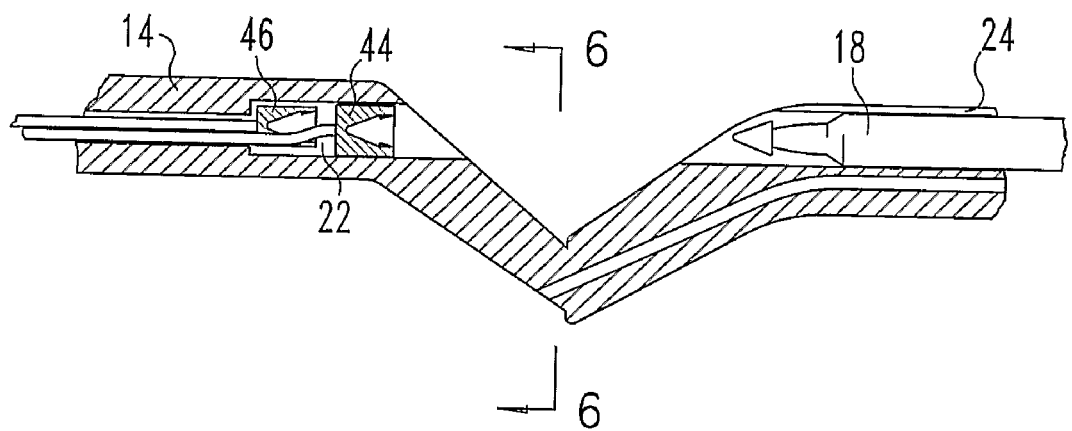
FIG. 5 is an enlarged, cross-sectional view of the intermediate member of the suturing device of FIG. 1 with the suture material of FIG. 1A.
Figure 6:
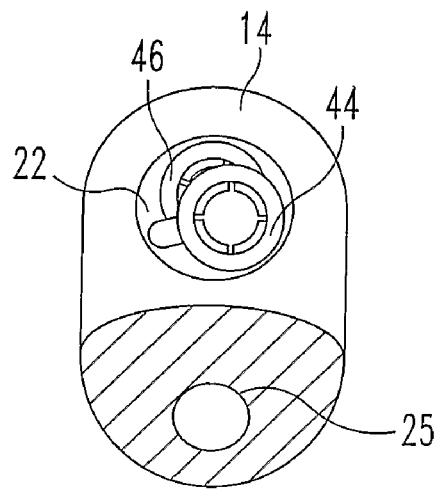
FIG. 6 is a radial cross-sectional view taken along section line 6-6 of the intermediate member illustrated in FIG. 5.
Figure 9:
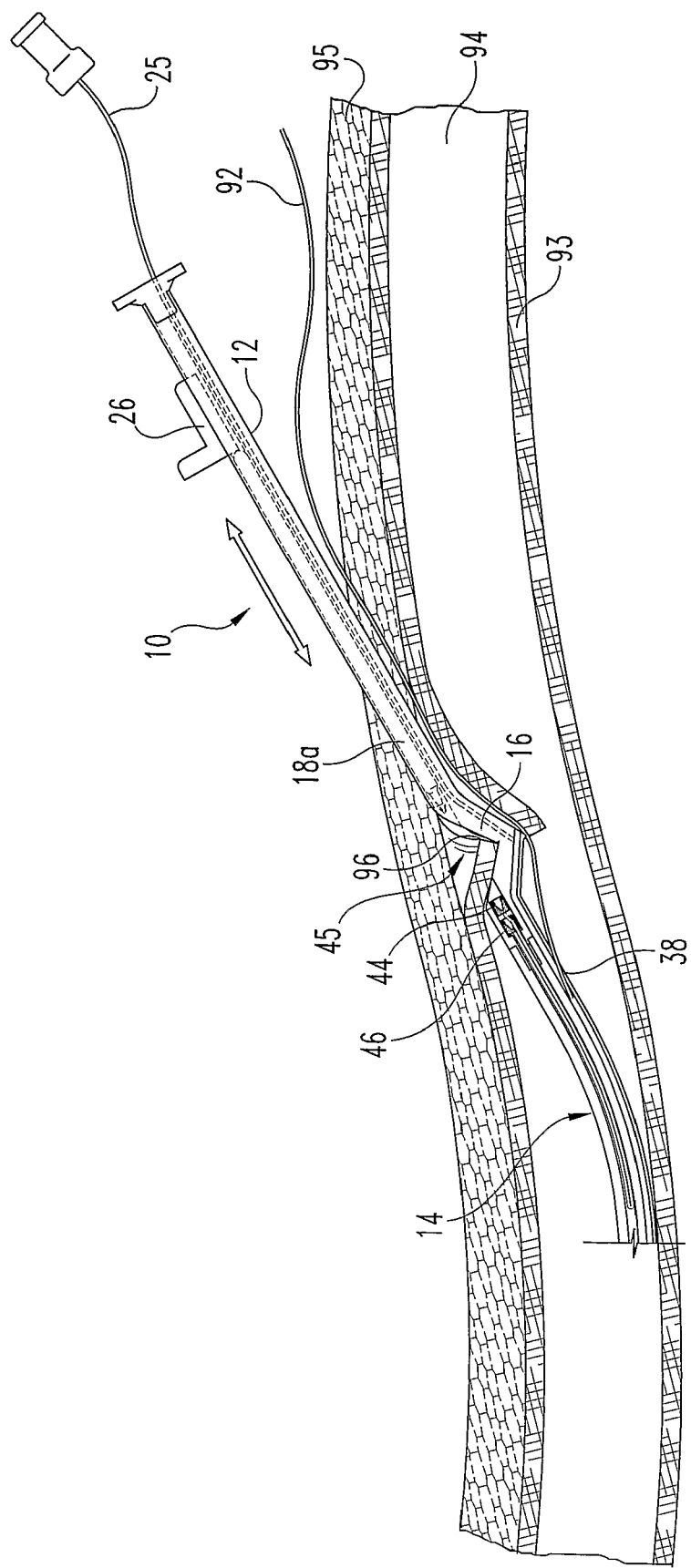
FIGS. 9-16 illustrate the use of the suturing device of FIG. 1 to suture vascular tissue.

FIGS. 5 and 6 show that the ferrules 44 and 46 need not be the same size—particularly the same diameter. In this regard certain advantages can be gained by providing the proximally located ferrule 44 with a diameter greater than that of the distally located ferrule 46. For example, this will allow sufficient room for the suture material extending from ferrule 44 to extend along side of ferrule 46—between ferrule 46 and an internal wall section of receptacle 22. In other considerations, the suture material from the proximally located ferrule 44 can be disposed between that ferrule and the next distally located ferrule 46. Ferrules 44 and 46 can also be tapered or "streamlined" to allow them to be readily pulled through a small needle puncture site in tissue as described below.

In one embodiment, the length of suture material which is attached to the different ferrules on each end can include different color codings for the different ends. This allows a surgeon to differentiate which sutures are attached to which ferrules to facilitate tying suitable knots to close puncture 96 in the vessel.

One or more of needles 18 and ferrules 44, 46 for use in the present invention can be provided as substantially described in U.S. Pat. No. 6,136,010 issued to Modesitt et al. and/or U.S. Pat. No. 6,368,334 issued to Sauer, which are incorporated herein by reference in their entirety.

Proximal end 34 of needle 18 can be free and configured to be handled by a surgeon. Alternatively, proximal end 34 can be engageable or secured to a needle pusher 26 shown in FIG. 2. In yet another embodiment, proximal end 34 can be integral or formed as a single unit with needle pusher 26. In either embodiment, needle pusher 26 is sized to be positioned within channel 24 and can further include a projection 36 to allow the surgeon to advance the needle pusher/needle combination along channel 24. In a preferred embodiment, needle pusher 26 is configured such that the surgeon can sequentially advance needle 18 in a proximal direction towards the patient and in a distal direction away from the patient.

Referring back to FIG. 2, distal member 14 can also include a lumen 39 extending at least partially therethrough. Preferably, lumen 39 is separate from receptacle 22. Lumen 39 can be provided to receive or follow a guide wire left in place after a particular diagnostic or treatment procedure. This can allow the facile insertion of distal member 14 into the patient's vascular vessel. In a preferred embodiment, an opening 40 receives a guide wire (not shown) that extends through lumen 39 and exits through a side opening 41 of distal member 14 to permit the guide wire to extend out without interfering with the needles, needle path, or suture material. The guide wire can be removed after placement of the suture device or left in as desired or considered medically prudent by the surgeon.

Intermediate member 16 is located between proximal member 12 and distal member 14. Intermediate member 16 defines a tissue-receiving area 45. In the illustrated embodiment, intermediate member is configured to include an arcuate portion or a crooked section. The arcuate portion or crook thus defines a concave interior surface 47 and a convex exterior surface 48. Intermediate member 16 includes a first opening 50 providing access from the channel 24 to the tissue receiving area 45 and a second opening 52 from the receptacle 22 providing to the tissue receiving area 45. Preferably, first and second openings 50 and 52 are linearly or axially aligned. Intermediate member 16 can be composed of a biocompatible material that is substantially resistant to deformation and therefore can maintain the linearity between channel 24 and receptacle/chamber 22 and the respective first and second openings 50 and 52. Examples of suitable materials include TEFLON, NYLON, polyamids, and the like.

Intermediate member 16 also includes means and structure for reliable positioning of the device during surgery to facilitate closing the vascular puncture wound with sutures. Part of the positioning structure includes an opening 54 providing fluid communication to blood return lumen 25 in proximal member 12. In a preferred embodiment, opening 54 is located on a portion of the convex surface of the crook opposite the tissue receiving area 45. When the distal member 14 of the device is suitably positioned within the lumen of a vascular vessel, opening 54 is also located in the interior of the lumen. This permits blood from the vessel to enter blood return lumen 25, which can then be visibly observed by the surgeon. If blood is not observed in blood return lumen 25, then the distal member may not have been inserted to a sufficient depth into the lumen of the vascular vessel.

Additionally, a ridge or stop 56 extends from the concave surface into the tissue receiving region. Stop 56 is configured to bear against vascular tissue adjacent the puncture wound. In a preferred embodiment, first opening 50 is adjacent stop 56 permitting needle 18 to pierce tissue adjacent thereto. Stop 56 is sized to bear against the vascular tissue and avert further insertion of the device 10 into the vascular vessel. When provided together, stop 56 and opening 50 with blood return lumen 25 cooperate to ensure accurate placement of the suturing device in the patient's vascular vessel. Ridge or stop 56 can also extend radially about the entire circumference of intermediate member 16.

FIG. 7 is a cross-sectional view of an intermediate member 70 of an alternative embodiment of a suture device. In this embodiment, fittings 72 and 73 are positioned radially or laterally displaced from each other in receptacle 74. A first fitting 72 is positioned axially aligned with second opening 75 in the distal member 76. A biasing element such as a leaf spring 77 can also be positioned in receptacle 74 to urge second fitting 73 into axial alignment with opening 75 once first fitting 72 has been displaced. Biasing element 77 can be a leaf spring as illustrated, an elastomeric projection, or other known biasing material suitable to urge fitting 72 into alignment as desired.

FIG. 8 is a perspective view of another embodiment of a suturing device 80 with a needle cartridge in accordance with the present invention. Device 80 includes a proximal member 81, a distal member 82, and an intermediate member 83 therebetween. Proximal member 81 includes a needle cartridge 84 slidably mounted in body 85. Needle cartridge 84 can include a plurality of needle slots, for example one, two, three, or more slots 86a, 86b, 86c . . . , each for a separate needle. Typically, the number of needles in needle cartridge 84 will coincide with the number of fittings with suture material in the receptacle in distal member 82. Each needle in needle cartridge 84 is individually advanceable through a central needle channel 87 along a length of proximal member 81. Needle cartridge 84 is laterally displaceable within body 85 to axially align the selected needle slot 86a, 86b, 86c . . . with a single needle channel. If desired, needle cartridge can be biased to automatically align the successive needle slots with the needle channel after the preceding needle has been advanced along the channel. Alternatively, suturing device 80, body 120, and/or cartridge 118 can include one or more of ratchetings, positive stops, or locks to individually align the desired needle slot with the channel. In other embodiments, needle cartridge 84 can be provided as a revolving barrel that can hold two, three, or more needles in respective needle slots radially disposed about the barrel. The barrel can be rotatably mounted on or about proximal member 81. Distal member 82 and intermediate member 83 can be configured substantially as described above for members 14 and 16, respectively.

Referring to FIGS. 9 through 14, use of the suturing device 10, will now be described. A puncture wound in a vascular vessel can be sutured closed using the suturing device 10. Suturing device 10 can be inserted distally into the vascular vessel. This can be accomplished with or without the use of a guide wire. In a procedure where a guide wire has been previously used, suturing device 10 can be threaded onto a guide wire 92 which extends from internal vessel lumen 94 through a puncture wound 96 in vessel 93 and through a portion of the overlying tissue 95 to be exposed to the surgeon. In that regard, side opening 41 of lumen 39 can be threaded onto guide wire 92 which then extends out through opening 40. Thus, the flexible portion of distal member 14 can be gingerly threaded into the lumen 94 of vessel 93. The distal member 14 of device 10 can be positioned within lumen 94 such that intermediate member 16 engages with a portion of the tissue surrounding puncture 96. Distal member 14 is advanced in a distal direction until blood is observed in blood return lumen 25. Additionally, when provided, stop 56 abuts or bears against the external surface of the vascular vessel. This can be detected by the increased resistance to further advancement of the device in the distal direction. Both blood return lumen 25 and stop 56 can be used to ascertain that the device has been correctly positioned within the lumen 94 of the vascular vessel 93 to allow suturing of puncture 96. It should be noted that observance of blood in needle channel 24 is an indication that device 10 has been inserted too far into the lumen such that first opening 50 is exposed to the interior or blood side of vessel 93. If desired, guide wire 92 can then be withdrawn from lumen 39 and out of vascular vessel 93—if it is no longer needed for subsequent procedures.

After the distal member 14 is positioned as desired, the vascular tissue adjacent the puncture wound is received within the tissue receiving area 45. As noted above, intermediate member 16 provides an essentially linear needle pathway between channel 24, receptacle 22, and the vascular tissue in the tissue receiving area 45. Consequently, when needle 18 is advanced through channel 24, it pierces the vascular tissue at a first suture site 97 adjacent the puncture wound 96.

Figure 10:
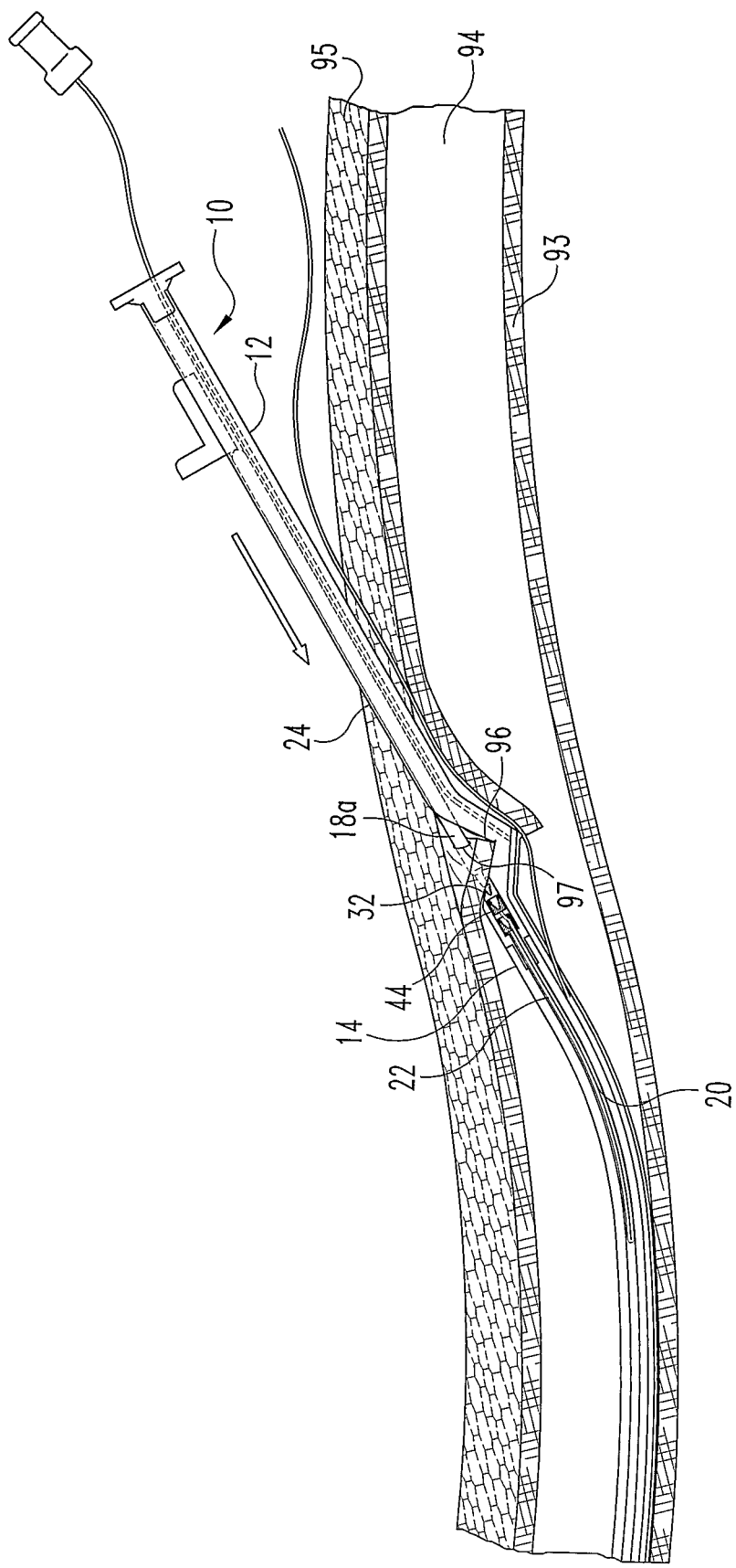

FIG. 10 illustrates suturing device 10 at a first suture position with needle 18a advancing distally through channel 24 and piercing the vascular tissue of vessel 93 at a first suture site 97 on a first side of wound 96. From there, needle tip 32 advances into to receptacle 22 to engage in a first ferrule 44. Once engaged with ferrule 44, first needle 18a can then be withdrawn back through opening 52 in distal member 14 and through first suture site 97, drawing a length of suture material 20 through the vascular tissue in a proximal direction as illustrated in FIG. 1. Preferably the needle path in the proximal direction is the same as in the distal direction—provided that the suturing device has not been moved or dislocated. Needle 18a, including a length of suture material 20, can then be removed from suture device 10. Alternatively, needle 18a and/or a length of suture material can be retained with suture device 10 for subsequent retrieval and use in securing the wound closure.

Figure 12:
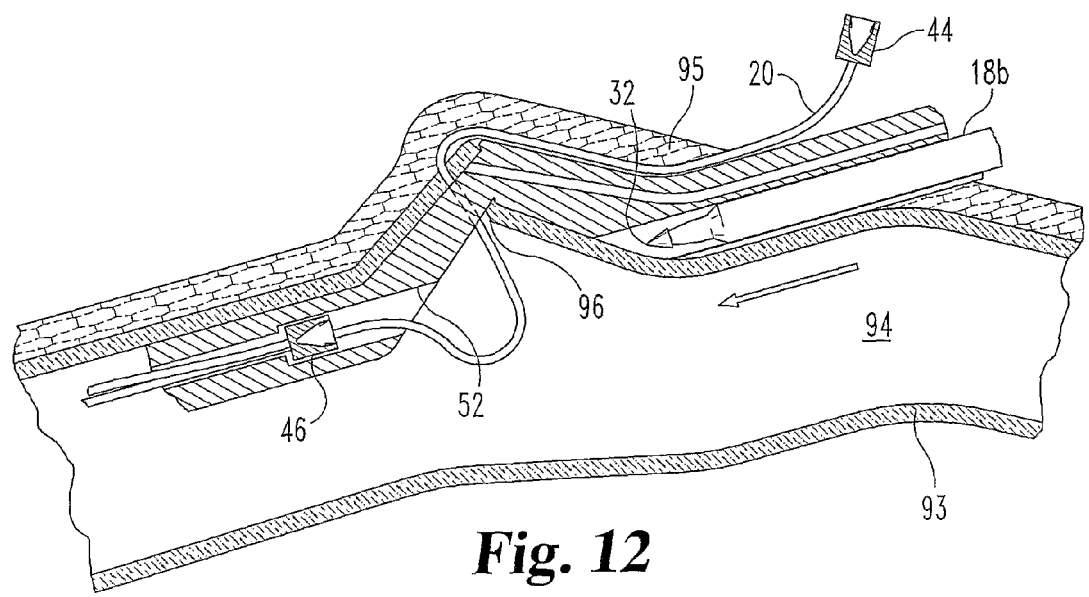
Figure 13:
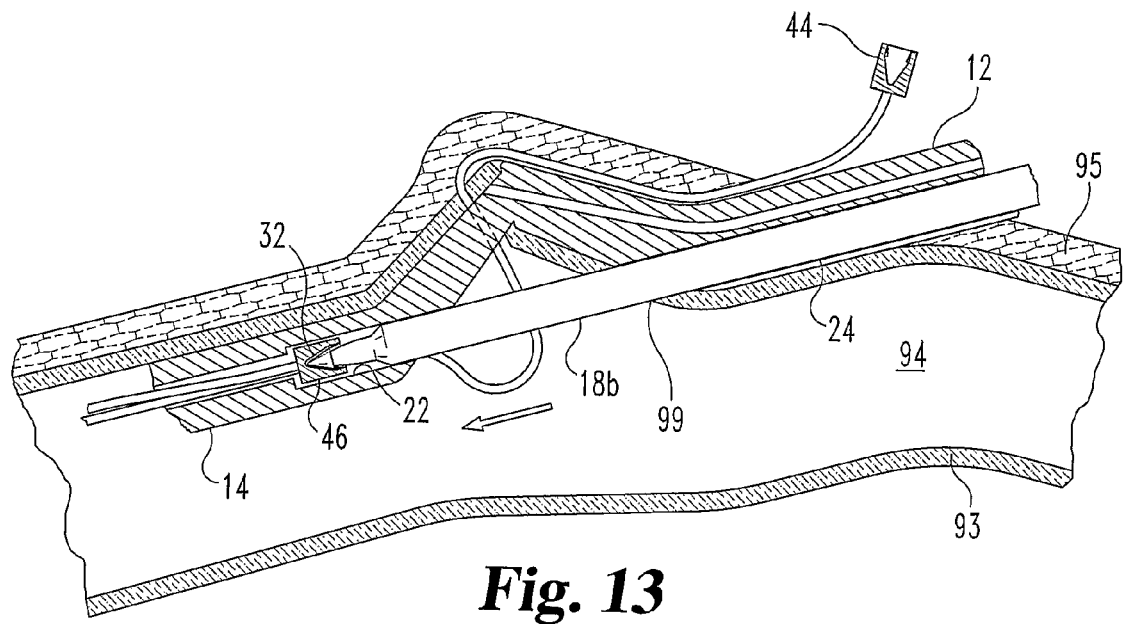
Figure 14:
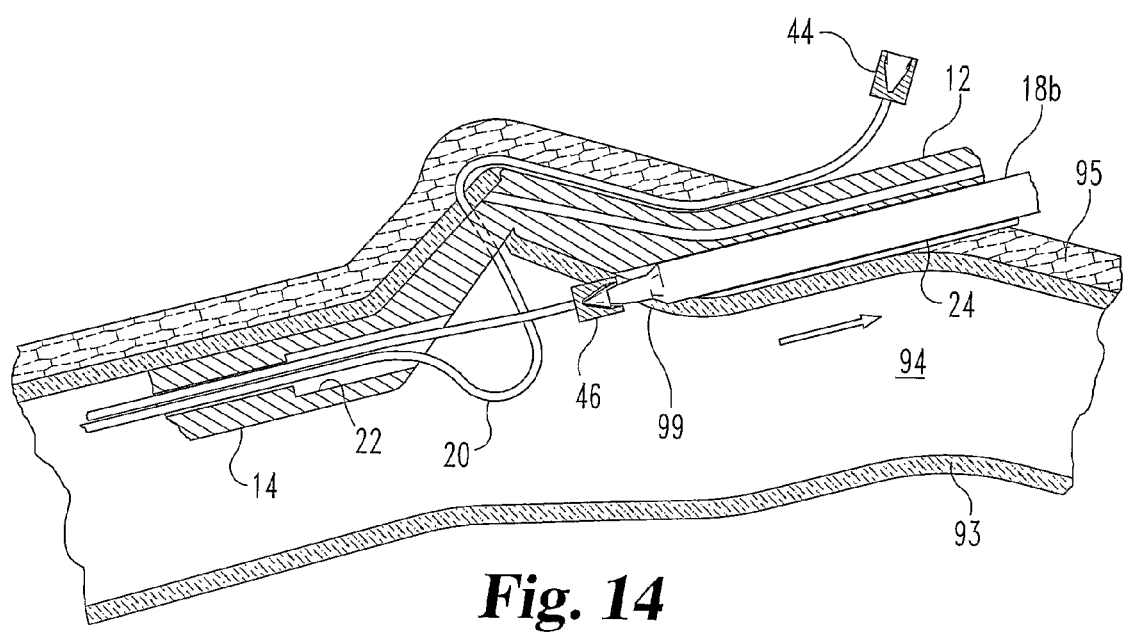
Figure 15:
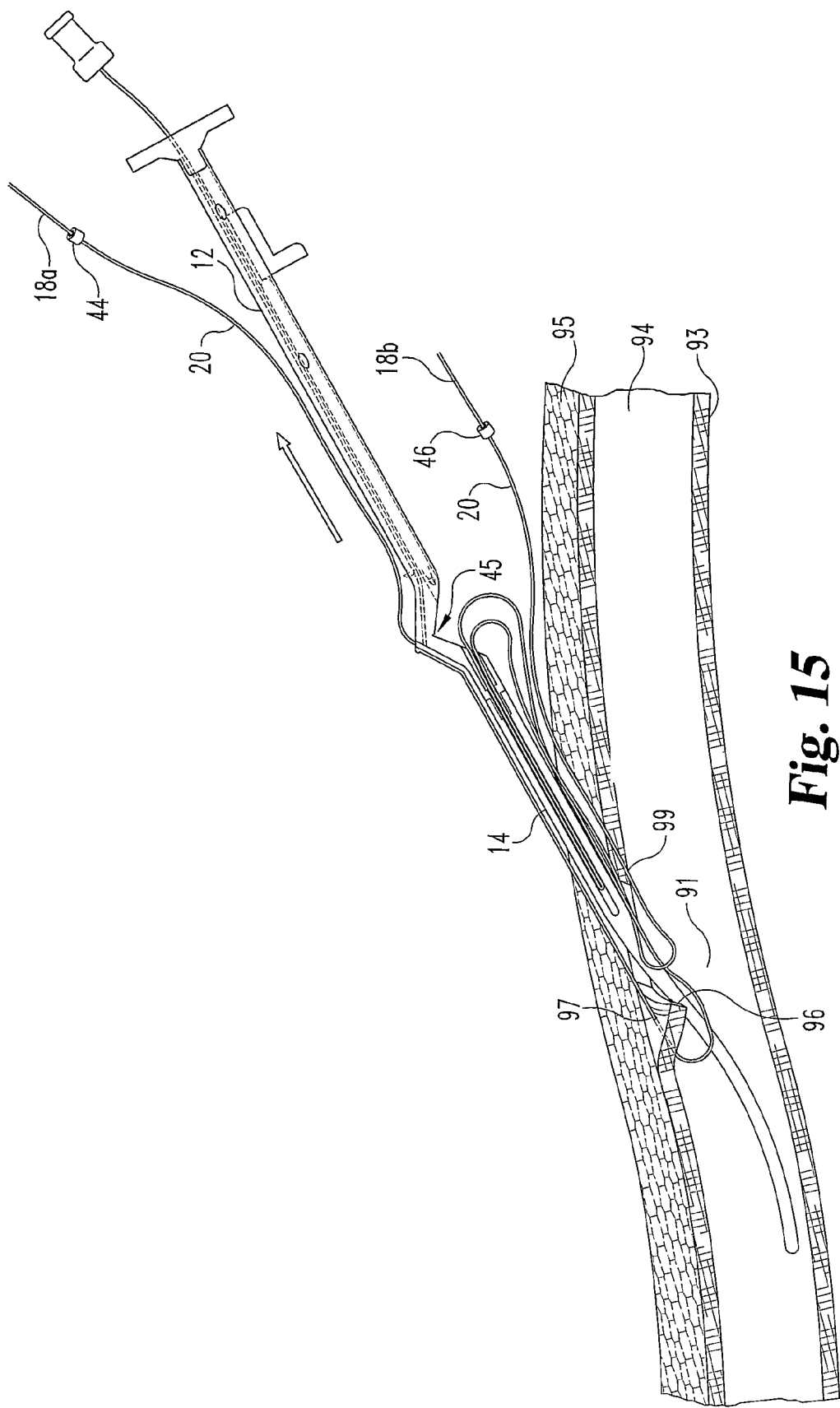

Thereafter, suture device 10 is rotated into a second suture position as illustrated in FIG. 12. For example, suture device 10 may be rotated approximately 180° so that in the second suture position, suture device 10 is positioned to operate on a second side of puncture 96 diametrically opposite first suture site 97. After ensuring that the suturing device is correctly positioned, the procedure described above for needle 18a can be followed. At the second suture position, a second needle 18b is distally advanced using a needle pusher, either the same needle pusher or a second, different needle pusher, through channel 24 to engage in and pierce the vascular tissue 93 received within tissue receiving area 45 at second suture site 99. Again, needle 18b is advanced to enter receptacle 22 and there engage with second ferrule 46 as shown in FIG. 13. Withdrawal of the needle pusher concomitantly withdraws ferrule 46, and a length of suture 20 through second suture site 99 as shown in FIG. 14. Needle 18b and the attached ferrule 46 and length of suture material can be retrieved by the surgeon either by hand or received within a slot in the proximal member. Thereafter, if desired, the process can be repeated, rotating suturing device 10 through about 90° and again, advancing a needle to engage in a subsequent ferrule located in receptacle 22. This process can be repeated as desired and as provided with a number of needles and/or suture materials with ferrules in receptacle 22. It will be understood that in one embodiment, first and second lengths of suture materials are two ends of the same suture. In other embodiments, lengths of suture material are separate pieces of suture. Thereafter, device 10 can be withdrawn from the body as illustrated in FIG. 15.

Figure 16:
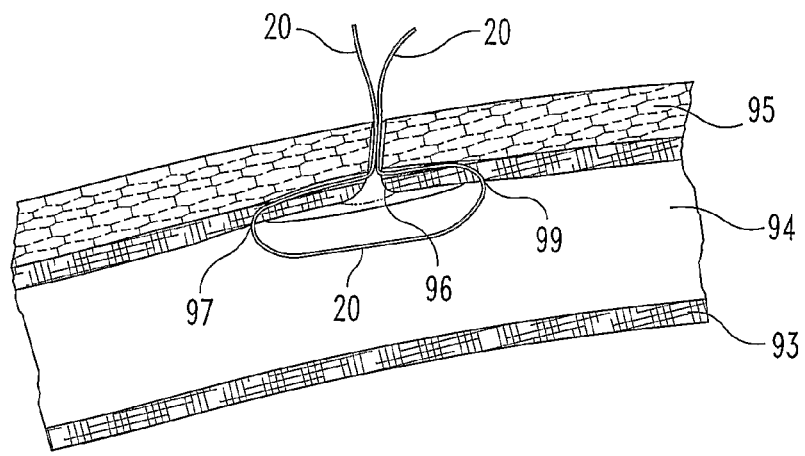

As illustrated in FIG. 16 the lengths of suture material 20 can be gathered. The length of suture material can be separated from the needles. Pulling the lengths of suture material taut closes the wound 96 in the vessel 93. In this embodiment, the path of the suture material passes through vascular tissue on a first side of the wound into the lumen 94 of the vessel 93, across the wound 96—again in the lumen 94—and then out through the vascular tissue 93 on a second or opposite side of the wound. A surgical knot can be tied securing the wound closure. A knot pusher, for example, the knot pushers described in U.S. Pat. No. 5,304,184 issued to Hathaway et al., U.S. Pat. No. 5,746,755 issued to Wood et al., and U.S. Pat. No. 6,132,439 issued to Kontos, can be used to advance the loosely tied knot to the exterior surface of the vascular vessel. In selected embodiments, the surgeon can then tie a suitable surgical knot using the respective lengths of suture material to close the puncture wound 96. In other embodiments, the suture material can be secured using a variety of knot replacement technologies such as that disclosed in U.S. patent application Ser. No. 10/164,606 (US Patent Publication No. 2003/0229377) and in Ser. No. 10/305,923 (US Patent Publication No. 2004/0102809) and depicted in FIGS. 21 and 22. Each of the above-noted references are incorporated by reference in their entirety.

Figure 17:
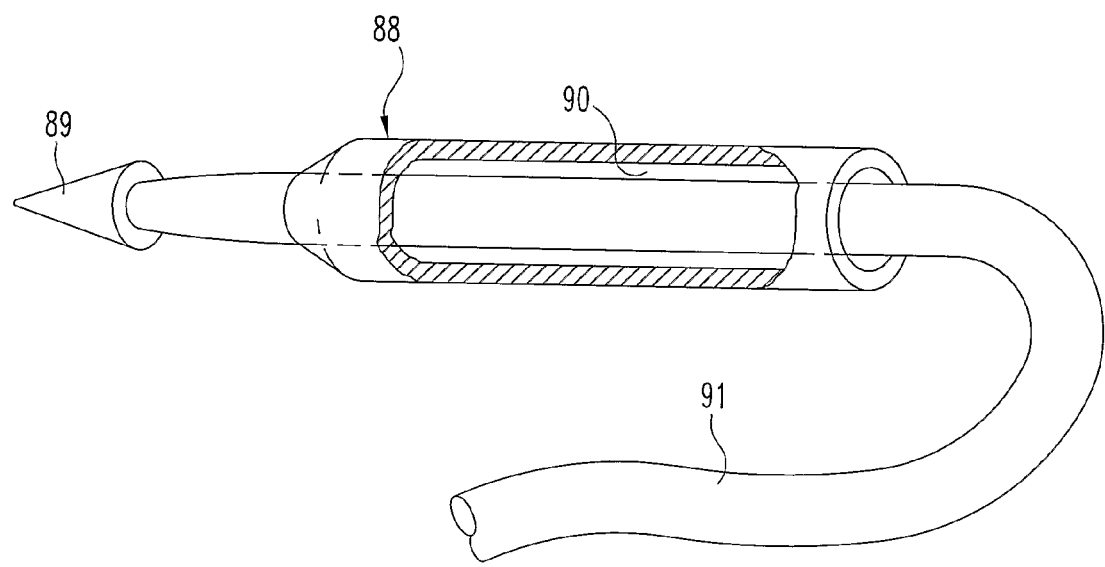
FIG. 17 is a perspective view of a hollow needle for use in the suturing devices described herein.

FIG. 17 is a perspective view of one embodiment of a hollow needle 88 for use in accordance with the present invention. Needle 88 includes a detachable tip 89, a hollow shaft 90, and a length of suture material 91. The length of suture material 91 extends out the proximal end of hollow needle 88. In one embodiment, one end of the suture material 91 is attached to needle tip 89. In this embodiment, the needle tip 89 can be used to pull suture material 91 through a portion of a suturing device or through vascular tissue as discussed more fully below.

Figure 18:
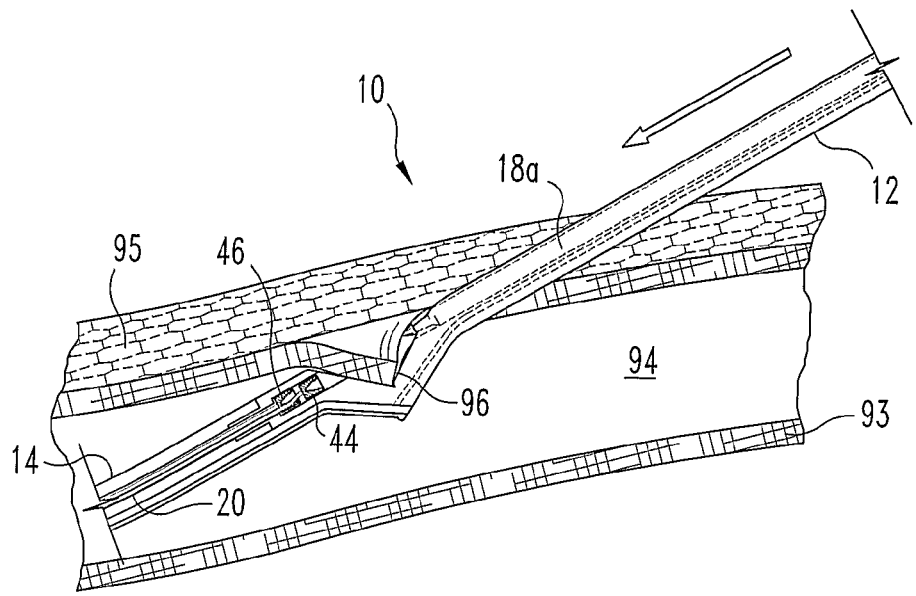
FIGS. 18-20 illustrate the use of the suturing device of FIG. 1 with a hollow needle of FIG. 17.
Figure 19:
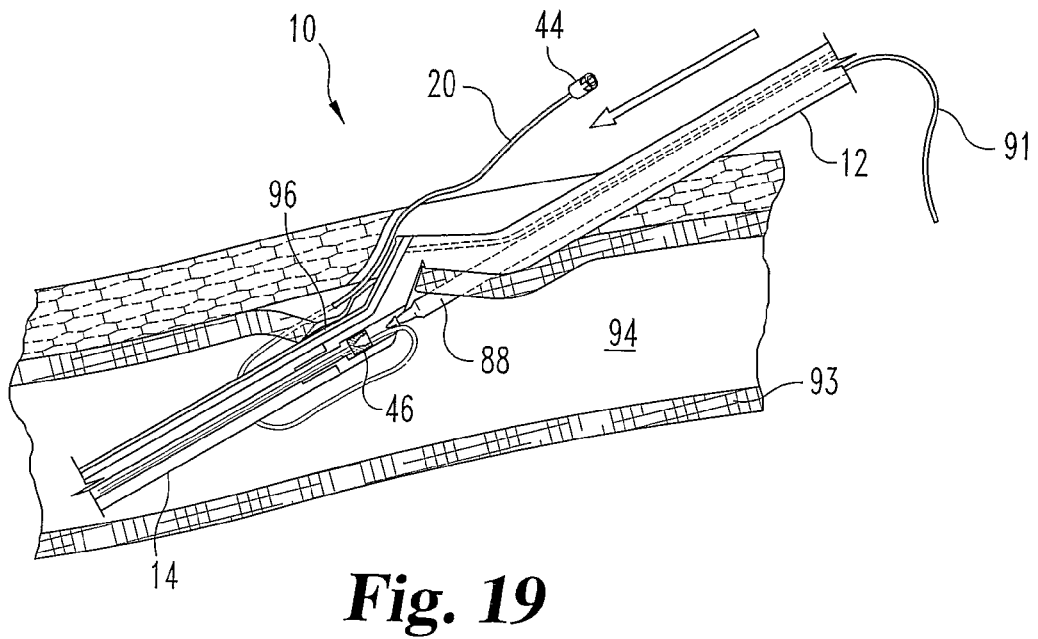
Figure 20:
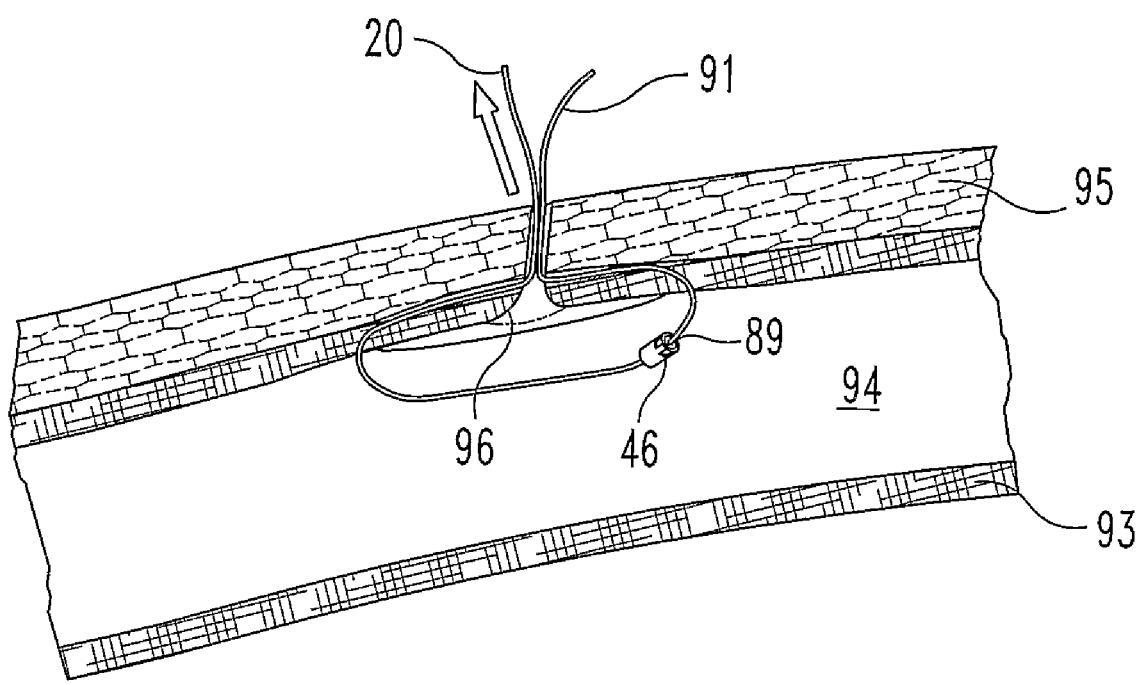

FIGS. 18 through 20 illustrate the use of hollow needles with the suturing device 10. The suturing device 10 is inserted into the vascular vessel as described above and illustrated in FIG. 9. After suturing device 10 has been positioned within the lumen 94 as desired, needle 88 is advanced in the distal direction through needle channel 24 to pierce vascular tissue 93 adjacent the wound 96 in the vessel and then into recess 22 to engage with a first ferrule 44. Needle 88, the attached ferrule 44, and a length of suture material 20 are withdrawn in the proximal direction back through the needle path through a first suture site.

Suturing device 10 can be rotated about its longitudinal axis while maintaining the distal member within the vascular lumen to a second suturing position. FIG. 19 illustrates the advancement of hollow needle 88 along channel 24. Hollow needle 88 can pierce vascular tissue 93 at a second suture site. Needle tip 89 can then engage with the second ferrule 46 located in receptacle 22. Once engaged to second ferrule 46, needle tip 89 can be separated from shaft 90 by withdrawal of the needle shaft 90 back through the second suture site. The needle shaft can be received in or through channel 24. Suture material 91 is then connected to suture material 20 via ferrule 46 and needle tip 89. Suturing device 10 can then be removed from the vascular vessel and eventually from the patient.

Referring now FIG. 20, suture material 20 and 91 are connected together using second ferrule 46 and needle tip 89. The connected suture material can be pulled in either direction by 1) pulling on suture material 20 in the distal direction to draw ferrule 46, needle tip 89, and a portion of suture material 91 through the second suture site, or 2) pulling on suture material 91 in the distal direction to draw ferrule 46, needle tip 89, and a portion of suture material 20 through the second suture site. In yet other embodiments, the free ends of suture material 20 and 91 can be pulled taut to close the vascular wound. Preferably in this embodiment both of needle tip 89 and ferrule 46 (as well as the suture materials) are composed of a biodegradable material to biodegrade. Biodegradable materials for the ferrule, needle tips, and suture material are well known in the art and these materials are useful to prepare the components of the present invention.

Figure 21:
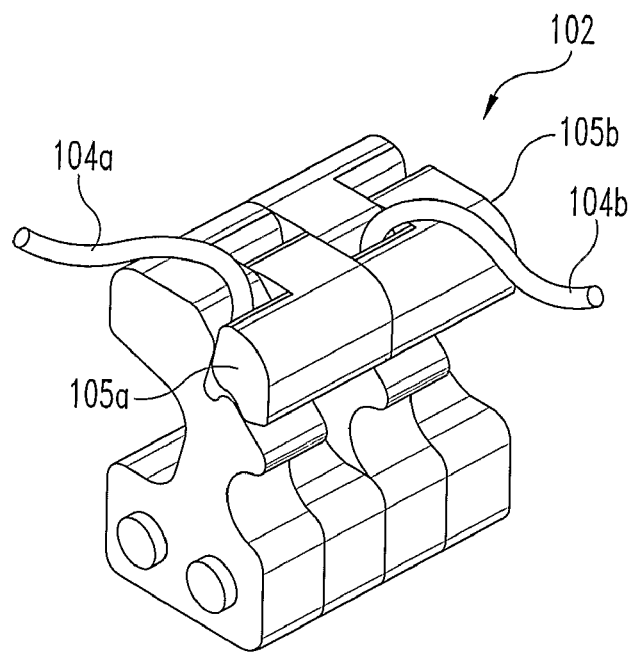
FIG. 21 is a perspective view of one embodiment of a suture securing device for use in the present invention.

FIG. 21 is a perspective view of a suture securing device 102 for use in the present invention. Suture clamping device 102 is described and illustrated in US Patent Publication No. 2004/0102809 which is incorporated herein by reference. In use, device 102 can secure ends of one, two, three or more lengths of suture material. Two lengths of suture material 104a and 104b are illustrated with device 102. The lengths of suture material are threaded into the flexible elements 105a and 105b which are then locked or fixed together clamping the suture material therein.

Figure 22:
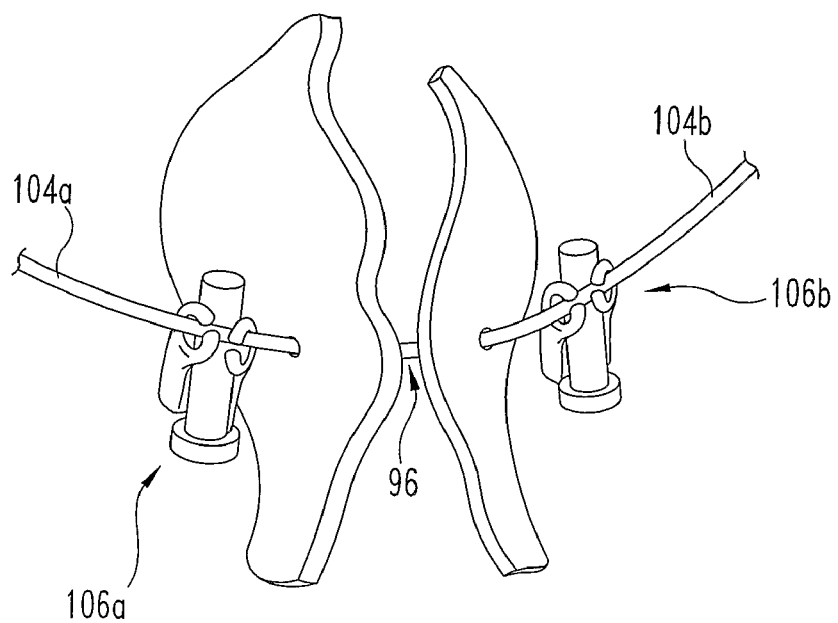
FIG. 22 is a perspective view of an alternative embodiment of a suture securing device for use in the present invention.

FIG. 22 shows another embodiment of suture clamping devices 106a and 106b for use in the present invention. Devices 106a and 106b are described in US Patent Publication No. 2003/0229377 which is incorporated herein by reference in its entirety. Devices 106a and 106b cooperate by separately clipping onto a selected length of suture material 104a or 104b which have previously pulled taut to close the wound 96 or complete the surgical procedure. The devices prevent the suture material from regressing back through the sutured tissue.

Figure 23:
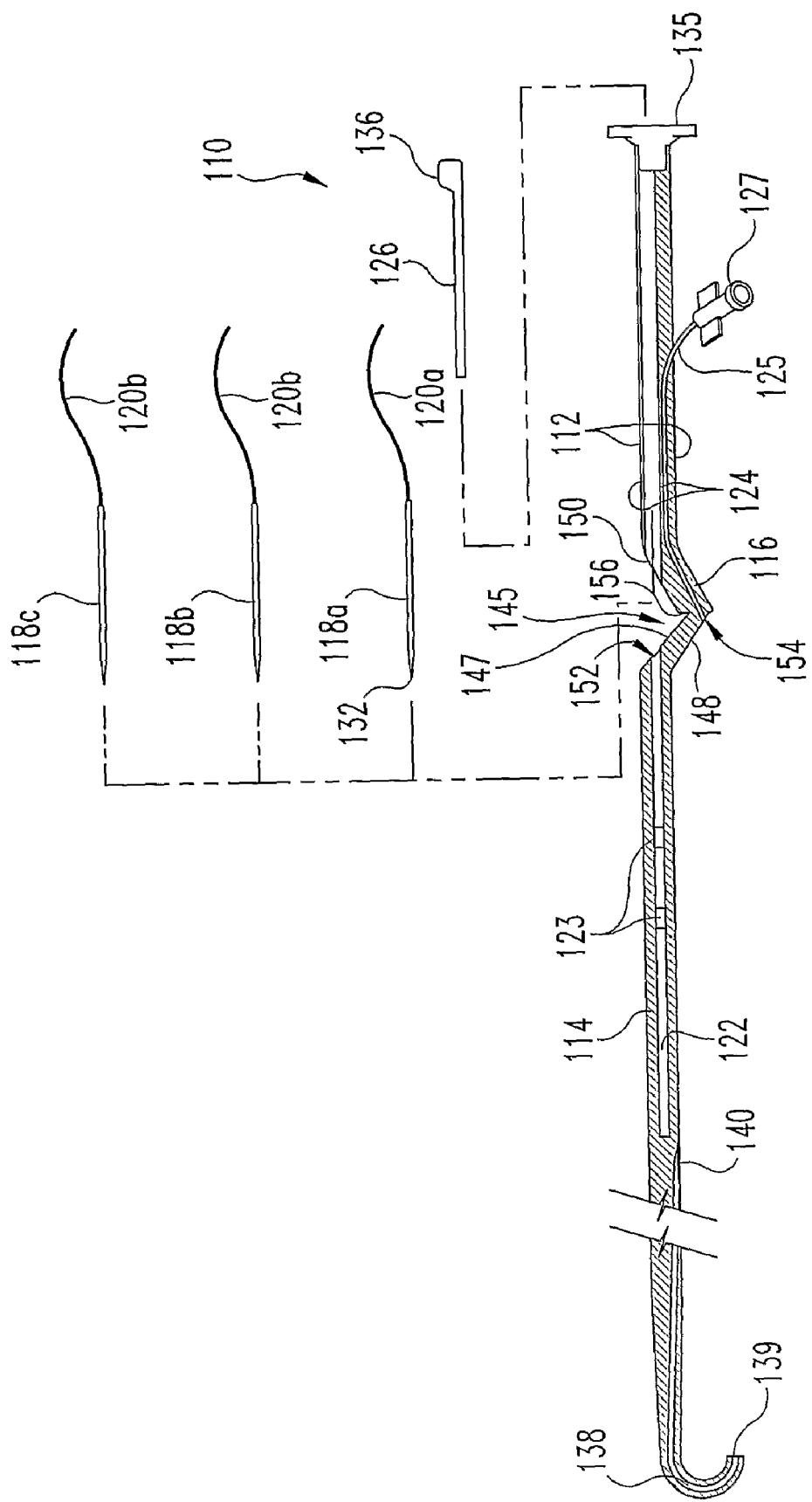
FIG. 23 is a cross-sectional view of one embodiment of a suturing device with a needle capture element in accordance with the present invention.

FIG. 23 shows a suturing device 110 for suturing vascular vessels in accordance with the present invention. Device 110 includes a proximal member 112, a distal member 114, and an intermediate member 116 located therebetween. Device 110 includes one or more needles 118a, 118b, 118c . . . disposable within needle channel 124 of proximal member 112. Each of needles 118a, 118b, 118c . . . can include a length of suture material 120a, 120b, 120c . . . secured to the proximal end of the needles. Needle pusher 126 can be used to advance the needles 118a, 118b, 118c, . . . through channel 124 out through first opening 150 into a tissue receiving area 145 defined by intermediate member 116. Preferably, proximal member 112 and/or distal member 114 define a longitudinal axis and (either/both) is/are essentially linear about this axis. In one embodiment, the intermediate member 116 can be configured to deviate from the lineality defined by either the proximal member (or the distal member). First opening 150 and second opening 152 in intermediate member can be axially aligned to permit needles 118a, 118b, 118c . . . to travel in an essentially linear needle path that extends through tissue received within tissue receiving area 145. In one form, suture material can be attached to the needle 118a. The needle is then advanced in a distal direction through tissue. A second needle 118b (and subsequent needles) can be similarly configured and manipulated to place sutures about tissue adjacent a puncture wound in a vascular vessel. The suture material(s) threaded through the vascular tissue can be drawn taut closing the puncture wound. A surgical knot or other suture securing device can complete the wound closure.

As used herein, the term "proximal" refers to a direction toward the surgeon and away from the patient or a location closer to the surgeon, while the term "distal" refers to a direction towards the patient and away from the surgeon or a location closer to the patient.

Proximal member 112 is provided as an elongated portion and can exhibit a substantially cylindrical or oval radial cross section. Member 112 includes a first end of sufficient dimensions to be readily grasped by the surgeon to manipulate the device during the procedures. Proximal member 112 can also include a gripping portion 135 to facilitate handling during the surgical procedure. Needle channel 124 runs longitudinally along at least a portion of proximal member 112. In one embodiment, channel 124 extends along the entire length of proximal member from a first end positioned proximal to the surgeon to a second end adjacent to intermediate member 116. In this embodiment, one or more needle(s) 118a, 118b, 118c, . . . and a needle pusher 126 and grip 136 can be inserted into and retrieved from channel 124 at the first end. In other embodiments, channel 124 extends only partly through the proximal member 112. Needle channel 124 can be centrally located along proximal member 112. In preferred embodiments, proximal member 112 includes a single needle channel 124 through which one, two, three, or more needles can be advanced. Alleviating multiple needle channels within the suturing device provides a more compact member, which can be particularly advantageous for subcutaneous procedures.

Channel 124 is sized and dimensioned to allow one or more needles 118a, 118b, 118c . . . to be advanceable therethrough and into vascular tissue around the puncture wound. Furthermore, channel 124 can be either partly or completely encased within the body of proximal member 112. However, in a preferred embodiment, channel 124 is not encased within the body of proximal member 112. Rather, channel 124 is provided as a slot formed into the surface of proximal member 112. Preferably the slot is configured to retain one or more needles within the slot. For example, the slot can be formed to have an opening at the exterior surface of proximal member that is narrower than the diameter of the needles (and optionally the pusher 126) while the internal portion or diameter of the slot can be dimensioned to permit facile movement of the needle therethrough. An exit opening is located at the distal end of channel 124.

Proximal member 112 includes a blood return line 125 that terminates in a fitting 127, for example, a luer lock that can be mated to a syringe. Alternatively, line 125 can terminate in a valve or shunt to control and stop blood flow therethrough. It is preferable that blood line 125 allow visible observation of blood originating from inside the vascular vessel. This can facilitate proper placement of the device for suturing.

Figure 24:
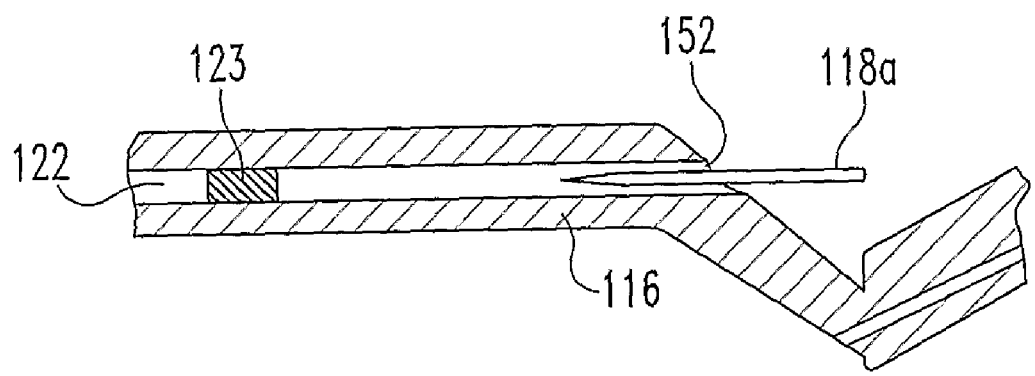
FIG. 24 is an enlarged view in cross section of the distal member of the suturing device of FIG. 23.
Figure 25:
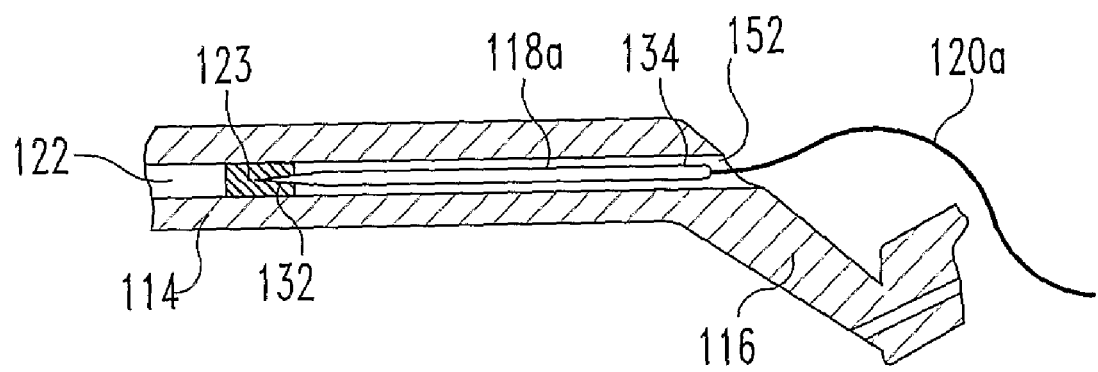
FIG. 25 is an enlarged view in cross section of the distal member of the suturing device of FIG. 23 with a needle disposed within a receptacle in the distal member.

Referring additionally to FIGS. 24 and 25, distal member 114 is sized and/or configured to be received within a lumen of a patient's vascular vessel similar to distal member 114. In additional embodiments, distal member 14 can be coated or impregnated with a lubricant, bioactive agent, such as an anticoagulant material, and the like. In certain embodiments, it is preferable that at least distal member 14 be formed of a flexible or elastomeric material that is biocompatible—particularly with blood. For example, distal member 14 can be composed of a biocompatible polymeric material commonly used for catheters, such as silicone rubber, polyethylene, polyolefin, polyurethane, polytetrafluoroethylene, polyvinyl chloride and the like.

Distal member 114 includes a receptacle 122 sized and configured to receive and retain at least one needle 118a, and preferably two or more needles 118b, 118c . . . Preferably, receptacle 122 is sized to retain one or more needles such that the proximal end of each of the needles does not extend beyond opening 152.

A needle catching element 123 located in receptacle 122 is provided to engage with at least a portion of needles 118a, 118b, 118c . . . Element 123 can be configured as a plug of pierceable material. The material can be any biocompatible material pierceable with a surgical needle. Representative examples include materials such as silicone rubber, polyethylene, or polyurethane. In certain embodiments, the plug of material is composed of the same material as that used to form the distal member. The plug of material can be friction fit, adhesively bound, or mechanically retained inside receptacle 122. In other embodiments, the plug of material can include a molded flap extending from an interior wall portion of receptacle 122. In still other embodiments, the needle catching element 123 can be integral with, or alternatively define, a bottom wall portion of receptacle 122. Needle capture element 123 can completely close off or block receptacle 122. In other forms, element 123 need not completely block receptacle 122.

Referring back to FIG. 23, distal member 14 can also include a lumen 139 extending at least partially therethrough. Preferably, lumen 139 is separate from receptacle 122. Lumen 139 can be provided to receive or follow a guide wire left in place after a particular diagnostic or treatment procedure. This can allow the facile insertion of distal member 114 into the patient's vascular vessel. In a preferred embodiment, lumen 139 exits through a side of distal member 114 at opening 140 to permit a guide wire (not shown) to extend out without interfering with the needles, needle path, or suture material. The guide wire can be removed after placement of the suture device or left in as desired or considered medically prudent by the surgeon.

Intermediate member 116 is located between proximal member 112 and distal member 114. Intermediate member 116 defines a tissue-receiving area 145. In the illustrated embodiment, intermediate member is configured to include an arcuate portion or a crooked section. The arcuate portion or crook can defines a concave interior surface 147 and a convex exterior surface 148. Intermediate member 116 includes a first opening 150 providing access from the channel 124 to the tissue receiving area 145 and a second opening 152 from the receptacle 122 providing to the tissue receiving area 145. Preferably, first and second openings 150 and 152 are linearly or axially aligned. Intermediate member 116 can be composed of a biocompatible material that is substantially resistant to deformation and therefore can maintain the linearity between channel 124 and receptacle/chamber 122 and the respective first and second openings 150 and 152. Examples of suitable materials include TEFLON, NYLON, polyamids, and the like.

Intermediate member 116 also includes means and structure for reliable positioning of the device during surgery to facilitate closing the vascular puncture wound with sutures. Part of the positioning structure includes an opening 154 providing fluid communication to blood return line 125 in proximal member 112. In a preferred embodiment, opening 154 is located on a portion of the convex surface 148 of the intermediate member 116 opposite the tissue receiving region 145. In use, with the distal member of the device suitably positioned within the lumen of a vascular vessel, opening 154 is also located in the interior of the lumen. This permits blood from the vessel to enter blood return line 125, which can then be visibly observed by the surgeon. If blood is not observed in blood return line 125, then the distal member may not have been inserted to a sufficient depth into the lumen of the vascular vessel.

Additionally, a ridge or stop 156 extends from the concave surface into the tissue receiving region. Stop 156 is configured to bear against vascular tissue adjacent the puncture wound. In a preferred embodiment, first opening 150 extends through a portion of stop 56 permitting needle 118 to pierce tissue adjacent thereto. Stop 156 is sized to bear against the vascular tissue and avert further insertion of the device 110 into the vascular vessel. When provided together, stop 156 and opening 150 with blood return line 125 cooperate to ensure accurate placement of the suturing device in the patient's vascular vessel. Ridge or stop 156 can also extend radially about the entire circumference of intermediate member 116.

FIG. 24 shows needle 118*a* entering opening 152 in distal member 114 and traversing receptacle 122 in response to distal movement of needle pusher 126.

FIG. 25 illustrates the capture of needle 118*a* within receptacle 122. Element 123 is positioned in receptacle 122 to engage with at least the distal tip 132 of needle 118*a*. Preferably element 123 is positioned at a location or depth within receptacle 122 such that the proximal end 134 of a captured needle does not extend out of opening 152 of receptacle 122 to snag on any tissue or other structure as the suturing device is manipulated and eventually removed from the vascular vessel.

Figure 26:
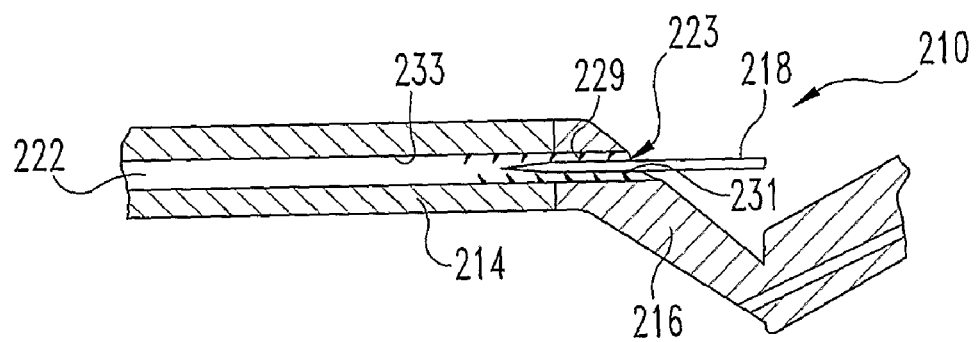
FIG. 26 is an enlarged view in cross section of an intermediate member with needle engaging projections of an alternative suturing device in accordance with the present invention.
Figure 27:
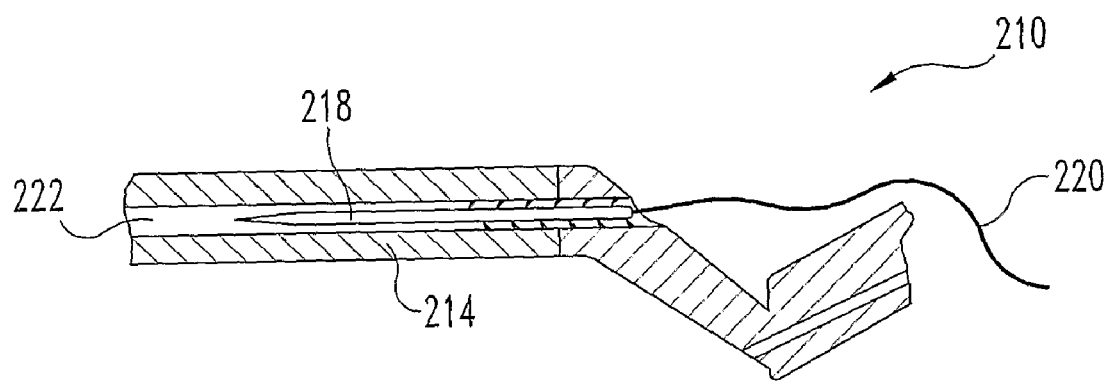
FIG. 27 is an enlarged view in cross section of the distal member illustrated in FIG. 26 with a needle disposed in the receptacle.

FIGS. 26 and 27 illustrate partial views of an alternative embodiment of a suturing device 210 with a needle capture element 223. The illustrated distal and intermediate members 214 and 216 are configured similarly to distal and intermediate members 114 and 116. However, distal member 214 includes a receptacle 222. Receptacle 222 is configured to receive one or more needles therein. Needle capture element 223 comprises at least one projection 229 and preferably at a second projection 231 each extending radially inwardly from an interior wall portion 233. It will be understood that receptacle 222 can include a plurality of projections similarly configured as illustrated and/or described for projections 229 and 231. The projections 229 and 231 are configured to engage and capture or retain one or more needles 218 within the interior of receptacle 222. The projections 229 and 231 can frictionally engage the tips or sides of inserted needles to prevent their accidental dislodgement during surgical manipulation. In the illustrated embodiment, projections 229 and 231 are configured as a plurality of paired leaves projecting from the interior wall portion 233 of receptacle 222. It will be understand that in other embodiments, the leaves need not be paired; or, if paired, the leaves can be axially and/or radially offset from each other. In still other embodiments, projections 229 and 231 can be configured as protuberances, bumps, ridges, or threads extending from an internal wall portion of receptacle 222 to engage and retain one or needles 218 therein. Further, one or more of needles 118*a*, 118*b*, and 118*c* can include a recessed surface configured for engagement with at least one of the projections 229 and 231. For example, a needle can be configured with a barbed point or alternatively with a tip similar to a tip as described in connection with FIGS. 1-22 above.

Referring specifically to FIG. 27, a needle 218 with a length of suture material 220 is illustrated as captured within lumen 222. As can be observed in the illustration, a plurality of projections 229 and 231 frictionally engage with the sides of the inserted needle 218. Preferably, the projections 229 and 231 are angled in the distal direction from their point of connection to wall 233 of receptacle 222. This causes the frictional engagement resisting needle movement in a proximal direction to be greater than the frictional engagement resisting a needle movement in a distal direction. This engagement effectively prevents the inserted needle 218 from being dislodged by manipulation of suturing device 210 within the patient or upon withdrawing the suturing device from the vascular vessel.

Figure 28:
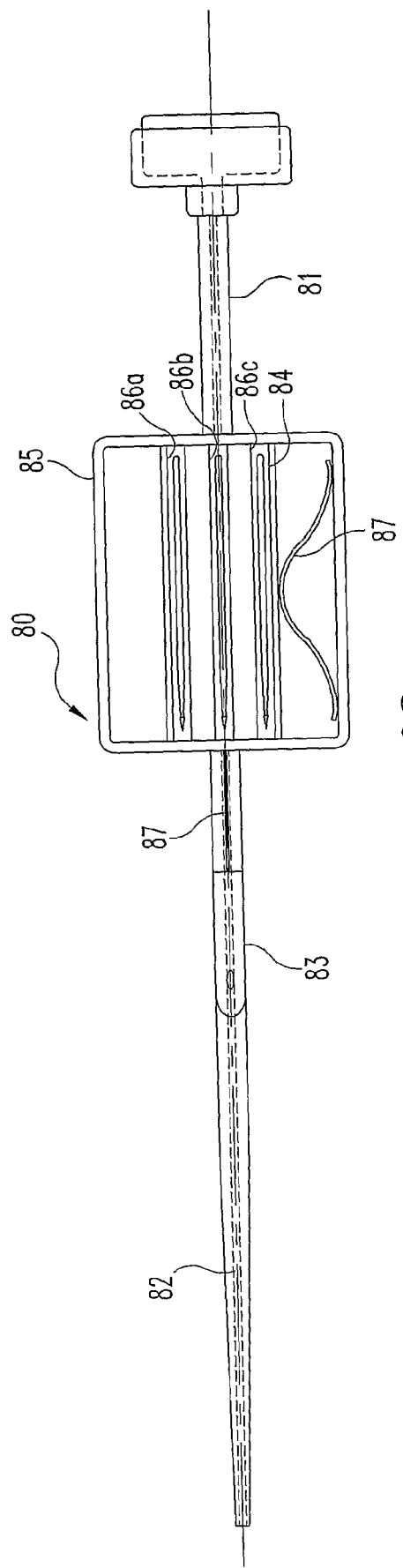
FIG. 28 is a plan view of an alternative embodiment of a suturing device with a needle cartridge for use in accordance with the present invention.
Figure 29:
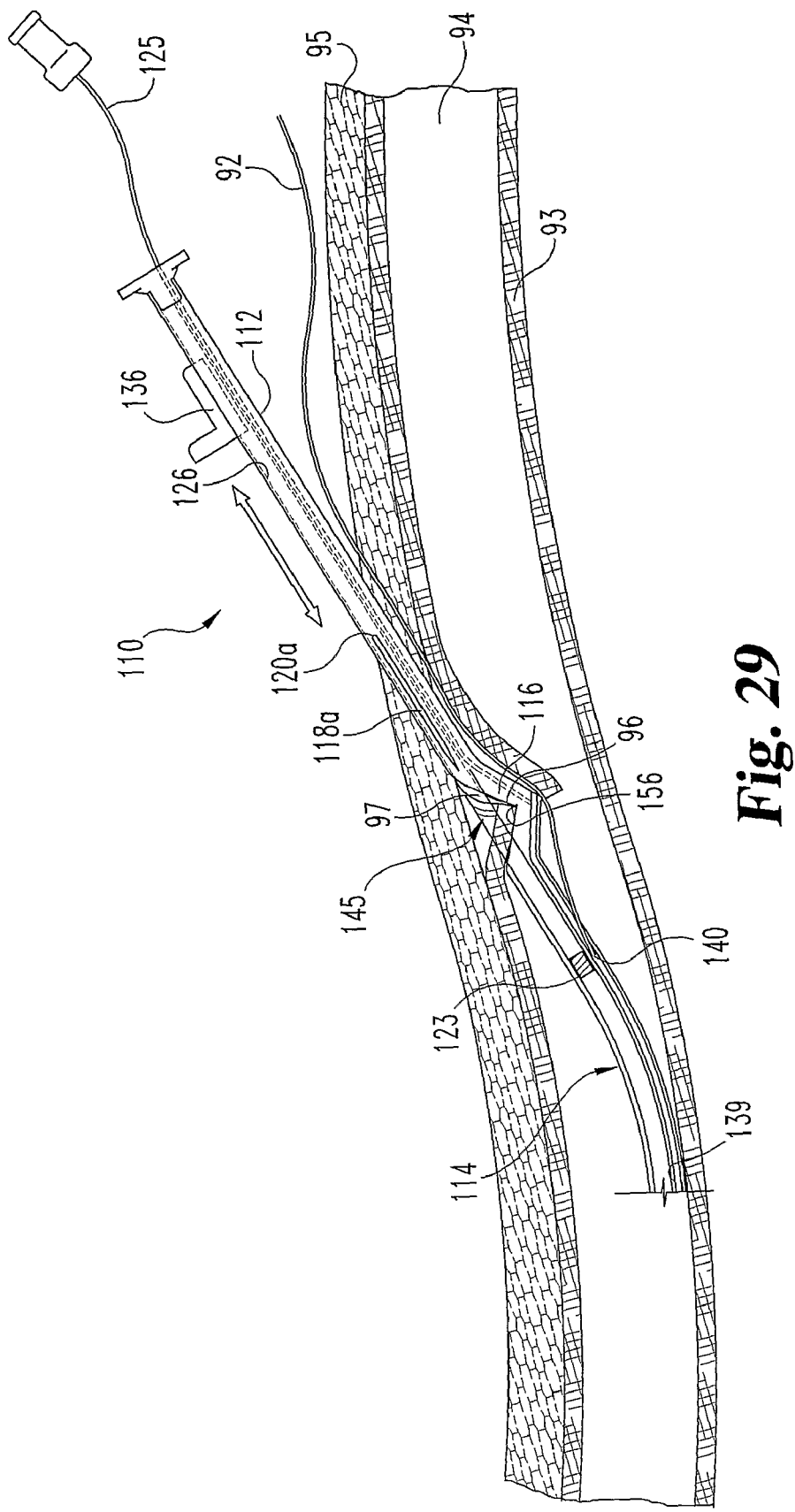
FIGS. 29-34 illustrate methods of use of the suturing device according to the present invention.

FIG. 28 is a perspective view of another embodiment of a suturing device 80 with a needle cartridge in accordance with the present invention. Device 80 includes a proximal member 81, a distal member 82, and an intermediate member 83 therebetween. Proximal member 81 includes a needle cartridge 84 slidably mounted in body 85. Needle cartridge 84 can include a plurality of needle slots, for example, two, three, four, or more slots 86*a*, 86*b*, 86*c* . . . , each for a separate needle. Each needle in needle cartridge 84 is individually advanceable through a central needle channel along a length of proximal member 81. Needle cartridge 84 is slidably disposed within body 85 to axially align the selected needle slot 86*a*, 86*b*, 86*c* . . . with a single needle channel 87. If desired, needle cartridge 84 can be biased to automatically align the successive needle slots with the needle channel after the preceding needle has been advanced along the channel. Alternatively, suturing device 80, body 85, and/or cartridge 84 can include one or more of ratchetings, positive stops, or locks to individually align the desired needle slot with the channel. In other embodiments, needle cartridge 84 can be provided as a revolving barrel that can hold two, three, or more needles in respective needle slots radially disposed about the barrel. The barrel can be rotatably mounted on or about proximal member 81. Distal member 82 and intermediate member 83 can be configured substantially as described above for members 114 and 116, respectively.

FIGS. 29 through 34, illustrate the use of suturing device 10 for closure of a puncture wound 96 in a vascular vessel 93. A puncture wound in a vascular vessel can be sutured closed using the suturing device 110. Suturing device 110 can be inserted distally into the vascular vessel. This can be accomplished with or without the use of a guide wire. In a procedure where a guide wire has been previously used, suturing device can be threaded onto a guide wire 92 which extends from internal vessel lumen 94 through vessel 93 and a portion of the overlying tissue 95 to be exposed to the surgeon. In that regard, opening 140 of lumen 139 can be threaded onto guide wire 92 which then extends out through opening 140. Thus, the flexible portion of distal member 114 can be gingerly threaded into the lumen 94 of vessel 93. The distal member 114 of device 110 can be positioned within lumen 94 such that intermediate member 116 engages with a portion of the tissue surrounding puncture 96. Distal member 114 is advanced in a distal direction until blood is observed in blood return line 125. Additionally, when provided, stop 156 abuts or bears against the external surface of the vascular vessel. This can be detected by the increased resistance to further advancement of the device in the distal direction. Both blood return line 125 and stop 156 can be used to ascertain that the device has been correctly positioned within the lumen 94 of the vascular vessel 93 to allow suturing of puncture 96. It should be noted that observance of blood in needle channel 124 is an indication that device 110 has been inserted too far into the lumen 94 such that first opening 150 is exposed to the interior or blood side of vessel 93. If desired, guide wire 92 can then be withdrawn from lumen 139 and out of vascular vessel 93—if it is no longer needed for subsequent procedures.

After the distal member is positioned as desired, the vascular tissue adjacent the puncture wound is received within the tissue receiving area 145. As noted above, intermediate member 116 provides an essentially linear needle pathway between needle channel 124, receptacle 122, and the vascular tissue in the tissue receiving area 145. Consequently, when needle 118a is advanced through channel 124, it pierces the vascular tissue 93 at a first suture site 97 adjacent the puncture wound 96.

Figure 30:
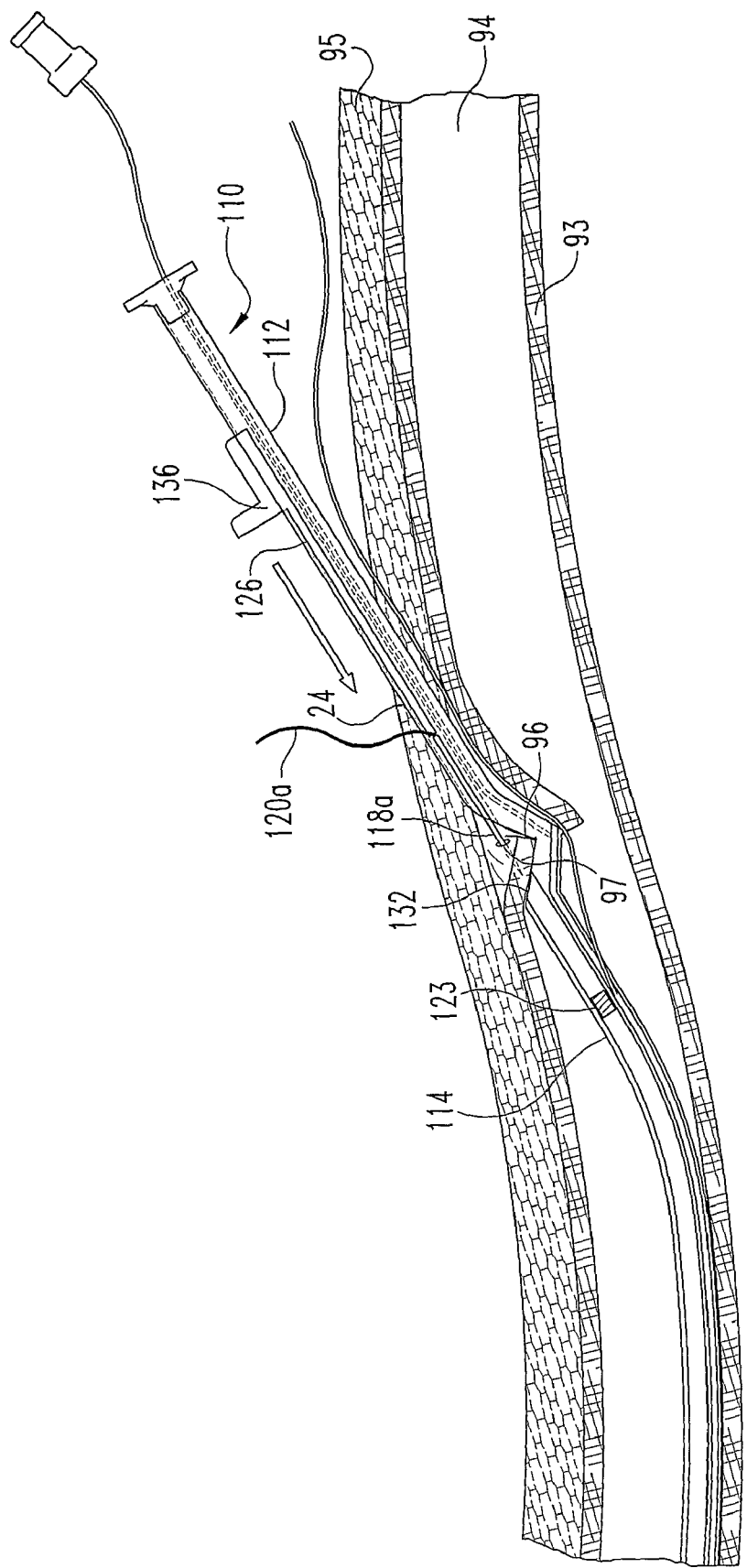

FIG. 30 illustrates suturing device 10 at a first suture position. Intermediate member 116 provides an essentially linear needle pathway between channel 124 and receptacle 122. A first needle 118a advancing through channel 124 using needle pusher 126 pierces vascular tissue in tissue receiving area 145 at the first suture site 97. Needle 118a trails a length of suture material 120a pulling it through the vascular at suture site 97 adjacent wound 96. From there, needle tip 132 is advanced into to receptacle 122 to engage needle capture element 123. Thereafter, needle 118a and optionally a portion of the suture material 120 are inserted into receptacle 122 where at least a portion of the needle 118a engages with needle capture element 123. Needle capture element 123 reliably retains needle 118a within receptacle 122 during the rest of the suturing procedure or until the surgeon decides to withdraw the needle.

Figure 31:
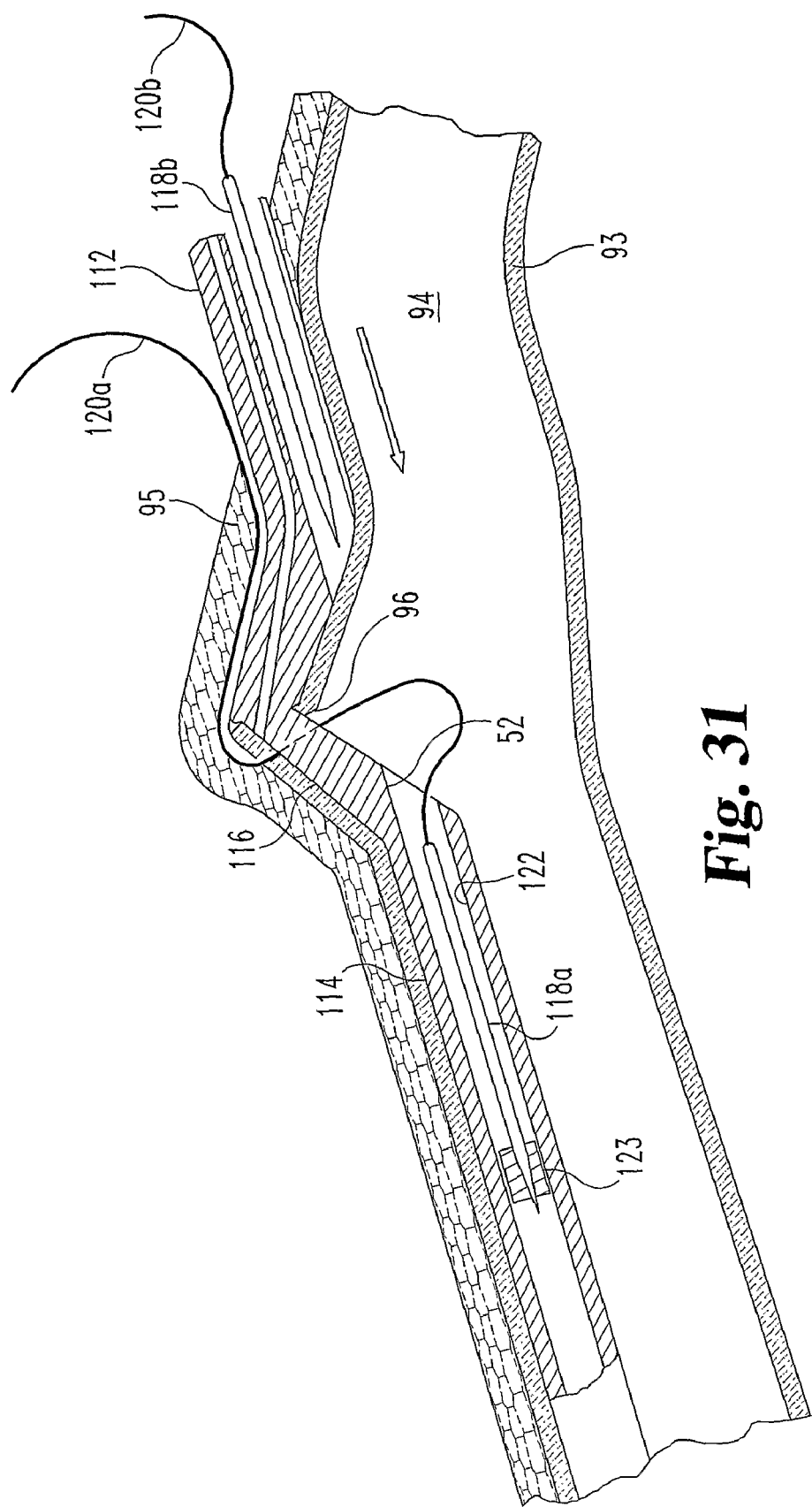

As shown in FIG. 31 suturing device 110 is rotated into a second suture position. Suture device 110 can be rotated approximately 180° so that in the second suture position, suture device 110 is positioned to operate on a second side of wound 96 diametrically opposite first suture site 97.

Figure 32:
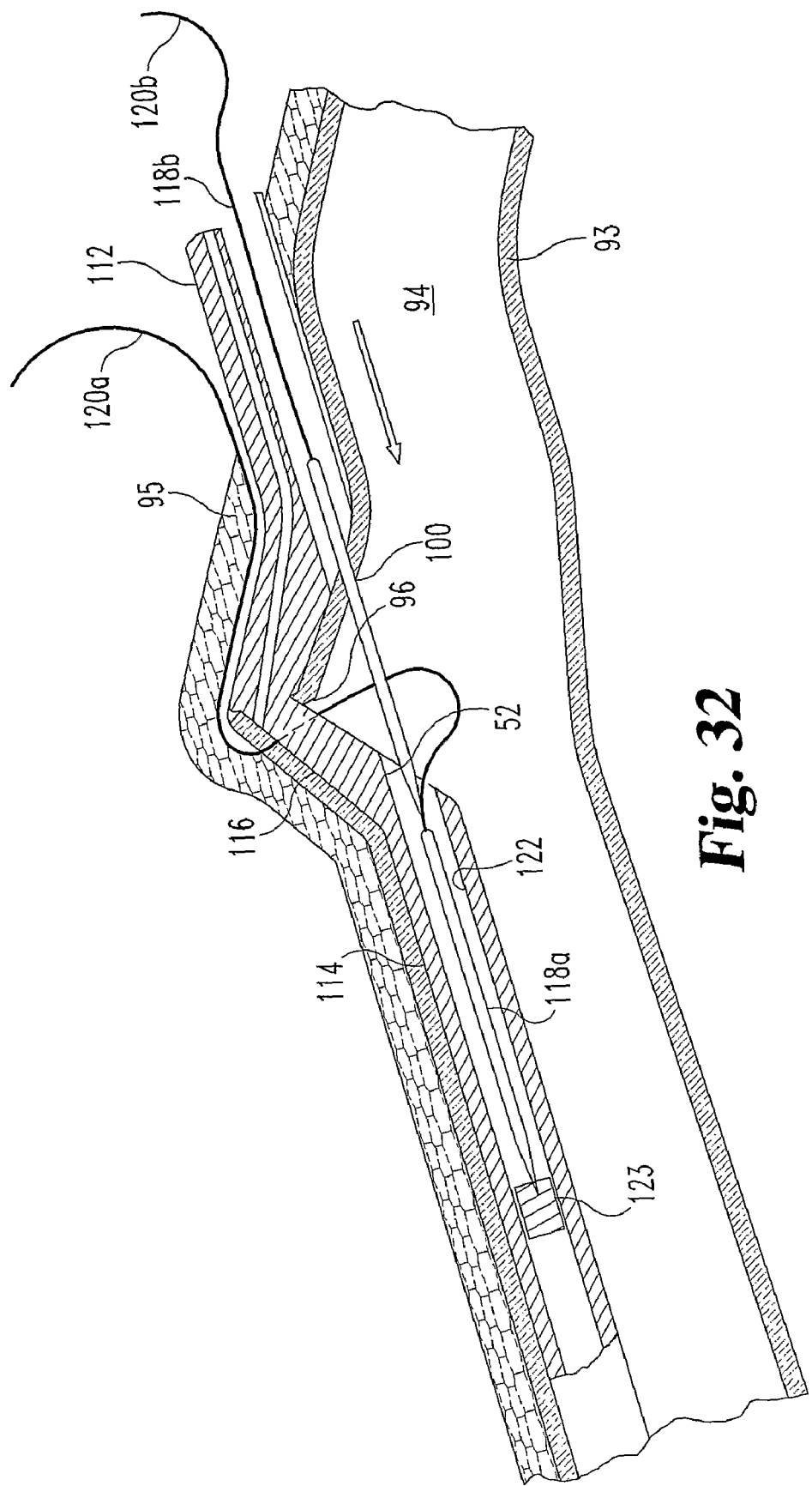

FIG. 32 illustrates suturing device 110 in the second suture position. A second needle 118b can be advanced through or along receptacle 122 using the needle pusher 126, either the same needle pusher or a second, different needle pusher. Needle 118b exits first opening 150 to pierce vascular tissue received in the tissue receiving area 145 at a second suture site 100. Continuing the advancement of needle 118b through the needle path draws the attached suture material 120b through second suture site 100 adjacent wound 96. Thereafter at least a portion of needle 118b is captured and retained by needle capture element 123 within receptacle 122. If desired, suturing device 110 can again be repositioned to draw suture material through a third and any desired subsequent suturing sites. It will be understood that suture material 120a and 120b can be opposite ends of the same piece of suture material. Alternatively, suture material 120a and 120b can be two separate lengths of suture material.

Figure 33:
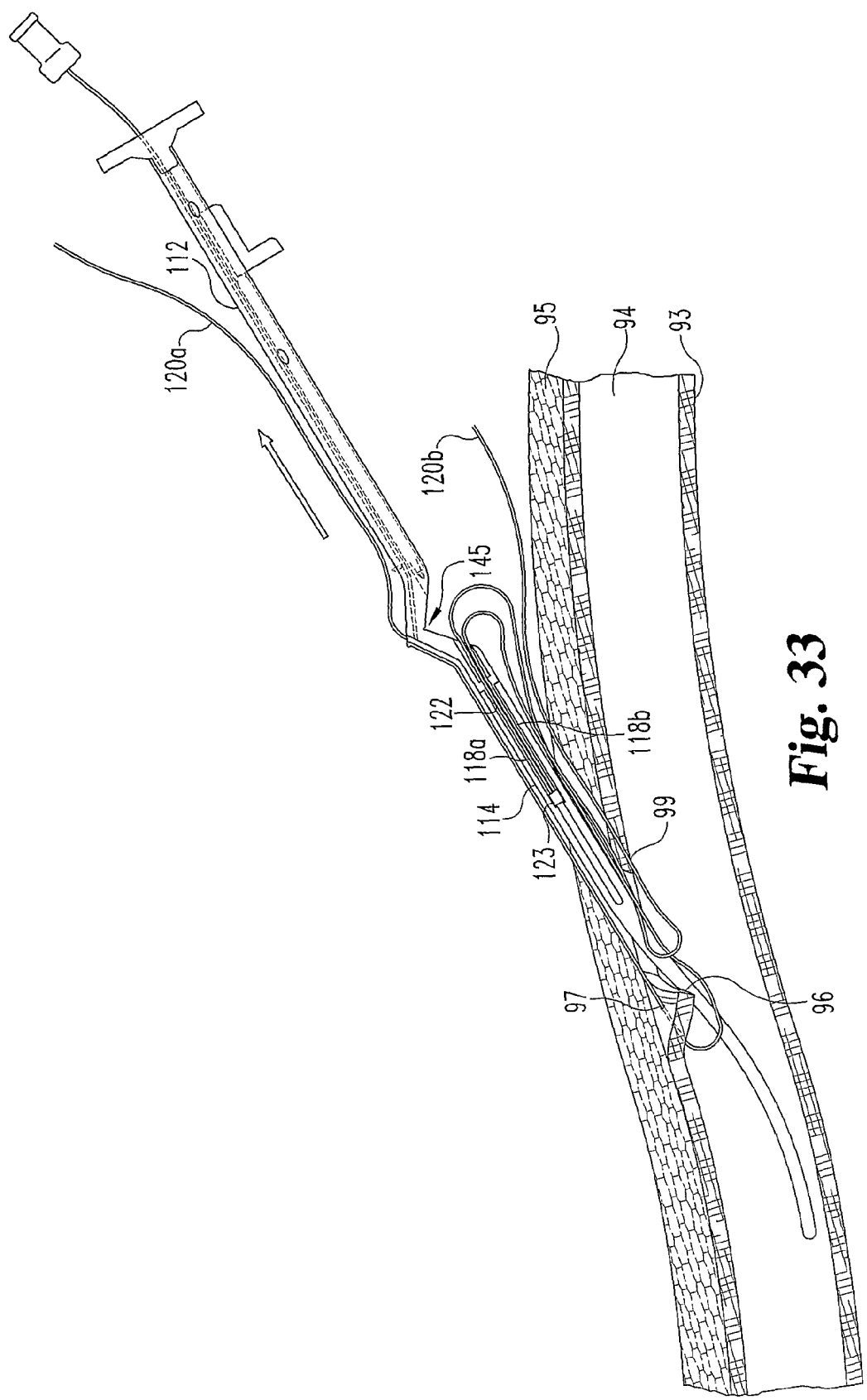

FIG. 33 illustrates device 110 being removed in a distal direction from vascular vessel 93. As suture device 110 is withdrawn in the distal direction, needles 118a and 118b remain embedded within the needle catching element 123 in receptacle 122. Consequently, the attached lengths of suture material 120a and 120b are pulled in a distal direction through the vascular tissue at the first and second suture sites 97 and 100, respectively and then out through the wound 96. One implementation of the suturing device can be a common length of suture material 120 attached to the proximal ends of needles 118a and 118b. As illustrated in FIG. 12, the resulting suture path extends from the proximal side of vessel 94 across the wound opening and through the first and second suture sites 97 and 100 into the lumen 94. The suture material 120 then extends out through wound opening 96 back to the distal side of vessel 93.

Figure 34:
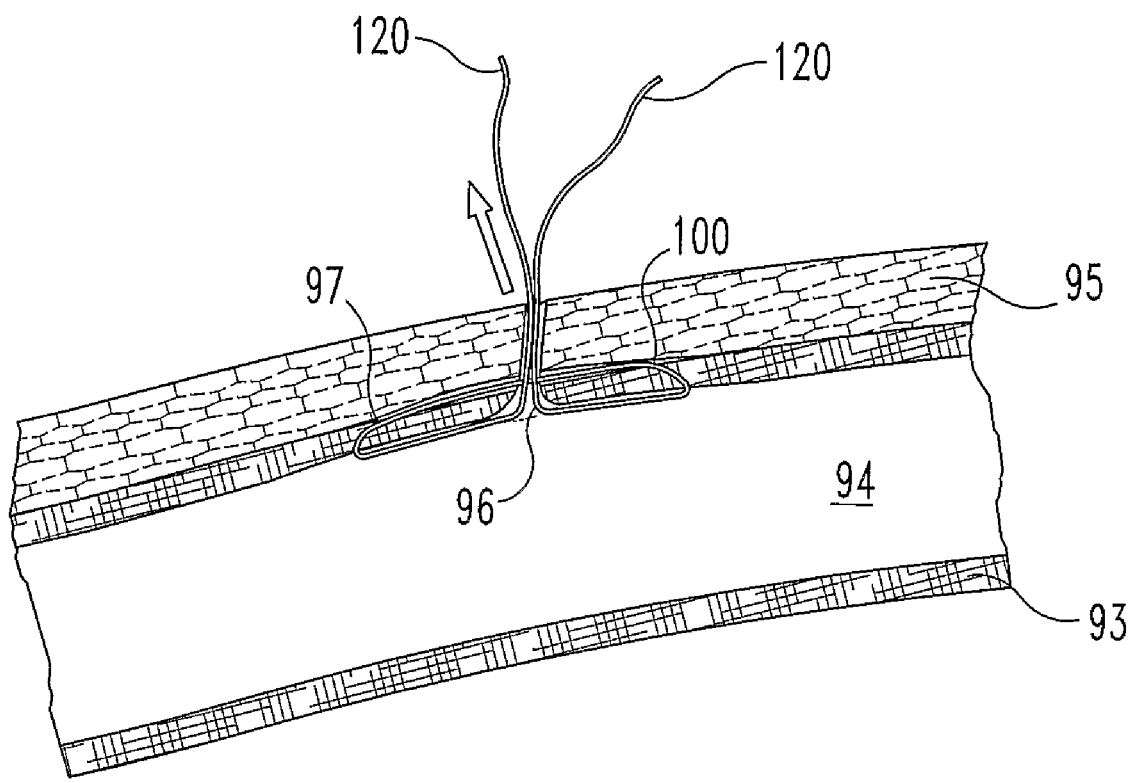

FIG. 34 depicts wound closure. The free ends of the suture material 120 can be gathered and a suture knot tied. As with the other procedures described above, a knot pusher 115, knot boxes as described in WO 01/19258, and knot replacement technologies (see FIGS. 13 and 14) can be used to close the wound and secure the suture material. The lengths of suture material can be gathered. The length of suture material can be separated from the needles. Pulling the lengths of suture material taut closes the wound in the vessel. A surgical knot can be tied securing the wound closure. A knot pusher, for example, the knot pushers described in U.S. Pat. No. 5,304,184 issued to Hathaway et al., U.S. Pat. No. 5,746,755 issued to Wood et al., and U.S. Pat. No. 6,132,439 issued to Kontos, can be used to advance the loosely tied knot to the exterior surface of the vascular vessel. In selected embodiments, the surgeon can then tie a suitable surgical knot using the respective lengths of suture material to close the puncture wound 96.

In other embodiments, the suture material can be secured using a variety of knot replacement technologies such as that disclosed in U.S. patent application Ser. No. 10/164,606 (US Patent Publication No. 2003/0229377) and in Ser. No. 10/305,923 (US Patent Publication No. 2004/0102809) and depicted in FIGS. 13 and 14. Each of the above-noted references are incorporated by reference in their entirety.

Figure 35:
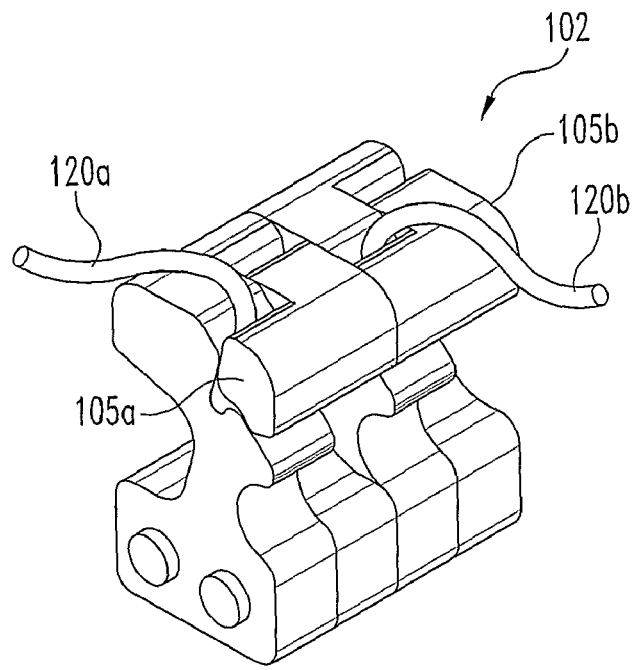
FIG. 35 is a perspective view of one embodiment of a suture securing device for use in the present invention.

FIG. 35 is a perspective view a suturing securing device 102 for use in the present invention. Suture securing device 102 is described and illustrated in US Patent Publication No. 2004/0102809 which is incorporated herein by reference. In use device 102 can secure ends of one, two, three or more lengths of suture material. Two lengths of suture material 120a and 120b are illustrated with device 102. The lengths of suture material are threaded into the flexible elements 105a and 105b which are then locked or fixed together securing the suture material therein.

Figure 36:
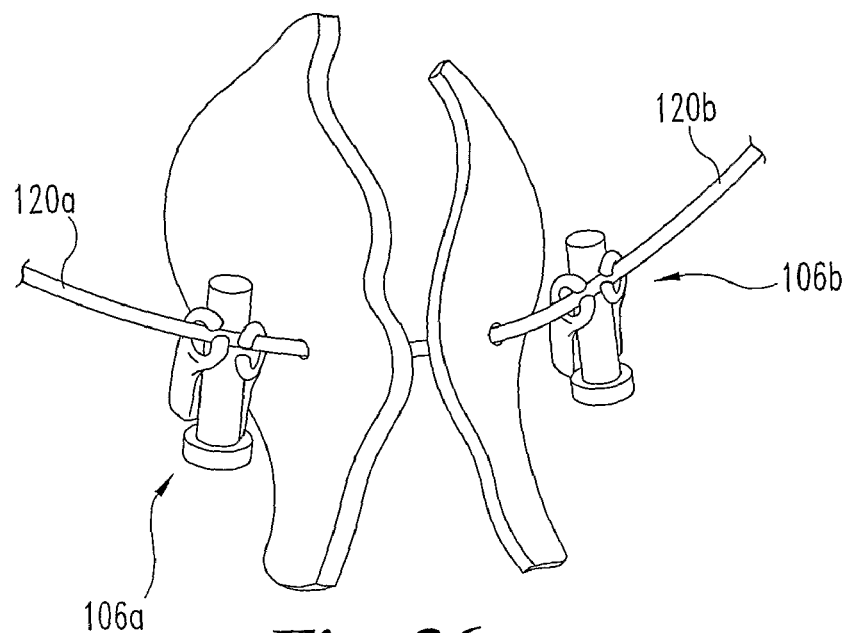
FIG. 36 is a perspective view of an alternative embodiment of a suture securing device for use in the present invention.

FIG. 36 is another embodiment of suture securing devices 106a and 106b for use in the present invention. Devices 106a and 106b are described in US Patent Publication No. 2003/0229377 which is incorporated herein by reference in its entirety. Devices 106a and 106b cooperate by separately clipping onto a selected length of suture material 104a or 104b which have previously pulled taut to close wound or complete the surgical procedure. The devices prevent the suture material from regressing back through the sutured tissue.

Figure 37:
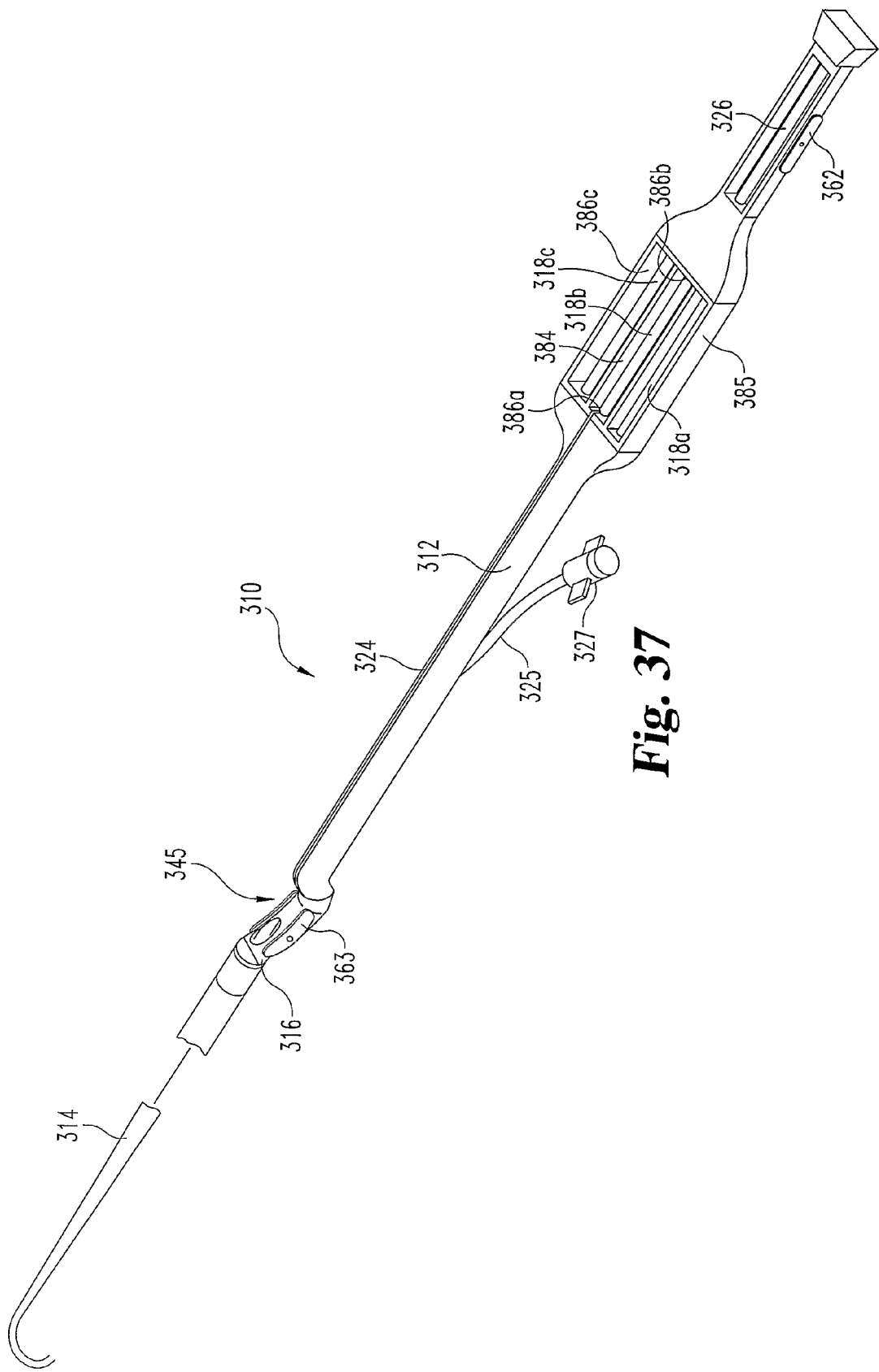
FIG. 37 is a perspective view of one embodiment of a suturing device with an articulating foot according to the present invention.
Figure 38:
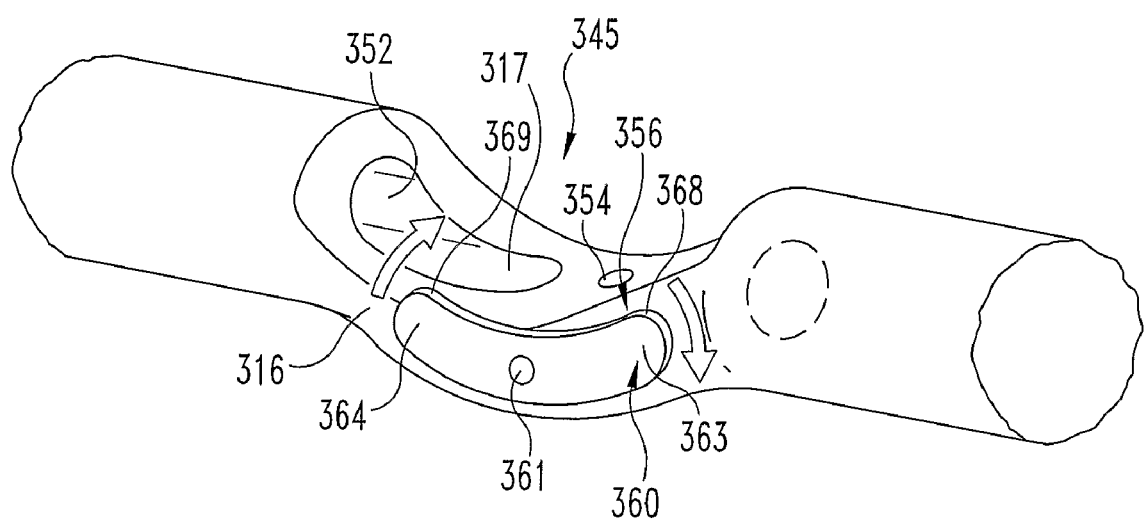
FIG. 38 is an enlarged fragmentary view of the intermediate member of the suturing device illustrated in FIG. 37.

FIGS. 37 and 38 illustrate another embodiment of a suturing device 310 for use in the present invention. Suturing device 310 includes a proximal member 312, a distal member 314, and an intermediate member 316 disposed therebetween. Proximal member 312 is provided as an elongated portion and can exhibit a substantially cylindrical or oval radial cross section. Member 312 includes a first end of sufficient dimensions to be readily grasped by the surgeon to manipulate the device during the procedures. Proximal member 312 can also include a gripping portion to facilitate handling during the surgical procedure. A needle channel 324 runs longitudinally along at least a portion of proximal member. In one embodiment, channel 324 extends along the entire length of proximal member from a first end positioned proximal to the surgeon to a second end adjacent to intermediate member 316. In this embodiment, one or more needle(s) 318 and needle pusher(s) 326 can be inserted into and retrieved from channel 324 at the first end. In other embodiments, channel 324 extends only partly through the proximal member 312. Needle channel 324 can be centrally located along proximal member 312. In preferred embodiments, proximal member 312 includes a single needle channel 324 through which one, two, three, or more needles can be advanced. Alleviating multiple needle channels within the suturing device provides a more compact member, which can be particularly advantageous for subcutaneous procedures.

As used herein, the term "proximal" refers to a direction toward the surgeon and away from the patient or a location closer to the surgeon, while the term "distal" refers to a direction towards the patient and away from the surgeon or a location closer to the patient.

Channel 324 is sized and dimensioned to allow one or more needles 318 to be advanceable therethrough and into vascular tissue around the puncture wound. Furthermore, channel 324 can be either partly or completely encased within the body of proximal member 312. However, in a preferred embodiment, channel 324 is not encased within the body of proximal member 312. Rather, channel 324 is provided as a slot formed into the surface of proximal member 312. Preferably the slot is configured to retain one or more needles within the slot. For example, the slot can be formed to have an opening at the exterior surface of proximal member that is narrower than the diameter of the needles (and, optionally, the pusher) while the internal portion or diameter of the slot can be dimensioned to permit facile movement of the needle therethrough. An exit opening is located at the distal end of channel 324.

Proximal member 312 includes a blood return line 325 that terminates in a fitting 327, for example, a luer lock that can be mated to a syringe. Alternatively, line 325 can terminate in a valve or shunt to control and stop blood flow therethrough. It is preferable that blood line 325 allow visible observation of blood originating from inside the vascular vessel. This can facilitate proper placement of the device for suturing.

Suturing device 310 comprises a needle cartridge 384 slidably mounted in a body 385 disposed on proximal member 312. Needle cartridge 384 can include two, three, four or more needle slots 386a, 386b, and 386c . . . for needles 318a, 318b, 318c, . . . Each of needles 318a, 318b, 318c, in needle cartridge 384 is individually advanceable through a central needle channel 324 along a length of proximal member 312. Needle cartridge 384 is slidably disposed within body 385 to axially align the selected needle slot 386a, 386b, 386c with needle channel 324. If desired, needle cartridge 384 can be biased to automatically align the successive needle slots with channel 324 after the preceding needle has been advanced. Alternatively, body 385 and/or cartridge 384 can include one or more of ratchetings, positive stops, or locks to align the desired needle slot with channel 324. In other embodiments, needle cartridge 384 can be provided as a revolving barrel that can hold two, three, or more needles in respective needle slots radially disposed about the barrel. The barrel can be rotatably mounted on or about proximal member 312.

A needle pusher 326 can either push or engage needle 318 to advance it through a channel 324 in the proximal member and through vascular tissue adjacent the puncture wound. In a preferred embodiment, needle pusher 326 in conjunction with needle cartridge can be configured such that the surgeon can sequentially advance needles 318a, 318b, and 318c, . . . in a proximal direction towards the patient.

Each of needles 318a, 318b, 318c, . . . can be attached to a length of suture material prior to be being loaded into the needle cartridge. The length of suture material can be attached adjacent to either the distal end of the proximal end. Preferably, the length of suture material is attached adjacent to the proximal end. In another embodiment, a single length of suture material is attached at one end to a first needle and at a second end to a second needle. The distal end of the needle can be configured to pierce tissue such as vascular tissue. The distal end can taper to a point, be configured as a barbed tip or include recessed surfaces to engage in either fittings or the needle capture elements. Examples of needles with recessed surfaces are illustrated and described in connection with FIGS. 1-22 above and examples of needles suitable for use with a needle capture element are illustrated and described in connection with FIGS. 23-36 above. The proximal end 34 of needle can be free and configured to be handled by a surgeon. Alternatively, proximal end can be engageable or secured to needle pusher 326. In a preferred embodiment, needle pusher 326 is configured such that the surgeon can sequentially advance needle 318 in a proximal direction towards the patient and in a distal direction away from the patient.

Suturing device 310 includes distal member 314. In certain embodiments, distal member 314 and/or proximal member 312 is/are linear and define a longitudinal axis. Distal member 314 is sized and/or configured to be received within an opening or wound to a lumen of a patient's vascular vessel. Therefore, it is preferable that at least distal member 314 be formed of a flexible or elastomeric material that is biocompatible—particularly with blood. In additional embodiments, distal member 314 can be coated or impregnated with a lubricant, bioactive agent, such as an anticoagulant material, and the like. In certain embodiments, distal member 314 is composed of a biocompatible polymeric material commonly used for catheters, such as silicone rubber, polyolefin polyurethane, polytetrafluoroethylene, and the like.

Referring specifically to FIGS. 38 and 39, intermediate member 316 is positioned between proximal member 312 and distal member 314. Intermediate member 316 is configured to include an arcuate portion or a crooked section 317. An articulating foot 360 is pivotally secured to intermediate member 316 via pivot pin 361. Preferably, foot 360 is adjacent to the tissue receiving area 345 defined by intermediate member 316. Lever 362 located axially on proximal member 312 operates to position foot 360 between a first, non-deployed position to a second, deployed position back again to the first, non-deployed position (see FIGS. 42 and 43). In certain embodiments, foot 360 is symmetric about pivot pin 361 extending in both the proximal direction and the distal direction the about the same length—measured from the center of pivot pin 361. In other embodiments, foot 360 is asymmetric in the longitudinal direction in that either the proximal end 363 or the distal end 364 extends further from pivot pin 361 than the other end. It will also be understood that proximal end 363 can, but need not, be the mirror image of distal end 364. (See FIG. 42.)

Intermediate member 316 also includes means and structure for reliable positioning of the device during surgery to facilitate closing the vascular puncture wound with sutures. Part of the positioning structure includes an opening 354 providing fluid communication to blood return line 325 in proximal member 312. In a preferred embodiment, opening 354 (see FIG. 40) is located on a portion of the convex surface of the crook opposite the tissue receiving region. In use, with the distal member of the device suitably positioned within the lumen of a vascular vessel, opening 354 is also located in the interior of the lumen. This permits blood from the vessel to enter blood return line 325, which can then be visibly observed by the surgeon. If blood is not observed in blood return line 325, then the distal member may not have been inserted to a sufficient depth into the lumen of the vascular vessel.

Additionally, a ridge or stop 356 extends from the concave surface into the tissue receiving region. Stop 356 is configured to bear against vascular tissue adjacent the puncture wound. In a preferred embodiment, first opening 350 extends through a portion of stop 356 permitting needle 318 to pierce tissue adjacent thereto. Stop 356 is sized to bear against the vascular tissue and avert further insertion of the device 310 into the vascular vessel. When provided together, stop 356 and opening 354 (with blood return line 325) cooperate to ensure accurate placement of the suturing device in the patient's vascular vessel. Ridge or stop 356 can also extend radially about the entire circumference of intermediate member 316.

Referring now to FIGS. 39 and 40, foot 360 is illustrated as nesting within a depression 365 formed in the lateral surface 366 of intermediate member 316. In this embodiment, foot 360 is configured to provide or complete the circular or oval radial external profile of member 316 to facilitate insertion and use of the device to suture wounds in vascular vessel.

Figure 41:
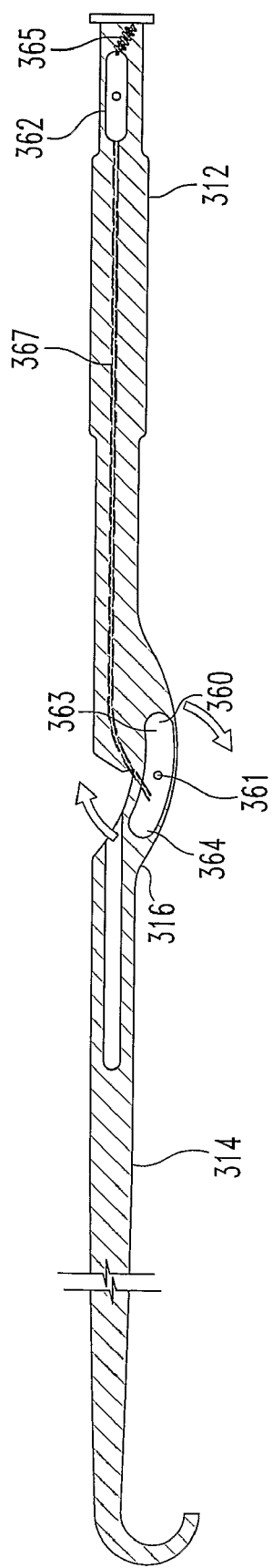
FIG. 41 is a longitudinal cross-sectional view along section 41-41 of the suturing device illustrated in FIG. 40 illustrating the intermediate member with the articulating foot in a non-deployed position.

FIG. 41 is a cross-sectional view of suturing device 310. Foot 360 can be controlled or deployed by lever 362 using cable 367 that extends from foot 360 through an interior channel or lumen in member 312 to connect to one end of lever 360. Foot 360 can, but need not, include a biasing element such as a spring 365 to either urge foot to reside in the first deployed position or the second non-deployed position. As illustrated, spring 365 urges lever 362 and foot 360 to a non-deployed position. It will be understood that cable 367 can also extend along side of member 312 without requiring a separate channel or lumen.

Figure 42:
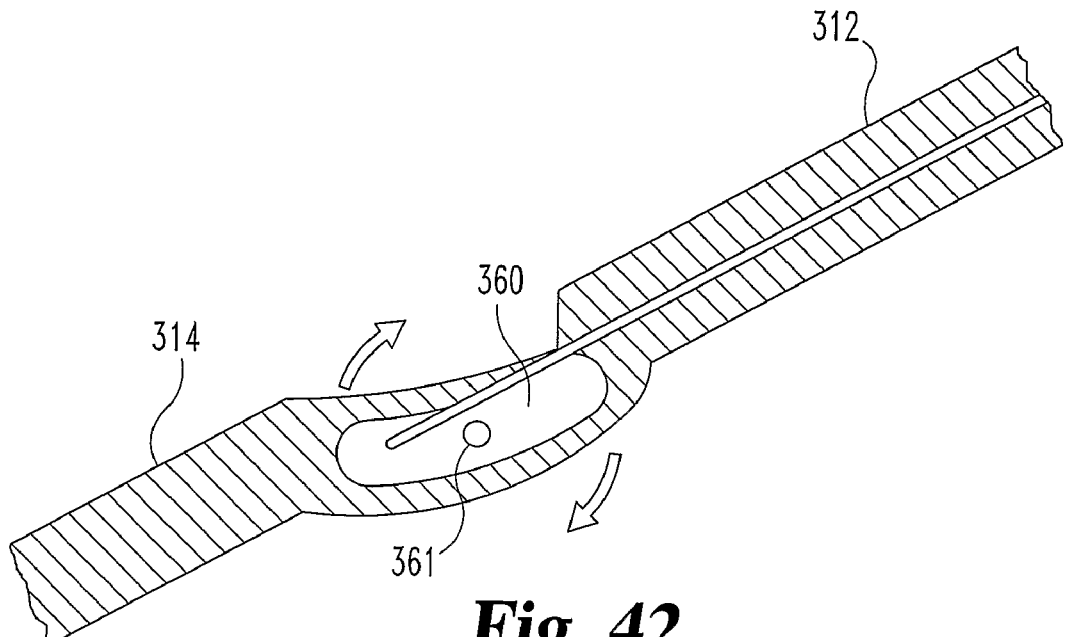
FIG. 42 is a fragmentary cross-section view of the suturing device illustrated in FIG. 37 with the foot in a first, non-deployed position.
Figure 43:
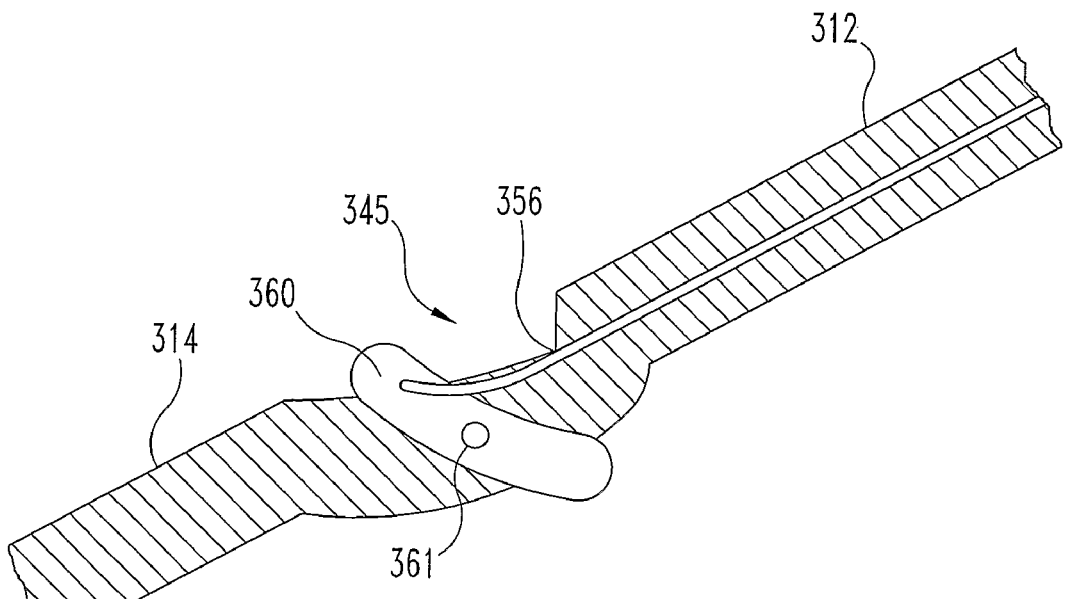
FIG. 43 is a fragmentary cross-section view of the suturing device illustrated in FIG. 37 illustrating the intermediate member with the articulating foot in a second or deployed position.
Figure 44:
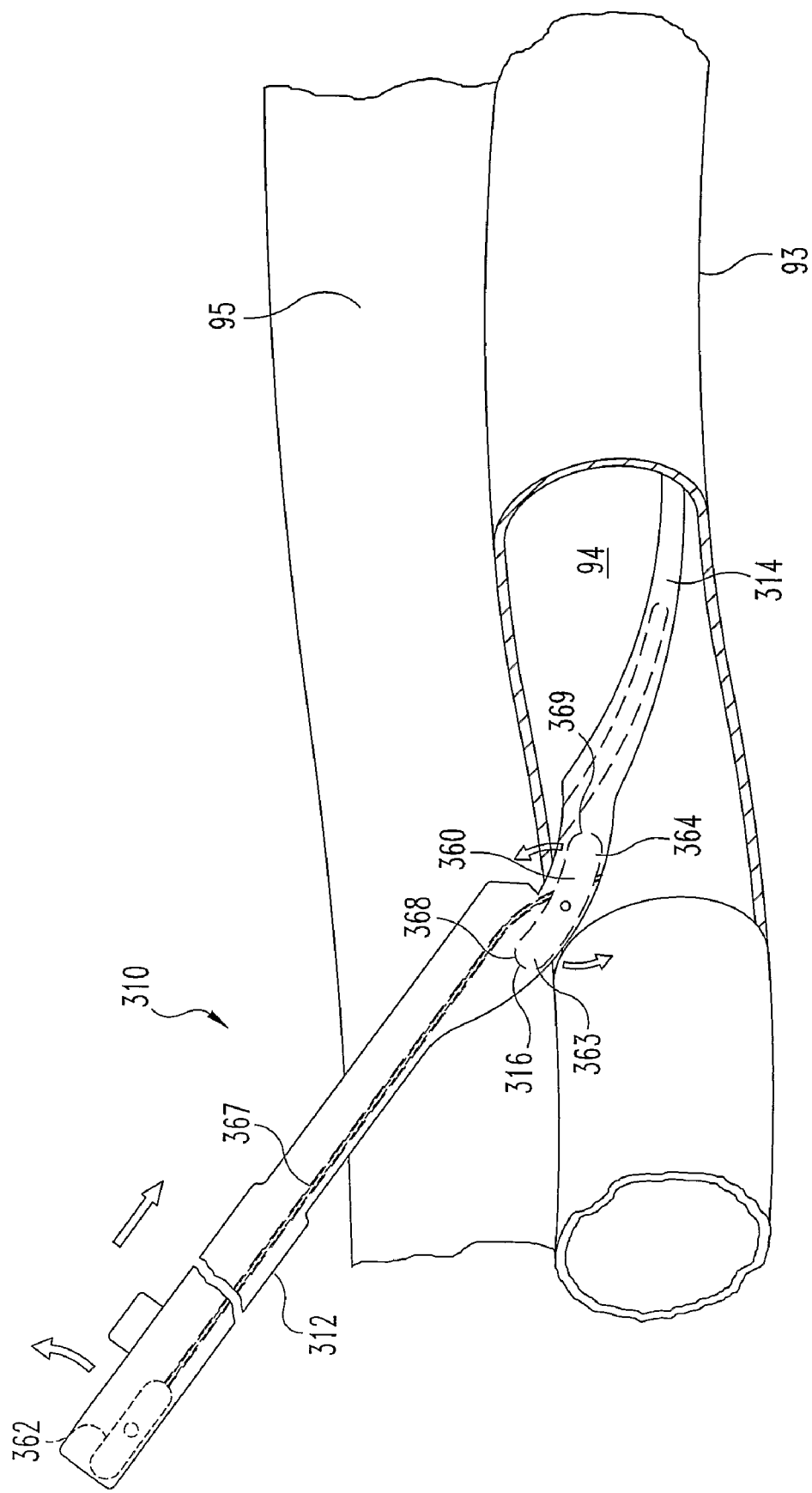
FIGS. 44-47 illustrate use of the suturing device of FIG. 37.

FIG. 42 illustrates intermediate member 316 with foot 360 in a non-deployed position. Movement of lever 362 causes foot 360 to rotate about pin 361 to a deployed position to support the vascular tissue from inside the vessel lumen as illustrated in FIG. 43. It should be apparent to those skilled in the art that a variety of mechanical interconnections may be used to translate the movement of lever 362 into rotation of foot 360 about end 361. In addition to the cable connection 367, it may be possible to employ a rack which engages a cog on foot 360 so that when the rack is displaced longitudinally the foot 360 rotates from the non-deployed to the deployed condition.

FIGS. 44 through 47 illustrate use of suturing device 310 in accordance with the present invention. Distal end 314 of suturing device 310 can be initially inserted into a vascular vessel 94. For this procedure it will be understood that device 310 includes the blood return line 325, opening 352 and stop 356 for device 10 that operate in cooperation to ensure accurate placement of the suturing device in the patient's vascular vessel. However for the purposes of clarity, these elements have not been illustrated in the present drawing.

Figure 45:
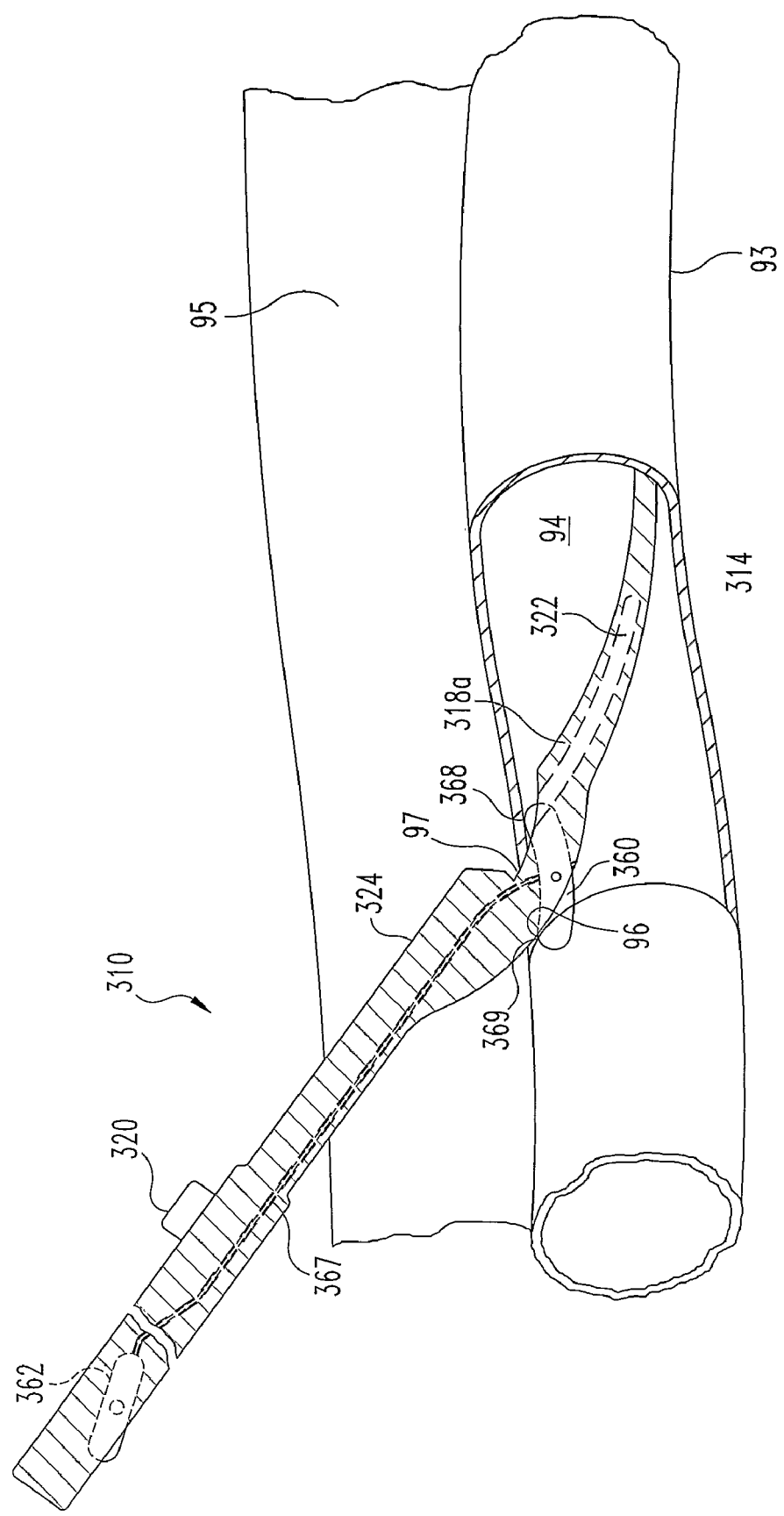

Once distal member 314 and at least a portion of intermediate member 316 have been inserted into the vascular vessel as desired, foot 360 can be deployed. In certain embodiments, intermediate member 316 is inserted sufficiently deeply (distally) into the lumen 93 of vessel 94 so that the foot 360 is completely enveloped within the interior of lumen 93 to facilitate deployment of foot 360. This positioning allows facile deployment of foot 360 such at the tissue engaging surfaces 368 and 369 of ends 363 and 364, respectively readily support and bear against inner or distal vascular tissue adjacent the wound 96 without catching on vascular tissue surrounding the wound. Deployment lever 362 on proximal member 312 can be pivotally rotated urging the cable 367 to deploy foot 360. Once foot 360 has been fully deployed, the suturing device 310 can be withdrawn in the proximal direction, if necessary, to allow the upper surfaces 368 and 369 of the foot to support and even exert slight pressure on the internal tissue of the vascular vessel as shown in FIG. 45. Thereafter, a needle 318a can be advanced though a needle channel 324 in proximal member 312 using needle pusher 326 to pierce vascular tissue adjacent the wound 96 at a first puncture site 97 and into receptacle 322. Needle 318a can remain within receptacle 322 during further manipulation of the device during wound closure.

Figure 46:
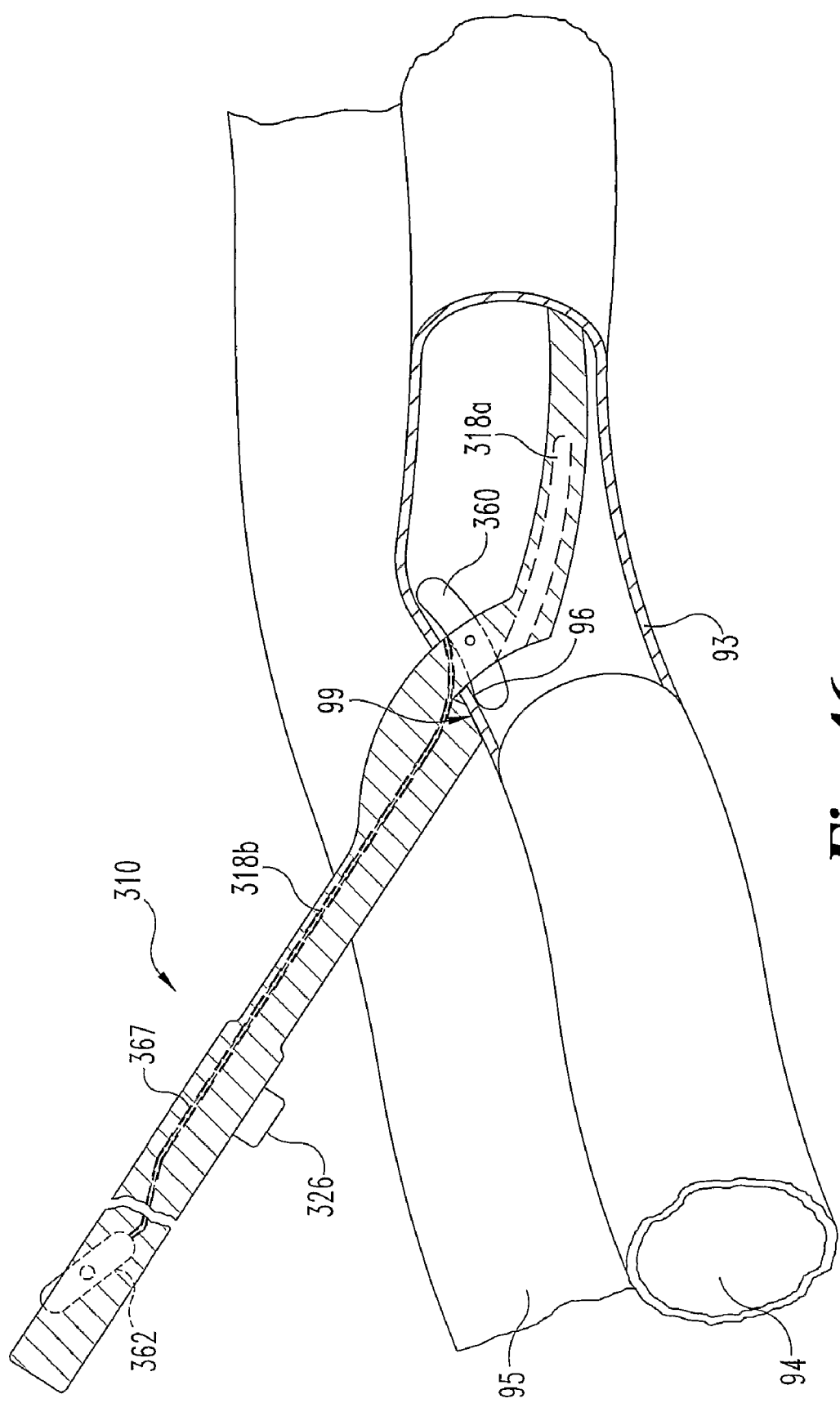

Referring now to FIG. 46, suturing device 310 can be rotated about its longitudinal axis to a second suturing position. In general, the same procedure as described above can be employed for the present embodiment. However, slight modifications of the procedure can facilitate the use of the present device. First distal member 314 need not be removed or completely removed from the lumen 94 of vessel 93. However, it may be preferable to retract foot 360 to the non-deployed position prior to rotation of the device to the second suturing position. This can reduce the risk that foot 360 will exert unnecessary force and/or torque on the vascular tissue, which could cause injury such as tears or over extension of the tissue. Once the device is repositioned at the second suture position, foot 360 can be re-deployed using lever 362 as described above.

As illustrated in FIG. 46, a second needle 318b can be advanced through the needle channel 324 using needle pusher 326 to pierce vascular tissue at a second puncture site 99. Second needle 318b can be further advanced into receptacle 322.

Figure 11:
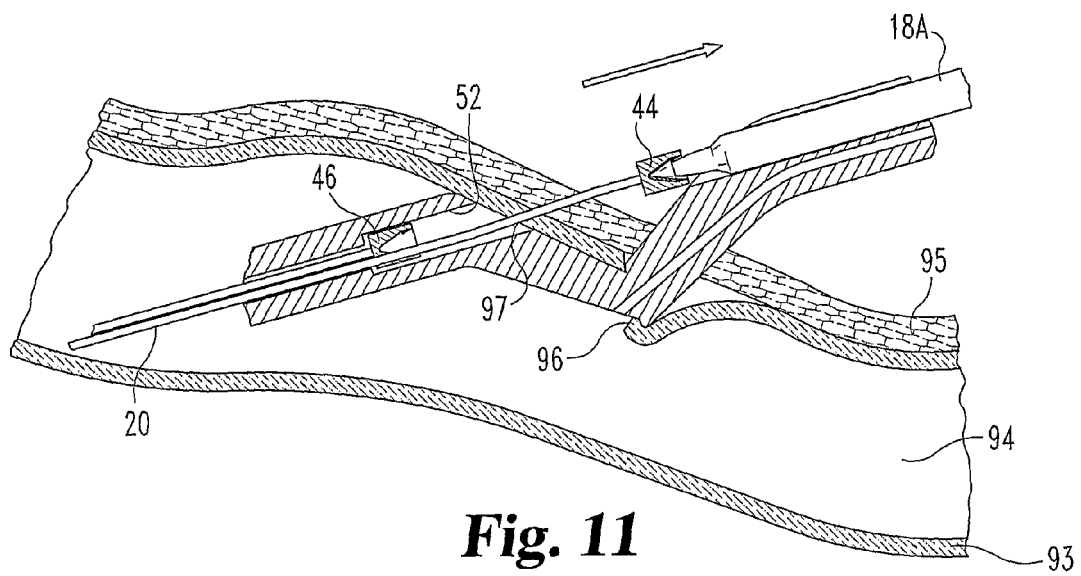
Figure 47:
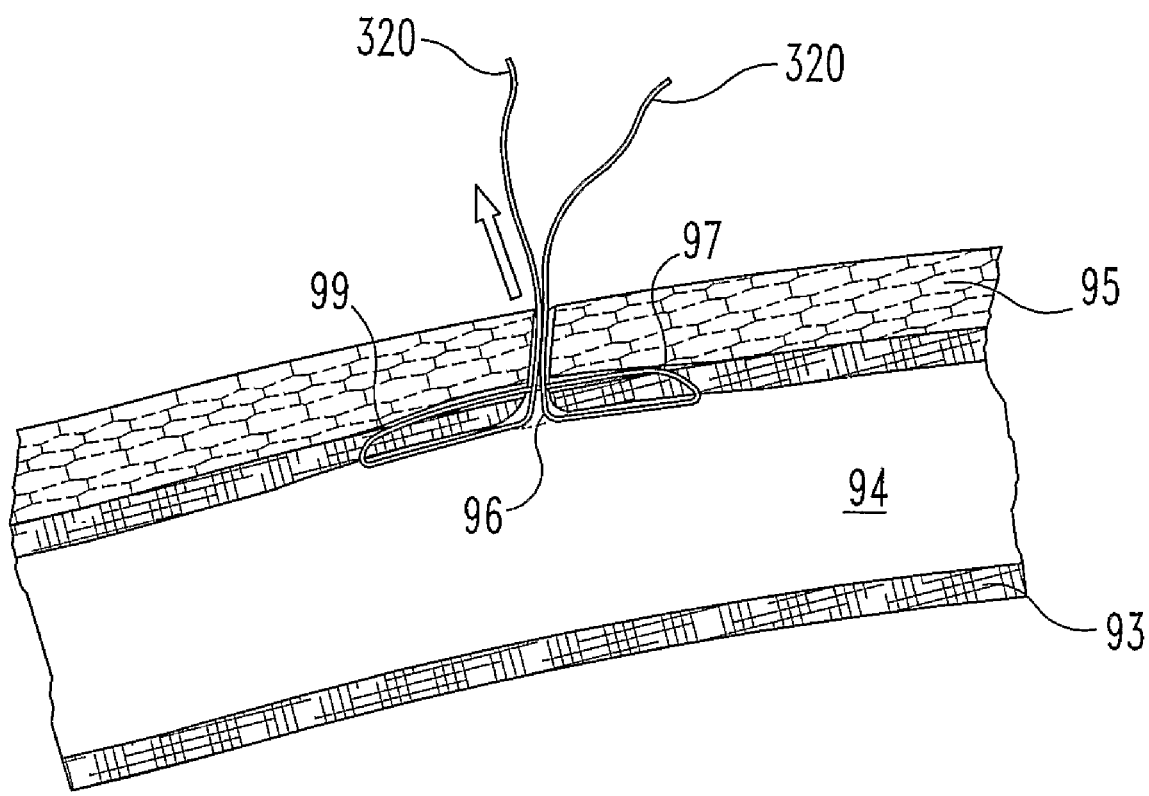

After the first and second needles 318a and 318b have pulled suture material through the vascular tissue, the suturing device 310 can be withdrawn from the vessel. This results in a suture path that extends in a distal direction through the wound in the vessel to a first suture site in the vascular tissue; out through the first suture site in a proximal direction; across the wound on the proximal side of the tissue to a second suture site; then in a distal direction through the second suture site back into the lumen of the vessel and from there back out in the proximal direction through the wound as illustrated in FIG. 47. If needles 318a and 318b have a single piece of suture material 320 connected to their proximal end; the suture material illustrated in FIG. 11 is a single strand with two ends extending through the puncture wound 96. If needles 318a and 318b have separate suture material connected to their proximal end, there would be a different configuration. Furthermore, if the suture needles are configured to capture a needle retention element the needle capture element as illustrated and described in connection with FIGS. 23-36 above, the suture material will take still a different path. In any event, accurate positioning of the suturing device 310 is enabled with the deployable foot 360.

Once the device 310 is sufficiently removed or completely removed, the needles 318a, 318b and the attached suture material can be gathered in an appropriate fashion depending upon the number of individual lengths of suture material. When desired, the needles can be separated from the suture material. The suture material is gathered to gather to effect wound closure. A suture knot can be tied by hand. A loosely tied knot can be advanced to the external surface of the vessel using a knot pusher. Alternatively, a knot box can be used to form a knot which is then advanced to the external surface of the vessel. Examples of suitable knot boxes are illustrated and described in WO 01/19258, which is incorporated herein by reference.

Alternatively, one or more knot replacement technologies such can be used to secure closure of the wound using the suture material. Consequently, the suture knot or suture securing devices can be positioned across the proximal side of the wound to effect closure.

FIG. 21 is a perspective view of a suture securing device 102 for use in the present invention. Suture securing device 102 is described and illustrated in US Patent Publication No.

2004/0102809 which is incorporated herein by reference. In use, device 102 can secure ends of one, two, three or more lengths of suture material. Two lengths of suture material 104a and 104b are illustrated with device 102. The lengths of suture material are threaded into the flexible elements 105a and 105b which are then locked or fixed together securing the suture material therein.

FIG. 22 is another embodiment of suture securing devices 106a and 106b for use in the present invention. Devices 106a and 106b are described in US Patent Publication No. 2003/0229377 which is incorporated herein by reference in its entirety. Devices 106a and 106b cooperate by separately clipping onto a selected length of suture material 104a or 104b which have previously pulled taut to close wound or complete the surgical procedure. The devices prevent the suture material from regressing back through the sutured tissue.

Figure 48:
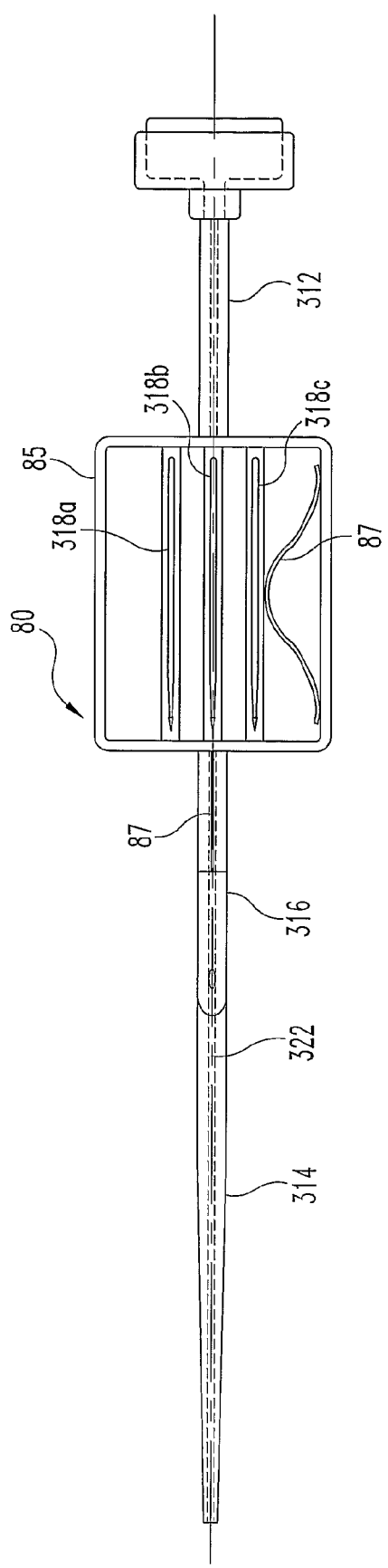
FIG. 48 is a perspective view of one embodiment of a suture securing device for use in the present invention.

FIG. 48 shows still other embodiment in which the receptacle 322 is sized to receive one two or more needles 318a, 318b, 318c, which can be retained without any further modifications. Receptacle 322 includes one or more needle capture elements, for example, one or more plugs 123 or pierceable material elements or projection(s) that can be pierced by needles advanced into receptacle 322. In this embodiment, needle 318a is captured within the receptacle reducing the risk of dislocation during manipulation of the suturing device. Examples of suitable needle capturing elements are illustrated and described in connection with FIGS. 23-36 above.

Figure 49:
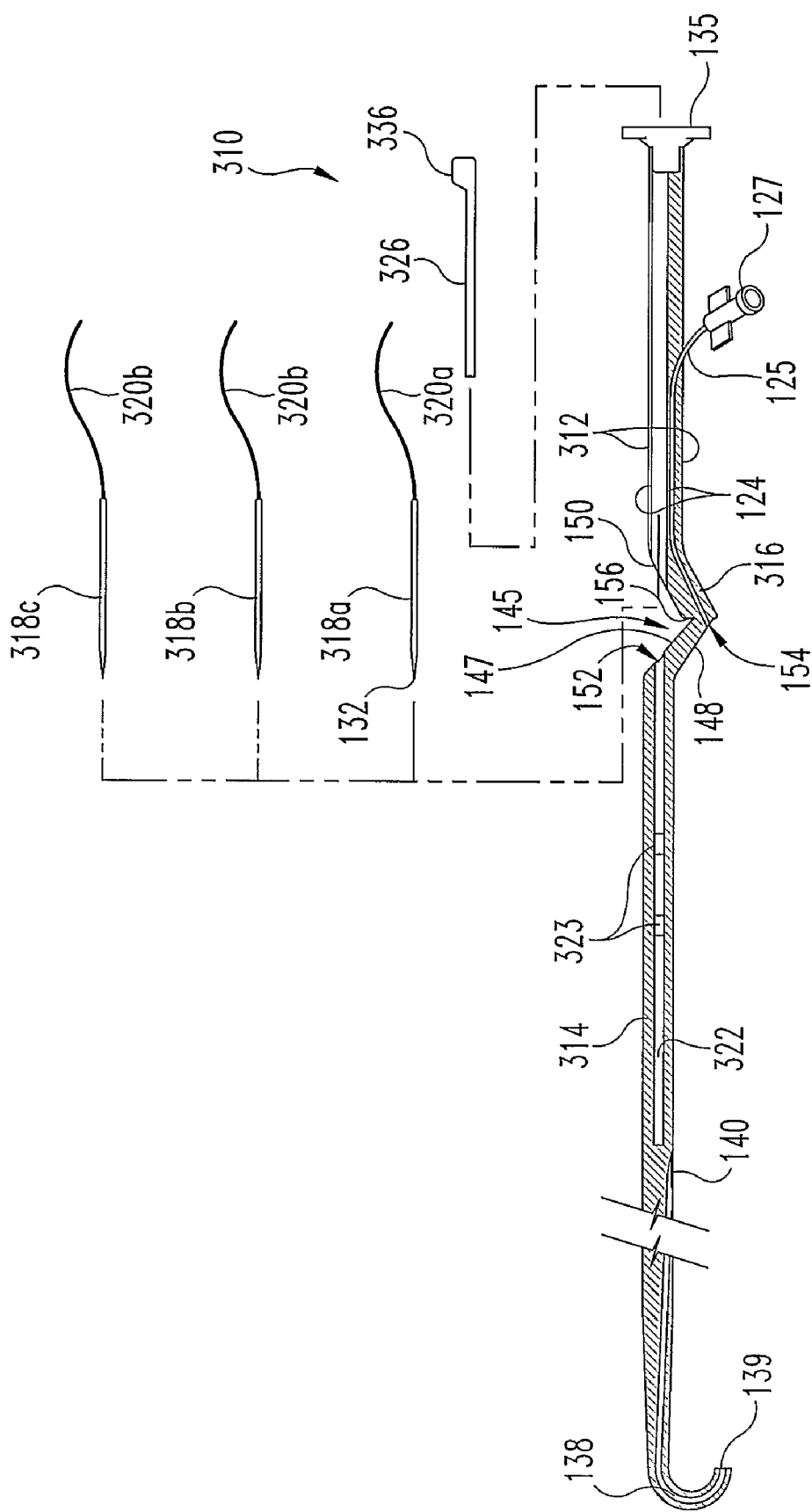
FIG. 49 is a perspective view of an alternative embodiment of a suture securing device for use in the present invention.
Figure 50:
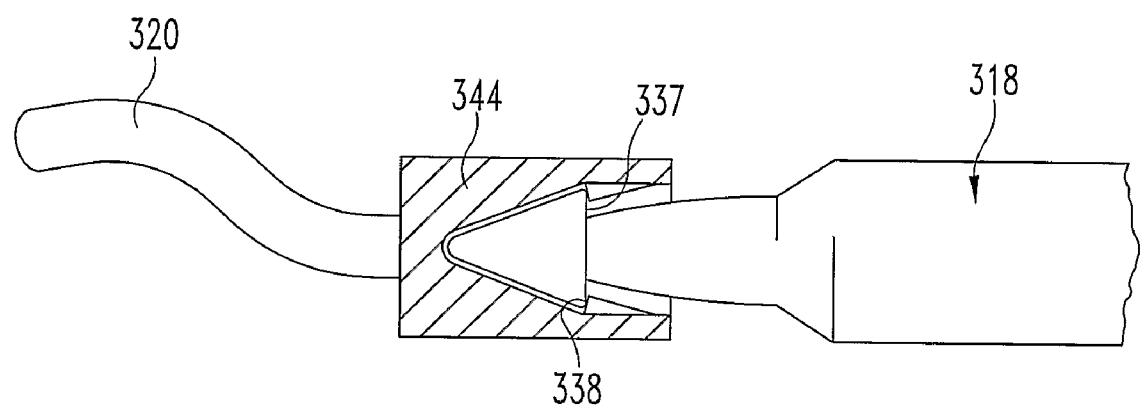
FIG. 50 is a perspective view of one embodiment of a suturing device with a needle capture element in accordance with the present invention.

As shown in FIGS. 49 and 50, one or more needle engaging fittings attached to suture material can be positioned within receptacle 322. In this embodiment, needles 318a, 318b, 318c, . . . can each include a recessed surface 337 suitable for engaging with tabs 338 on fittings 344 in the receptacle 322. Fittings 44 may be attached to suture material 320, also at least partially contained within receptacle 322. Examples of suitable fittings and needles are illustrated and described in connection with FIGS. 1-22 above.

The present invention provides a variety of means, devices and methods for closing wounds in tissue and is particularly but not exclusively suitable for vascular tissue. It will be understood that the present invention contemplates modifications as would occur to those skilled in the art without departing from the spirit of the present invention. In addition, the various structures, elements, and procedural steps or stages have been described with reference to specified embodiments and devices. Each of the individual or a combination of the structures, elements, and procedural steps or stages are contemplated to be combinable with each of the other embodiments and devices described herein and as such are contemplated to be within the scope of the present invention.

All publications, patents, and patent applications cited in this specification are herein incorporated by reference as if each individual publication, patent, or patent application was specifically and individually indicated to be incorporated by reference and set forth in its entirety herein. Further, any theory of operation, proof, or finding stated herein is meant to further enhance understanding of the present invention and is not intended to make the scope of the present invention dependent upon such theory, proof, or finding.

What is claimed is:

1. A suturing device for suturing an opening in a vascular vessel, said device comprising:
a proximal member including an elongated body having a single needle channel configured to receive a plurality of needles one at a time therethrough;
a distal member configured to be inserted within a lumen of the vascular vessel, said distal member having a receptacle located therein;
an intermediate member disposed between the proximal member and the distal member, said intermediate member defining a tissue receiving area and having a first opening providing a passageway to the single needle channel and a second opening providing a passageway into the receptacle;
a length of suture material comprising a first end having a first needle engaging fitting and a second end having a second needle engaging fitting, the first needle engaging fitting and the second needle engaging fitting being positioned in the receptacle, wherein the receptacle in said distal member is substantially in line with the longitudinal axis of said needle channel and the entire length of suture is positioned in the receptacle and wherein the first needle engaging fitting has a cross-sectional diameter greater than that of the second needle engaging fitting within the receptacle.

2. The device of claim 1 wherein each of the first needle engaging fitting and the second needle engaging fittings comprises a ferrule having a needle engaging tab.

3. The device of claim 2 wherein the ferrule comprises a cylindrical housing having a plurality of needle engaging tabs extending radially into the cylindrical housing.

4. The device of claim 2 further comprising a needle having a recessed engaging surface configured to engage with the plurality of needle engaging tabs.

5. The device of claim 1 wherein the first needle engaging fitting is disposed proximally to the second needle engaging fitting within the receptacle.

6. The device of claim 1 further comprising a cartridge slidably mounted on the proximal member and containing a plurality of needles.

* * * * *